United States Patent
Barbas, III et al.

(10) Patent No.: US 6,242,568 B1
(45) Date of Patent: Jun. 5, 2001

(54) ZINC FINGER PROTEIN DERIVATIVES AND METHODS THEREFOR

(75) Inventors: Carlos F. Barbas, III; Joel M. Gottesfeld, both of San Diego; Peter E. Wright, La Jolla, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/676,318

(22) PCT Filed: Jan. 18, 1995

(86) PCT No.: PCT/US95/00829

§ 371 Date: Dec. 30, 1996

§ 102(e) Date: Dec. 30, 1996

(87) PCT Pub. No.: WO95/19431

PCT Pub. Date: Jul. 20, 1995

Related U.S. Application Data

(63) Continuation-in-part of application No. 08/312,604, filed on Sep. 28, 1994, now abandoned, which is a continuation-in-part of application No. 08/183,119, filed on Jan. 18, 1994, now abandoned.

(51) Int. Cl.[7] .................. C07K 14/435; C07K 19/00; C12N 15/00; C12N 15/70

(52) U.S. Cl. .................. 530/350; 530/400; 435/69.1; 435/252.3; 435/320.1; 435/417; 536/23.5; 536/23.6; 536/23.72

(58) Field of Search .................. 530/350, 400; 514/6; 424/450; 435/69.1, 252.3, 320.1, 471; 536/23.5, 23.6, 23.72

(56) References Cited

U.S. PATENT DOCUMENTS

| | | | |
|---|---|---|---|
| 4,990,607 | * | 2/1991 | Katagiri et al. .................. 536/23.6 |
| 5,096,815 | * | 3/1992 | Ladner et al. .................. 435/69.1 |
| 5,243,041 | * | 9/1993 | Fernandez-Pol .................. 536/23.5 |
| 5,324,638 | * | 6/1994 | Tao et al. .................. 435/69.1 |
| 5,324,818 | * | 6/1994 | Nabel et al. .................. 530/350 |
| 5,340,739 | * | 8/1994 | Stevens et al. .................. 435/240.1 |
| 5,350,840 | * | 9/1994 | Call et al. .................. 536/23.1 |
| 5,376,530 | * | 12/1994 | De The et al. .................. 435/6 |
| 5,403,484 | * | 4/1995 | Ladner et al. .................. 435/235.1 |
| 5,597,693 | * | 1/1997 | Evans et al. .................. 435/6 |

OTHER PUBLICATIONS

Celenza, J. L., et al., Science, vol. 233, "A yeast gene that is essential for release from glucose repression encodes a protein kinase", pp. 1175–1180, 1986.*

Singh, H., et al., Cell, vol. 52, "Molecular cloning of an enhancer binding protein: Isolation by screening of an expression library with a recognition site DNA", pp. 415–423, 1988.*

Wright, J. J., et al., Science, vol. 248, "Expression of a zinc–finger gene in HTLV–I–and HTLV–II–transformed cells", pp. 588–591, 1990.*

(List continued on next page.)

Primary Examiner—Ponnathapu Achutamurthy
Assistant Examiner—William W. Moore
(74) Attorney, Agent, or Firm—Gray Cary Ware & Freidenrich LLP; Lisa A. Haile

(57) ABSTRACT

The present invention provides zinc finger nucleotide binding polypeptide variants that have at least two zinc finger modules that bind to a target cellular nucleotide sequence and modulate the transcriptional function of the cellular nucleotide sequence. Also provided are methods of use of such zinc finger nucleotide binding polypeptide variants and methods for isolating the same using expression libraries encoding the polypeptide variants containing randomized substitutions of amino acids. Exemplary zinc finger nucleotide binding polypeptide variants of the invention include two cysteines and two histidines whereby both cysteines are amino proximal to both histidines.

56 Claims, 23 Drawing Sheets

OTHER PUBLICATIONS

Debs, R. J., et al., The Journal of Biological Chemistry, vol. 265, "Regulation of gene expression in vivo by liposome–mediated delivery of a purified transcription factor", pp. 10189–10192, 1990.*

Bergqvist, A., et al., Nucleic Acids Research, vol. 18, "Loss of DNA–binding and new transcriptional trans–activation function in polyomavirus large T–antigen with mutation of zinc finger motif", pp. 2715–2720, 1990.*

Rauscher, F. J., et al., Science, vol. 250, "Binding of the Wilms' tumor locus zinc finger protein to the EGR–1 consensus sequence", pp. 1259–1262, 1990.*

South, T. L., et al., Biochemistry, vol. 29, "The nucleocapsid protein isolated from HIV–1 particles binds zinc and forms retroviral–type zinc fingers", pp. 7786–7789, 1990.*

Ray, A., et al., Proceedings of the National Academy of Sciences, U.S.A., vol. 88, "Repressor to activator switch by mutations in the first Zn finger of the glucocorticoid receptor", pp. 7086–7090, 1991.*

Agarwal, K., et al., Biochemistry, vol. 30, "Stimulation of transcript elongation requires both the zinc finger and RNA polymerase II binding domains of human TFIIS", pp. 7842–7851, 1991.*

Barbas, III, C. F., et al., Proceedings of the National Academy of Sciences, U.S.A, vol. 89, "Semisynthetic combinatorial antibody libraries: A chemical solution to the diversity problem", pp. 4457–4461, 1992.*

Thukral, S. K., et al., Molecular and Cellular Biology, vol. 12, "Mutations in the zinc fingers of ADR1 that change the specificity of DNA binding and transactivation", pp. 2784–2792, 1992.*

Quigley, C. A., et al., Molecular Endocrinology, vol. 6, "Complete androgen insensitivity due to deletion of exon C of the androgen receptor gene highlights the functional importance of the second zinc finger of the androgen receptor in vivo", pp. 1103–1992.*

Jacobs, G. H., The EMBO Journal, vol. 11, "Determination of the base recognition positions of zinc fingers from sequence analysis", pp. 4507–4517, 1992.*

Yu, M., et al., Proceedings of the National Academy of Sciences, U.S.A., vol. 90, "A hairpin ribozyme inhibits expression of diverse strains of human immunodeficiency virus type 1", pp. 6340–6344, 1993.*

Rollins, M. B., et al., Molecular and Cellular Biology, vol. 13, "Role of TFIIIA zinc fingers in vivo: Analysis of single–finger function in developing Xenopus embryos", pp. 4776–4783, 1993.*

Julian, N., et al., FEBS Letters, vol. 331, "Replacement of His23 by Cys in a zinc finger of HIV–1 NCp7 led to change in 1H NMR–derived 3D structure and to a loss of biological activity", pp. 43–48, 1993.*

Jamieson, A., C., et al., Biochemistry, vol. 33, "In vitro selection of zinc fingers with altered DNA–binding specificity", pp. 5689–5695, 1994.*

Pabo, C. O., Annual Review of Biochemistry, vol. 61, "Transcription factors: Structural families and principles of DNA recognition", pp. 1053–1095, 1992.*

* cited by examiner $\frac{Y}{F}$ X C  X$_{2-4}$  C  X$_3$  F  X$_5$   L  X$_2$  H  X$_{3-4}$  H  CONSENSUS

Ⓨ I Ⓒ S F A D Ⓒ G A A Ⓨ N K̲ N W K̲ Q A Ⓗ L C K Ⓗ T  FINGER 1

Ⓔ P Ⓒ K E E G Ⓒ E K G Ⓕ T S L H̲ Ⓗ T R̲ Ⓗ S L T Ⓗ T  FINGER 2

Ⓔ T Ⓒ D S D G Ⓒ D L R̲ Ⓔ T T K̲ A̲ N M K̲ K̲ Ⓗ F N R F Ⓗ  FINGER 3 antiparallel β-turn ⟨⟨⟩⟩    α helix

FINGER 3    FINGER 2    FINGER 1

FIG. 2B

```
                    10              20            *30             *40
         CTC GAG CCC *TAT GCT TGC *CCT GTC GAG  TCC TGC GAT CGC TTT TCT
          L   E   P   Y   A   C   P   V   E    S   C   D   R   F   S
         GAG CTC GGG ATA CGA ACG CGA CAG CTC AGG CTA GCG GCG AAA AGA
          E   L   G   I   R   T   R   Q   L   R   L   A   A   K   R  >

*50              *60            *70             *80
         GGC TCG GAT GAG CTT ACC CGC CAT ATC CGC ACA GGC CAG AAG
          G   S   D   E   L   T   R   H   I   R   T   G   Q   K
         GCG AGC CTA CTC GAA TGG GCG GTA TAG GCG TGT CCG GTC TTC
          A   S   L   L   E   W   A   V   *   A   C   P   V   F  >

*100             *110            *120            *130            *140
         CCC TTC CAG TGT CGA ATA TGC ATG CGT AAC TTC AGT CGT AGT GAC CAC
          P   F   Q   C   R   I   C   M   R   N   F   S   R   S   D   H
         GGG AAG GTC ACA GCT TAT ACG TAC GCA TTG AAG TCA GCA TCA CTG GTG
          G   K   V   T   A   Y   T   Y   A   L   K   S   A   S   L   V  >
```

FIG. 7A

```
                    150              160              170              180              190
                     *                *                *                *                *
CTT ACC ACC CAC ATC CGC ACC CAC ACA GGC GAG AAG CCT TTT GCC TGT
GAA TGG TGG GTG TAG GCG TGG GTG TGT CCG CTC TTC GGA AAA CGG ACA
 L   T   T   H   I   R   T   H   T   G   E   K   P   F   A   C>

200              210              220              230              240
                     *                *                *                *                *
GAC ATT TGT GGG AGG AAG TTT GCC AGG AGT GAT GAA CGC AAG AGG CAT
CTG TAA ACA CCC TCC TTC AAA CGG TCC TCA CTA CTT GCG TTC TCC GTA
 D   I   C   G   R   K   F   A   R   S   D   E   R   K   R   E>

250              260              270
                     *                *                *
ACG AAA ATC CAT TTA AGA CAG AAG GAC ACT AGT
TGG TTT TAG GTA AAT TCT GTC TTC CTG TGA TCA
 T   K   I   E   L   R   Q   K   E   T   S>
```

*FIG. 7B*

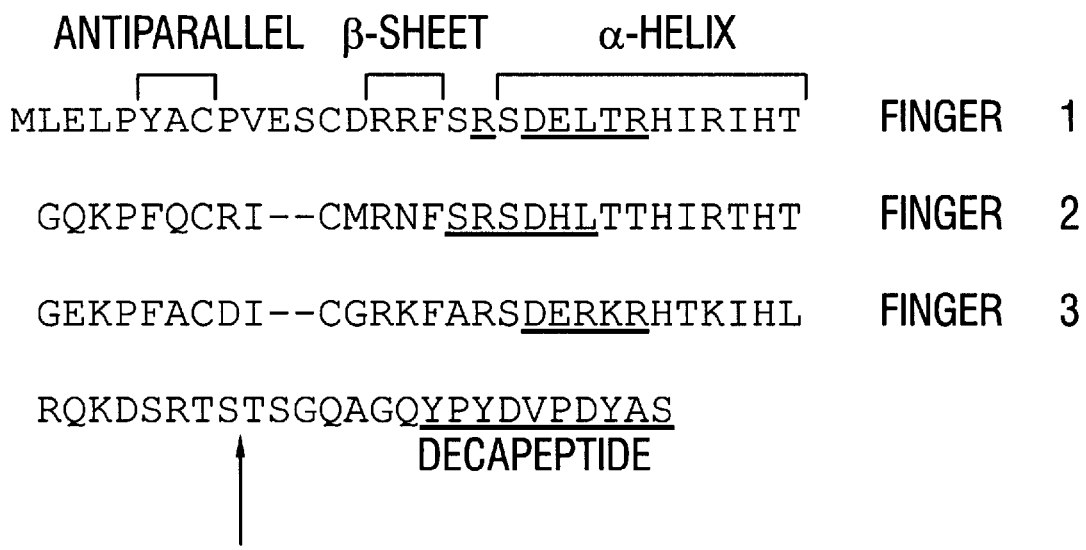
FIG. 8A
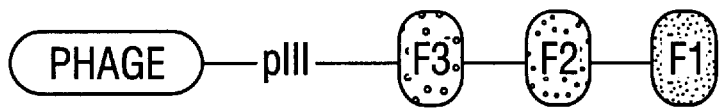
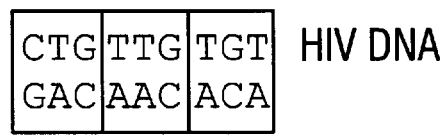
FIG. 8B

AMINO ACID SEQUENCES OF SELECTED ZINC FINGER PROTEINS

| FINGER 1 | SELECTION | FINGER 2 | SELECTION | FINGER 3 | SELECTION |
|---|---|---|---|---|---|
| GCG | TGT | TGG | TTG | GCG | CTG |
| -123456 | -123456 | -2-11234 | -2-11234 | -123456 | -123456 |
| RDELTR-(WT) | | SRSDHL-(WT) | | RDERKR-(WT) | |
| KADLKR-(C7) | QTASKA-(F8) | TYLNTP | GVTMQP-(G3) | RDLANS | NVGDKP |
| KCVRGR-(C9) | PTHLQT-(F15) | GYRAAP | PQPLSD | SGQWWR-(A14) | SWICGI |
| KCDRGR | PERTQP | LYRYHL | REQVSR-(G4) | SLLVIA | IAWMEL |
| KYCRTR | TSEADH | PTLVNA | THMWMI | VSVRGL | IMMTFF |
| KQLPWT-(C10) | SEQRYP | VRPHQR | QRMRTL-(G5) | | RECRML |
| KNSQHP | HQQNKP | PFCPYR | QRVGLF | | IALLDT |
| KCQMDS | RGQGMA | | LRTGNY-(G6) | | NVQGLR |
| QQVTRT | RARQTG | | EREFSL | | |
| TQSQSP | ENSFTD | | EKESRG | | |
| VHIQAN | NVMGHD | | EGVRKN | | |
| | NRGQRK | | TGVNSI | | |
| | SRPSQW | | TQARPP | | |
| | TSEADH | | THMWMI | | |

*FIG. 9*

| KINETIC AND EQUALIBRIUM DISSOCIATION CONSTANTS OF ZINC FINGER PROTEINS | | | | | |
|---|---|---|---|---|---|
| ZINC FINGER PROTEIN | BINDING SITE | $K_{ON}(X10^4)$ $(M^{-1}s^{-1})$ | $K_{OFF} (x 10^{-4})$ $(s^{-1})$ | $K_{d}(x10^{-9})$ $(M)$ | $K_d/K_d(TARGET)$ |
| WT | GCG | 3.0±0.04 | 2.0±0.1 | 6.5 | 1 |
|  | TGT | 1.1±0.2 | 9.0±1.0 | 81.8 | 12.6 |
| C7 | GCG | 2.4±0.4 | 1.5±0.7 | 6.3 | 1 |
|  | GCG | 8.0±0.7 | 0.4±0.1 | 0.5 | 108.8 |
| C9 | TGT | 0.9±0.1 | 4.9±2.0 | 54.4 | 1 |
|  | GCG | 2.0±0.2 | 1.3±0.3 | 6.5 | 39.3 |
| C10 | TGT | 0.9±0.1 | 23.0±3.0 | 255.6 | 1 |
|  | GCG | 1.8±0.1 | 4.5±2.0 | 25.0 | 1.9 |
| F8 | TGT | 0.3±0.002 | 1.4±0.1 | 46.7 | 1 |
|  | TGT | 3.7±1.0 | 11.0±1.5 | 29.7 | 3.6 |
| F15 | GCG | 4.8±0.1 | 52.0±0.9 | 108.3 | 1 |
|  | TGT | 1.9±0.1 | 7.9±1.0 | 41.6 | 4.5 |
|  | GCG | 0.9±0.3 | 17.0±1.7 | 188.9 |  |
| G3 | TTG | 1.7±0.2 | 2.7±0.2 | 15.9 | 1 |
|  | TGG | 2.7±0.3 | 6.0±0.2 | 22.2 | 1.4 |
| G4 | TTG | 3.3±0.2 | 2.1±0.1 | 6.4 | 1 |
|  | TGG | 2.5±0.6 | 5.7±0.2 | 22.8 | 3.6 |
| G5 | TTG | 0.8±0.1 | 2.2±0.02 | 27.5 | 1 |
|  | TGG | 1.9±0.2 | 9.1±0.1 | 47.9 | 1.7 |
| G6 | TTG | 10.0±1.0 | 4.6±0.3 | 4.6 | 1 |
|  | TGG | 0.7±0.1 | 1.4±0.1 | 20.0 | 4.3 |
| A14 | GCG | 1.3±0.1 | 1.7±0.0 | 13.1 | 1 |
|  | CTG | 0.2±0.0 | 10.0±0.4 | 500.0 | 38.2 |

FIG. 11

```
                          10          20          30          40
                          *           *           *           *
ATG CTC GAG CTC CCC TAT GCT TGC CCT GTC GAG TCC TGC GAT CGC CGC
TAC GAG CTC GAG GGG ATA CGA ACG GGA CAG CTC AGG ACG CTA GCG GCG
 M   L   E   L   P   Y   A   C   P   V   E   S   C   D   R   R>

50          60          70          80          90
          *           *           *           *           *
TTT TCT CGC TCG GAT GAG CTT ACC CGC CAT ATC CGC CAC ACA GGC
AAA AGA GCG AGC CTA CTC GAA TGG GCG GTA TAG GCG TGT GTG CCG
 F   S   R   S   D   E   L   T   R   H   I   R   H   T   G>

100         110         120         130         140
          *           *           *           *           *
CAG AAG CCC TTC CAG TGT CGA ATA TGC ATG CGT AAC TTC AGT CGT AGT
GTC TTC GGG AAG GTC ACA GCT TAT ACG TAC GCA TTG AAG TCA GCA TCA
 Q   K   P   F   Q   C   R   I   C   M   R   N   F   S   R   S>

150         160         170         180         190
          *           *           *           *           *
GAC CAC CTT ACC ACC CAC CAC ATC CGC ACC ACC CAC ACA GGC GAG CTC CCT TTT
CTG GTG GAA TGG TGG GTG GTG TAG GCG TGG TGG GTG TGT CCG CTC GAG GGA AAA
 D   H   L   T   T   H   H   I   R   T   T   H   T   G   E   L   P   F>
```

```
      200         210         220         230         240
       *           *           *           *           *
GCC TGT GAC ATT TGT GGG AGG AAG TTT GCC AGG AGT GAT GAA CGC AAG
CGG ACA CTG TAA ACA CCC TCC TTC AAA CGG TCC TCA CTA CTT GCG TTC
 A   C   D   I   C   G   R   K   F   A   R   S   D   E   R   K>

250         260         270         280
           *           *           *           *
AGG CAT ACC AAA ATC CAT GGT ACC GGT CAG AAG CCC ACT AGT GGC GGT GGT
TCC GTA TGG TTT TAG GTA CCA TGG CCA GTC TTC GGG TGA TCA CCG CCA CCA
 R   H   T   K   I   H   G   T   G   Q   K   P   T   S   G   G   G>
                                                                  LINKER 290         300         310         320         330
       *           *           *           *           *
CGG ATC GCC CGG CTG GAG GAA CTC GAG AAA GTG AAA ACC TTG AAA GCG CAA AAC
GCC TAG CGG GCC GAC CTC CTT GAG CTC TTT CAC TTT TGG AAC TTT CGC GTT TTG
 R   I   A   R   L   E   E   L   E   K   V   K   T   L   K   A   Q   N>
                                                                       JUN
```

```
     340                350             360             370             380
      *                  *               *               *               *
TCC GAG CTG GCG TCC ACC GCC AAC ATG CTC AGG GAA CAG GTG CAC GCA CAG
AGG CTC GAC CGC AGG TGC CGG TTG TAC GAG TCC CTT GTC CAC CGT GTC
 S   E   L   A   S   T   A   N   M   L   R   E   Q   V   A   Q >

390                400             410             420             430
      *                  *               *               *               *
CTT AAA CAG AAA GTC ATG AAC CAC GCT AGC GGC CAG GCC GGC CAG TAC
GAA TTT GTC TTT CAG TAC TTC GTG CGA TCG CCG GTC CGG CCG GTC ATG
 L   K   Q   K   V   M   N   H   A   S   G   Q   A   G   Q   Y >

440                450             460
      *                  *               *
CCG TAC GAC GTT CCG GAC TAC GCT TCT TAA
GGC ATG CTG CAA GGC CTG ATG CGA AGA ATT
 P   Y   D   V   P   D   Y   A   S   * >
                     |_____|
                          DECAPEPTIDE TAG
```

FIG. 13B

```
        10          20          30          40
         *           *           *           *
ATG CTC GAG CTC CCC TAT GCT TGC CCT GTC CAG TCC TGC GAT CGC CGC
TAC GAG CTC GAG GGG ATA CGA ACG GGA CAG CTC AGG ACG CTA GCG GCG
 M   L   E   L   P   Y   A   C   P   V   Q   S   C   D   R   R>

50          60          70          80          90
         *           *           *           *           *
TTT TCT CGC TCG GAT GAG CTT ACC CGC CAT CGC ATC CAC ACA GGC
AAA AGA GCG AGC CTA CTC GAA TGG GCG GTA GCG TAG GTG TGT CCG
 F   S   R   S   D   E   L   T   R   H   I   R   I   H   T   G>

100         110         120         130         140
         *           *           *           *           *
CAG AAG CCC TTC CAG TGT CGA ATA TGC ATG CGT AAC TTC AGT CGT AGT
GTC TTC GGG AAG GTC ACA GCT TAT ACG TAC GCA TTG AAG TCA GCA TCA
 Q   K   P   F   Q   C   R   I   C   M   R   N   F   S   R   S>

150         160         170         180         190
         *           *           *           *           *
GAC CAC CTT ACC ACC CAC ATC CGC ACC CAC ACA GGC GAG AAG CCT TTT
CTG GTG GAA TGG TGG GTG TAG GCG TGG GTG TGT CCG CTC TTC GGA AAA
 D   H   L   T   T   H   I   R   T   H   T   G   E   K   P   F>
```

FIG. 14A-1

```
        200           210           220           230           240
         *             *             *             *             *
GCC TGT GAC ATT TGT GGG AGG AAG TTT GCC AGG AGT GAT GAA CGC AAG
CGG ACA CTG TAA ACA CCC TCC TTC AAA CGG TCA CTA CTT GCG TTC
 A   C   D   I   C   G   R   K   F   A   R   S   D   E   R   K>

250           260           270           280
         *             *             *             *
AGG CAT ACC AAA ATC CAT ACC GGT CAG AAG CCC ACT AGT GGC GGT GGT
TCC GTA TGG TTT TAG GTA TGG CCA GTC TTC GGG TGA TCA CCG CCA CCA
                                                    ┌───────LINKER
 R   H   T   K   I   H   T   G   Q   K   P   T   S   G   G   G 290           300           310           320           330
         *             *             *             *             *
CTG ACC GAC ACC CTG CAG GCG GAA ACC GAC CAG CTG GAA GAC GAA AAA
GAC TGG CTG TGG GAC GTC CGC CTT TGG CTG GTC GAC CTT CTG CTT TTT
─────┐
 L   T   D   T   L   Q   A   E   T   D   Q   L   E   D   E   K>
                                                         └─► FOS
```

*FIG. 14A-2*

```
      340                350                 360               370                380
       *                  *                   *                 *                  *
TCC GCG CTG CAA ACC GAA ATC GCG AAC CTG CTG GAC AAA GAA AAA GAA AAG
AGG CGC GAC GTT TGG CTT TAG CGC TTG GAC CTG CTT TTT CTT TTT CTT TTC
 S   A   L   Q   T   E   I   A   N   L   L   D   K   E   K   E   K>

390                400                 410               420                430
       *                  *                   *                 *                  *
CTG GAG TTC ATC CTG GCG GCA CAC GCT AGC GGC CAG GCC GGC CAG TAC TTT
GAC CTC AAG TAG GAC CGC CGT GTG CGA TCG CCG GTC CGG CCG GTC ATG TTT
 L   E   F   I   L   A   A   H   A   S   G   Q   A   G   Q   Y>

440                450                 460
       *                  *                   *
CCG TAC GAC GTT CCG GAC TAC GCT TCT TAA
GGC ATG CTG CAA GGC CTG ATG CGA AGA ATT
 P   Y   D   V   P   D   Y   A   S   *>
                      ─────────────────────
                         DECAPEPTIDE TAG

FIG. 14B
```

```
ATG AAA CTG CTC GAG CCC TAT GCT TGC CCT GTC GAG TCC TGC GAT CGC
TAC TTT GAC GAG CTC GGG ATA CGA ACG CAG ACG CTC AGG ACG CTA GCG
 M   K   L   L   E   P   Y   A   C   P   V   E   S   C   D   R >

CGC TTT TCT AAG TCG GCT GAT CTG AAG CGC ATC CGC ATC CAC ACT
GCG AAA AGA TTC AGC CGA CTA GAC TTC GCG TAG GCG TAG GTG TGA
 R   F   S   K   S   A   D   L   K   R   I   R   I   H   T >

GGC GAA AAA CCG TAC GCG TGC CCT GTC GAG TCC TGC GAT CGC CGC TTT
CCG CTT TTT GGC ATG CGC ACG GGA CAG CTC AGG ACG CTA GCG GCG AAA
 G   E   K   P   Y   A   C   P   V   E   S   C   D   R   R   F >

TCT AAG TCG GCT GAT CTG AAG CGC ATC CGC ATC CAC ACC GGG CCC CTC
AGA TTC AGC CGA CTA GAC TTC GCG TAG GCG TAG GTG TGG CCC GGG GAG
 S   K   S   A   D   L   K   R   I   R   I   H   T   G   P   E >
```

FIG. 15A

```
                  200            210            220            230            240
                   *              *              *              *              *
AAG CCC TAT GCT TGC CCT GTC GAG TCC TGC GAT CGC TTT TCT AAG
TTC GGG ATA CGA ACG GGA CAG CTC AGG ACG CTA GCG AAA AGA TTC
 K   P   Y   A   C   P   V   E   S   C   D   R   F   S   K>

250            260            270            280
                   *              *              *              *
TCG GCT GAT CTG AAG CGC CAT ATC CGC ATC CAC ACC GGT CAG AAG CCC
AGC CGA CTA GAC TTC GCG GTA TAG GCG TAG GTG TGG CCA GTC TTC GGG
 S   A   D   L   K   R   H   I   R   I   H   T   G   Q   K   P>

290
                   *
ACT ACT
TGA TCA
 T   S>
```

*FIG. 15B*

ATG CTC GAG CTC CCC TAT GCT CCT TGC CCT GTC GAG TCC TGC GAT CGC CGC
TAC GAG CTC GAG GGG ATA CGA GGA ACG CAG CTC AGG ACG CTA GCG GCG
 M   L   E   L   P   Y   A   C   P   V   E   S   C   D   R   R>

TTT TCT CGC TCG GAT GAG CTC ACC CGC CAT ATC CGC ATC CAC ACA GGC
AAA AGA GCG AGC CTA CTC GAA TGG GCG GTA TAG GCG TAG GTG TGT CCG
 F   S   R   S   D   E   L   T   R   H   I   R   I   H   T   G>

CAG AAG CCC TTC CAG TGT CGA ATA TGC CGA ATC AAC TTC AGT CGT AGT
GTC TTC GGG AAG GTC ACA GCT TAT ACG GCT TAG TTG AAG TCA GCA TCA
 Q   K   P   F   Q   C   R   I   C   R   I   N   F   S   R   S>

GAC CAC CTT ACC ACC CAC ATC CGC ACC CAC ACA GGC GAG AAG CCT TTT
CTG GTG GAA TGG TGG GTG TAG GCG TGG GTG TGT CCG CTC TTC GGA AAA
 D   H   L   T   T   H   I   R   T   H   T   G   E   K   P   F>

*FIG. 16A-1*

```
      200                210                220                230                240
       *                  *                  *                  *                  *
GCC   TGT   GAC   ATT   TGT   GGG   AGG   AAG   TTT   GCC   AGG   AGT   GAT   GAA   CGC   AAG
CGG   ACA   CTG   TAA   ACA   CCC   TCC   TTC   AAA   CGG   TCA   CTA   CTT   GCG   TTC
 A     C     D     I     C     G     R     K     F     A     R     S     D     E     R     K>

250                260                270                280
       *                  *                  *                  *
AGG   CAT   ACC   AAA   ATC   CAT   ACC   GGG   GAG   AAG   CCC   TAT   GCT   TGC   CCT   GTC
TCC   GTA   TGG   TTT   TAG   GTA   TGG   CCC   CTC   TTC   GGG   ATA   CGA   ACG   GGA   CAG
 R     H     T     K     I     H     T     G     E     K     P     Y     A     C     P     V>
                                            _____
                                             T  G  E  K  P 290                300                310                320                330
       *                  *                  *                  *                  *
GAG   TCC   TGC   GAT   CGC   CGC   TTT   AAA   AGA   GCG   TCG   GAT   GAG   CTC   ACC   CGC   CAT
CTC   AGG   ACG   CTA   GCG   GCG   AAA   TTT   TCT   CGC   AGC   CTA   CTC   GAA   TGG   GCG   GTA
 E     S     C     D     R     R     F     K     R     A     S     D     E     L     T     R     H>
```

*FIG. 16A-2*

```
                340               350               360               370               380
                 *                 *                 *                 *                 *
         ATC CGC ATC CAC ACA GGC CAG AAG CCC TTC CAG TGT CGA ATA TGC ATG
         TAG GCG TAG GTG TGT CCG GTC TTC GGG AAG GTC ACA GCT TAT ACG TAC
          I   R   I   H   T   G   Q   K   P   F   Q   C   R   I   C   M>

390               400               410               420               430
                 *                 *                 *                 *                 *
         CGT AAC TTC AGT CGT AGT GAC CAC CTT ACC ACC CAC ATC CGC ACC CAC
         GCA TTG AAG TCA GCA TCA CTG GTG GAA TGG TGG GTG TAG CCG TGG GTG
          R   N   F   S   R   S   D   H   L   T   T   H   I   R   T   H>

440               450               460               470               480
                 *                 *                 *                 *                 *
         ACA GGC GAG AAG CCT TTT GCC TGT GAC ATT TGT GGG AGG AAG TTT GCC
         TGT CCG CTC TTC GGA AAA CGG ACA CTG TAA ACA CCC TCC TTC AAA CGG
          T   G   E   K   P   F   A   C   D   I   C   G   R   K   F   A>

490               500               510               520
                 *                 *                 *                 *
         AGG AGT GAT GAA CGC AAG CAT ACC AAA ATC CAT TTA AGA CAG AAG
         TCC TCA CTA CTT GCG TTC GTA TGG TTT TAG GTA AAT TCT GTC TTC
          R   S   D   E   R   K   H   T   K   I   H   L   R   Q   K>

530               540
                 *                 *
         GAC TCT AGA ACT AGT
         CTG AGA TCT TGA TCA
          D   S   R   T   S>
```

ZINC FINGER PROTEIN DERIVATIVES AND METHODS THEREFOR

This application is a §371 application of PCTUS95/00829, filed Jan. 18, 1995, which is a continuation-in-part of application Ser. No. 08/312,604, filed Sep. 28, 1994 now abandoned, which is a continuation-in-part of application Ser. No. 08/183,119, filed Jan. 18, 1994 now abandoned.

BACKGROUND OF THE INVENTION

1. Field of the Invention

This invention relates generally to the field of regulation of gene expression and specifically to methods of modulating gene expression by utilizing polypeptides derived from zinc finger-nucleotide binding proteins.

2. Description of Related Art

Transcriptional regulation is primarily achieved by the sequence-specific binding of proteins to DNA and RNA. Of the known protein motifs involved in the sequence specific recognition of DNA, the zinc finger protein is unique in its modular nature. To date, zinc finger proteins have been identified which contain between 2 and 37 modules. More than two hundred proteins, many of them transcription factors, have been shown to possess zinc fingers domains. Zinc fingers connect transcription factors to their target genes mainly by binding to specific sequences of DNA base pairs—the "rungs" in the DNA "ladder".

Zinc finger modules are approximately 30 amino acid-long motifs found in a wide variety of transcription regulatory proteins in eukaryotic organisms. As the name implies, this nucleic acid binding protein domain is folded around a zinc ion. The zinc finger domain was first recognized in the transcription factor TFIIIA from Xenopus oocytes (Miller, et al., *EMBO*, 4:1609–1614, 1985; Brown, et al., *FEBS Lett.*, 186:271–274, 1985). This protein consists of nine imperfect repeats of a consensus sequence:

(Tyr, Phe)-X-Cys-$X_{2-4}$-Cys-$X_3$-Phe-$X_5$-Leu-$X_2$-His-$X_{3-4}$-His-$X_{2-6}$ (SEQ ID NO: 1)

where X is any amino acid.

Like TFIIIA, most zinc finger proteins have conserved cysteine and histidine residues that tetrahedrally-coordinate the single zinc atom in each finger domain. The structure of individual zinc finger peptides of this type (containing two cysteines and two histidines) such as those found in the yeast protein ADR1, the human male associated protein ZFY, the HIV enhancer protein and the Xenopus protein Xfin have been solved by high resolution NMR methods (Kochoyan, et al., *Biochemistry*, 30:3371–3386, 1991; Omichinski, et al., *Biochemistry*, 29:9324–9334, 1990; Lee, et al., *Science*, 245:635–637, 1989) and detailed models for the interaction of zinc fingers and DNA have been proposed (Berg, 1988; Berg, 1990; Churchill, et al., 1990). Moreover, the structure of a three finger polypeptide-DNA complex derived from the mouse immediate early protein zif268 (also known as Krox-24) has been solved by x-ray crystallography (Pavletich and Pabo, *Science*, 252:809–817, 1991). Each finger contains an antiparallel β-turn, a finger tip region and a short amphipathic α-helix which, in the case of zif268 zinc fingers, binds in the major groove of DNA. In addition, the conserved hydrophobic amino acids and zinc coordination by the cysteine and histidine residues stabilize the structure of the individual finger domain.

While the prototype zinc finger protein TFIIIA contains an array of nine zinc fingers which binds a 43 bp sequence within the 5S RNA genes, regulatory proteins of the zif268 class (Krox-20, Sp1, for example) contain only three zinc fingers within a much larger polypeptide. The three zinc fingers of zif268 each recognize a 3 bp subsite within a 9 bp recognition sequence. Most of the DNA contacts made by zif268 are with phosphates and with guanine residues on one DNA strand in the major groove of the DNA helix. In contrast, the mechanism of TFIIIA binding to DNA is more complex. The amino-terminal 3 zinc fingers recognize a 13 bp sequence and bind in the major groove. Similar to zif268, these fingers also make guanine contacts primarily on one strand of the DNA. Unlike the zif268 class of proteins, zinc fingers 4 and 6 of TFIIIA each bind either in or across the minor groove, bringing fingers 5 and 7 through 9 back into contact with the major groove (Clemens, et al., *Proc. Natl. Acad Sci. USA*, 89:10822–10826, 1992).

The crystal structure of zif268, indicates that specific histidine (non-zinc coordinating his residues) and arginine residues on the surface of the α-helix participate in DNA recognition. Specifically, the charged amino acids immediately preceding the α-helix and at helix positions 2, 3, and 6 (immediately preceding the conserved histidine) participate in hydrogen bonding to DNA guanines. Similar to finger 2 of the regulatory protein Krox-20 and fingers 1 and 3 of Sp1, finger 2 of TFIIIA contains histidine and arginine residues at these DNA contact positions; further, each of these zinc fingers minimally recognizes the sequence GGG. Finger swap experiments between transcription factor Sp1 and Krox-20 have confirmed the 3-bp zinc finger recognition code for this class of finger proteins (Nardelli, et al., *Nature*, 349:175–178, 1989). Mutagenesis experiments have also shown the importance of these amino acids in specifying DNA recognition. It would be desirable to ascertain a simple code which specifies zinc finger-nucleotide recognition. If such a code could be deciphered, then zinc finger polypeptides might be designed to bind any chosen DNA sequence. The complex of such a polypeptide and its recognition sequence might be utilized to modulate (up or down) the transcriptional activity of the gene containing this sequence.

Zinc finger proteins have also been reported which bind to RNA. Clemens, et al., (*Science*, 260:530, 1993) found that fingers 4 to 7 of TFIIIA contribute 95% of the free energy of TFIIIA binding to 5S rRNA, whereas fingers 1 to 3 make a similar contribution in binding the promoter of the 5S gene. Comparison of the two known 5S RNA binding proteins, TFIIIA and p43, reveals few homologies other than the consensus zinc ligands (C and H), hydrophobic amino acids and a threonine-tryptophan-threonine triplet motif in finger 6.

In order to redesign zinc fingers, new selective strategies must be developed and additional information on the structural basis of sequence-specific nucleotide recognition is required. Current protein engineering efforts utilize design strategies based on sequence and/or structural analogy. While such a strategy may be sufficient for the transfer of motifs, it limits the ability to produce novel nucleotide binding motifs not known in nature. Indeed, the redesign of zinc fingers utilizing an analogy based strategy has met with only modest success (Desjarlais and Berg, *Proteins*, 12:101, 1992).

As a consequence, there exists a need for new strategies for designing additional zinc fingers with specific recognition sites as well as novel zinc fingers for enhancing or repressing gene expression. The present invention fulfills this need.

SUMMARY OF THE INVENTION

The invention provides an isolated zinc finger-nucleotide binding polypeptide variant comprising at least two zinc finger modules that bind to a cellular nucleotide sequence and modulate the function of the cellular nucleotide sequence. The variant binds to either DNA or RNA and may enhance or suppress transcription from a promoter or from within a structural gene. The cellular nucleotide sequence may be a sequence which is a naturally occurring sequence in the cell, or it may be a viral-derived nucleotide sequence in the cell.

In another embodiment, the invention provides a pharmaceutical composition comprising a therapeutically effective amount of a zinc finger-nucleotide binding polypeptide derivative or a therapeutically effective amount of a nucleotide sequence which encodes a zinc finger-nucleotide binding polypeptide derivative, wherein the derivative binds to a cellular nucleotide sequence to modulate the function of the cellular nucleotide sequence, in combination with a pharmaceutically acceptable carrier.

In a further embodiment, the invention provides a method for inhibiting a cellular nucleotide sequence comprising a zinc finger-nucleotide binding motif, the method comprising contacting the motif with a zinc finger-nucleotide binding polypeptide derivative which binds the motif.

In yet a further embodiment, the invention provides a method for obtaining an isolated zinc finger-nucleotide binding polypeptide variant which binds to a cellular nucleotide sequence comprising identifying the amino acids in a zinc finger-nucleotide binding polypeptide that bind to a first cellular nucleotide sequence and modulate the function of the nucleotide sequence; creating an expression library encoding the polypeptide variant containing randomized substitution of the amino acids identified; expressing the library in a suitable host cell; and isolating a clone that produces a polypeptide variant that binds to a second cellular nucleotide sequence and modulates the function of the second nucleotide sequence. Preferably, the expression library encoding the polypeptide variant is a phage display library.

The invention also provides a method of treating a subject with a cell proliferative disorder, wherein the disorder is associated with the modulation of gene expression associated with a zinc finger-nucleotide binding motif, comprising contacting the zinc finger-nucleotide binding motif with an effective amount of a zinc finger-nucleotide binding polypeptide derivative that binds to the zinc finger-nucleotide binding motif to modulate activity of the gene.

Further, the invention provides a method for identifying a protein which modulates the function of a cellular nucleotide sequence and binds to a zinc finger-nucleotide binding motif comprising incubating components comprising a nucleotide sequence encoding the putative modulating protein operably linked to a first inducible promoter, and a reporter gene operably linked to a second inducible promoter and a zinc finger-nucleotide binding motif, wherein the incubating is carried out under conditions sufficient to allow the components to interact; and measuring the effect of the putative modulating protein on the expression of the reporter gene.

BRIEF DESCRIPTION OF THE DRAWINGS

FIG. 2A shows the amino acid sequence of the first three amino terminal zinc fingers of TFIIIA.

FIG. 2B shows the nucleotide sequence of the minimal binding site for zf 1–3.

FIGS. 7A and 7B show the nucleotide and deduced amino acid sequence for the zinc fingers of zif268 which were cloned in pComb 3.5.

FIG. 8 shows the amino acid sequence of the Zif268 protein and the hairpin DNA used for phage selection. (A) shows the conserved features of each zinc finger. (B) shows the hairpin DNA containing the 9-bp consensus binding site.

FIG. 9 is a table listing of the six randomized residues of finger 1, 2, and 3.

FIG. 11 is a table indicating $k_{on}$, association rate; $k_{off}$, dissociation rate; and $K_d$ equilibrium dissociation constant, for each protein.

FIGS. 13A and B show the nucleotide and amino acid sequence of Zif268-Jun (SEQ ID NOS: 33 and 34).

FIGS. 14A and B show the nucleotide and amino acid sequence of Zif268-Fos (SEQ ID NOS: 35 and 36).

FIGS. 15A and 15B show the nucleotide and amino acid sequence of the three finger construction of C7 zinc finger (SEQ ID NOS: 41 and 42).

FIGS. 16A and B show the nucleotide and amino acid sequence of Zif268—Zif268 linked by a TGEKP linker (SEQ ID NOS: 43 and 44).

DETAILED DESCRIPTION OF THE INVENTION

Figure 1:
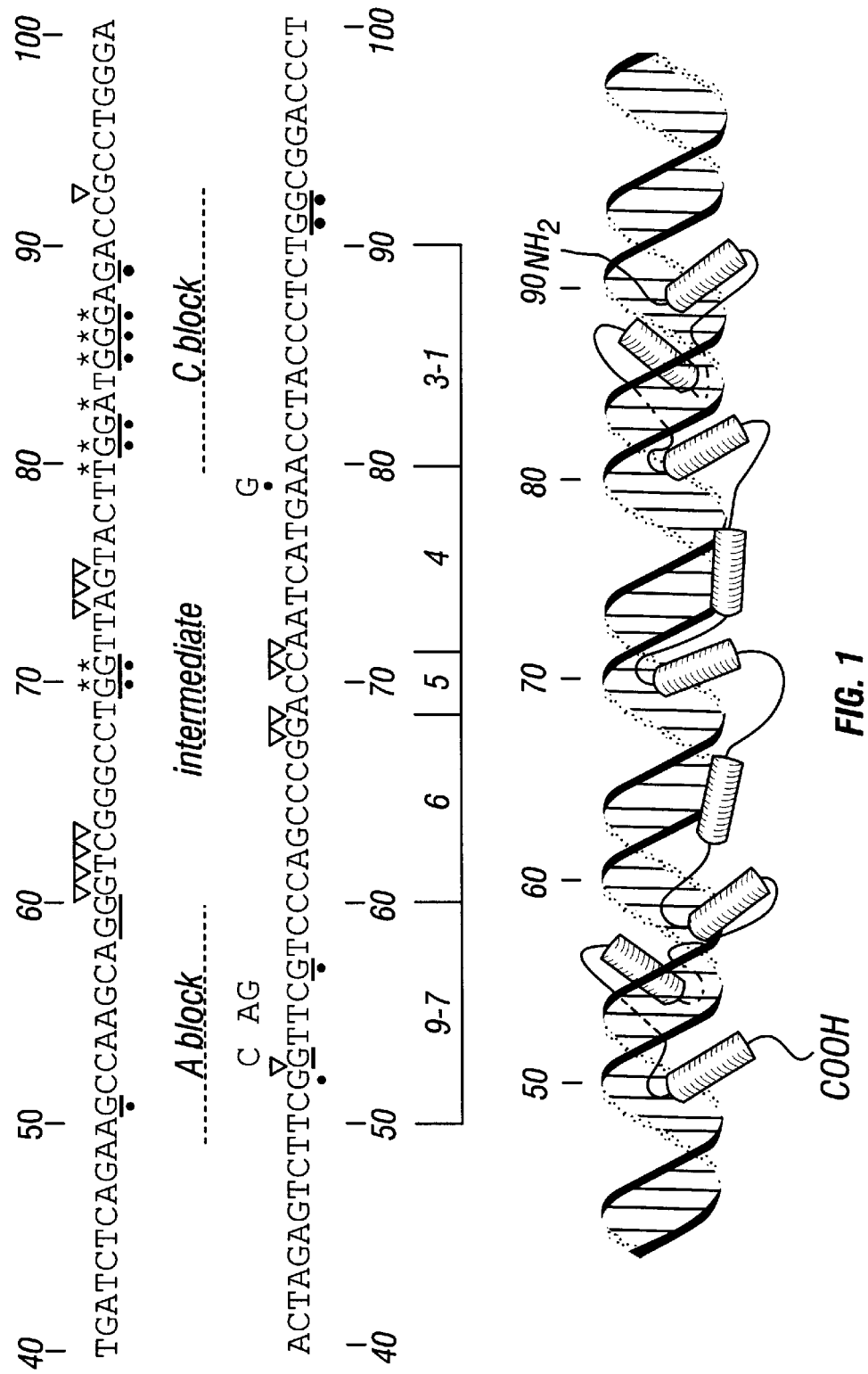
FIG. 1 shows a model for the interaction of the zinc fingers of TFIIIA with the internal promoter of the 5S RNA gene.

The present invention provides an isolated zinc finger-nucleotide binding polypeptide variant comprising at least two zinc finger modules that bind to a cellular nucleotide sequence and modulate the function of the cellular nucleotide sequence. The polypeptide variant may enhance or suppress transcription of a gene, and may bind to DNA or RNA. In addition, the invention provides a pharmaceutical composition comprising a therapeutically effective amount of a zinc finger-nucleotide binding polypeptide derivative or a therapeutically effective amount of a nucleotide sequence that encodes a zinc finger-nucleotide binding polypeptide derivative, wherein the derivative binds to a cellular nucleotide sequence to modulate the function of the cellular nucleotide sequence, in combination with a pharmaceutically acceptable carrier. The invention also provides a screening method for obtaining a zinc finger-nucleotide binding polypeptide variant which binds to a cellular or viral nucleotide sequence.

A zinc finger-nucleotide binding polypeptide "variant" refers to a polypeptide which is a mutagenized form of a zinc finger protein or one produced through recombination. A variant may be a hybrid which contains zinc finger domain (s) from one protein linked to zinc finger domain(s) of a second protein, for example. The domains may be wild type or mutagenized. A "derivative" includes a truncated form of a wild type zinc finger protein, which contains less than the original number of fingers in the wild type protein. A derivative also includes variant zinc finger polypeptides. Examples of zinc finger-nucleotide binding polypeptides from which a derivative or variant may be produced include TFIIIA and zif268.

As used herein a "zinc finger-nucleotide binding motif" refers to any two or three-dimensional feature of a nucleotide segment to which a zinc finger-nucleotide binding derivative polypeptide binds with specificity. Included within this definition are nucleotide sequences, generally of five nucleotides or less, as well as the three dimensional aspects of the DNA double helix, such as the major and minor grooves, the face of the helix, and the like. The motif is typically any sequence of suitable length to which the zinc finger polypeptide can bind. For example, a three finger polypeptide binds to a motif typically having about 9 to about 14 base pairs. Therefore, the invention provides zinc finger-nucleotide binding polypeptides of any specificity, and the zinc finger binding motif can be any sequence designed by the experiment or to which the zinc finger protein binds. The motif may be found in any DNA or RNA sequence, including regulatory sequences, exons, introns, or any non-coding sequence.

In the practice of this invention it is not necessary that the zinc finger-nucleotide binding motif be known in order to obtain a zinc-finger nucleotide binding variant polypeptide. Although zinc finger proteins have so far been identified only in eukaryotes, it is specifically contemplated within the scope of this invention that zinc finger-nucleotide binding motifs can be identified in non-eukaryotic DNA or RNA, especially in the native promoters of bacteria and viruses by the binding thereto of the genetically modified isolated constructs of this invention that preserve the well known structural characteristics of the zinc finger, but differ from zinc finger proteins found in nature by their method of production, as well as their amino acid sequences and three-dimensional structures.

The characteristic structure of the known wild type zinc finger proteins are made up of from two to as many as 37 modular tandem repeats, with each repeat forming a "finger" holding a zinc atom in tetrahedral coordination by means of a pair of conserved cysteines and a pair of conserved histidines. Generally each finger also contains conserved hydrophobic amino acids that interact to form a hydrophobic core that helps the module maintain its shape.

The zinc finger-nucleotide binding polypeptide variant of the invention comprises at least two zinc finger modules that bind to a cellular nucleotide sequence and modulate the function of the cellular nucleotide sequence. The term "cellular nucleotide sequence" refers to a nucleotide sequence which is present within the cell. It is not necessary that the sequence be a naturally occurring sequence of the cell. For example, a retroviral genome which is integrated within a host's cellular DNA, would be considered a "cellular nucleotide sequence". The cellular nucleotide sequence can be DNA or RNA and includes both introns and exons. The cell and/or cellular nucleotide sequence can be prokaryotic or eukaryotic, including a yeast, virus, or plant nucleotide sequence.

The term "modulate" refers to the suppression, enhancement or induction of a function. For example, the zinc finger-nucleotide binding polypeptide variant of the invention may modulate a promoter sequence by binding to a motif within the promoter, thereby enhancing or suppressing transcription of a gene operatively linked to the promoter cellular nucleotide sequence. Alternatively, modulation may include inhibition of transcription of a gene where the zinc finger-nucleotide binding polypeptide variant binds to the structural gene and blocks DNA dependent RNA polymerase from reading through the gene, thus inhibiting transcription of the gene. The structural gene may be a normal cellular gene or an oncogene, for example.

The promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product.

The promoter region may be a normal cellular promoter or, for example, an onco-promoter. An onco-promoter is generally a virus-derived promoter. For example, the long terminal repeat (LTR) of retroviruses is a promoter region which may be a target for a zinc finger binding polypeptide variant of the invention. Promoters from members of the Lentivirus group, which include such pathogens as human T-cell lymphotrophic virus (HTLV) 1 and 2, or human immunodeficiency virus (HIV) 1 or 2, are examples of viral promoter regions which may be targeted for transcriptional modulation by a zinc finger binding polypeptide of the invention.

The zinc finger-nucleotide binding polypeptide derivatives or variants of the invention include polypeptides that bind to a cellular nucleotide sequence such as DNA, RNA or both. A zinc finger-nucleotide binding polypeptide which binds to DNA, and specifically, the zinc finger domains which bind to DNA, can be readily identified by examination of the "linker" region between two zinc finger domains. The linker amino acid sequence TGEK(P) (SEQ ID NO: 32) is typically indicative of zinc finger domains which bind to a DNA sequence. Therefore, one can determine whether a particular zinc finger-nucleotide binding polypeptide preferably binds to DNA or RNA by examination of the linker amino acids.

In one embodiment, a method of the invention includes a method for inhibiting or suppressing the function of a cellular nucleotide sequence comprising a zinc finger-nucleotide binding motif which comprises contacting the zinc finger-nucleotide binding motif with an effective amount of a zinc finger-nucleotide binding polypeptide derivative that binds to the motif. In the case where the cellular nucleotide sequence is a promoter, the method includes inhibiting the transcriptional transactivation of a promoter containing a zinc finger-DNA binding motif. The term "inhibiting" refers to the suppression of the level of activation of transcription of a structural gene operably linked to a promoter containing a zinc finger-nucleotide binding motif, for example. In addition, the zinc finger-nucleotide binding polypeptide derivative may bind a motif within a structural gene or within an RNA sequence.

The term "effective amount" includes that amount which results in the deactivation of a previously activated promoter or that amount which results in the inactivation of a promoter containing a zinc finger-nucleotide binding motif, or that amount which blocks transcription of a structural gene or translation of RNA. The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or "contacting" the cellular nucleotide sequence containing the zinc finger-nucleotide binding protein motif, can be accomplished by one of the mechanisms described herein, such as by retroviral vectors or liposomes, or other methods well known in the art.

The zinc finger-nucleotide binding polypeptide derivative is derived or produced from a wild type zinc finger protein by truncation or expansion, or as a variant of the wild type-derived polypeptide by a process of site directed mutagenesis, or by a combination of the procedures.

The term "truncated" refers to a zinc finger-nucleotide binding polypeptide derivative that contains less than the full number of zinc fingers found in the native zinc finger binding protein or that has been deleted of non-desired sequences. For example, truncation of the zinc finger-nucleotide binding protein TFIIIA, which naturally contains nine zinc fingers, might be a polypeptide with only zinc fingers one through three. Expansion refers to a zinc finger polypeptide to which additional zinc finger modules have been added. For example, TFIIIA may be extended to 12 fingers by adding 3 zinc finger domains. In addition, a truncated zinc finger-nucleotide binding polypeptide may include zinc finger modules from more than one wild type polypeptide, thus resulting in a "hybrid" zinc finger-nucleotide binding polypeptide.

The term "mutagenized" refers to a zinc finger derived-nucleotide binding polypeptide that has been obtained by performing any of the known methods for accomplishing random or site-directed mutagenesis of the DNA encoding the protein. For instance. in TFIIIA, mutagenesis can be performed to replace nonconserved residues in one or more of the repeats of the consensus sequence. Truncated zinc finger-nucleotide binding proteins can also be mutagenized.

Examples of known zinc finger-nucleotide binding proteins that can be truncated, expanded, and/or mutagenized according to the present invention in order to inhibit the function of a cellular sequence containing a zinc finger-nucleotide binding motif includes TFIIIA and zif268. Other zinc finger-nucleotide binding proteins will be known to those of skill in the art.

The invention also provides a pharmaceutical composition comprising a therapeutically effective amount of a zinc finger-nucleotide binding polypeptide derivative or a therapeutically effective amount of a nucleotide sequence which encodes a zinc finger-nucleotide binding polypeptide derivative, wherein the derivative binds to a cellular nucleotide sequence to modulate the function of the cellular nucleotide sequence, in combination with a pharmaceutically acceptable carrier. Pharmaceutical compositions containing one or more of the different zinc finger-nucleotide binding derivatives described herein are useful in the therapeutic methods of the invention.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the composition.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

The invention includes a nucleotide sequence encoding a zinc finger-nucleotide binding polypeptide variant. DNA sequences encoding the zinc finger-nucleotide binding polypeptides of the invention, including native, truncated, and expanded polypeptides, can be obtained by several methods. For example, the DNA can be isolated using hybridization procedures which are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See for example, *Current Protocols in Molecular Biology*, Ausubel, et al. eds., 1989).

The development of specific DNA sequences encoding zinc finger-nucleotide binding proteins of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of mammalian polypeptides due to the presence of introns.

For obtaining zinc finger derived-DNA binding polypeptides, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression.

When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucleic Acid Research*, 11:2325, 1983).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. By using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981; Maniatis, et al., *Molecular Cloning: A Laboratory Manual*, Cold Spring Harbor Laboratory, 1982).

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

Since the DNA sequences of the invention encode essentially all or part of an zinc finger-nucleotide binding protein, it is now a routine matter to prepare, subclone, and express the truncated polypeptide fragments of DNA from this or corresponding DNA sequences. Alternatively, by utilizing the DNA fragments disclosed herein which define the zinc finger-nucleotide binding polypeptides of the invention it is possible, in conjunction with known techniques, to determine the DNA sequences encoding the entire zinc finger-nucleotide binding protein. Such techniques are described in U.S. Pat. Nos. 4,394,443 and 4,446,235 which are incorporated herein by reference.

A cDNA expression library, such as lambda gt11, can be screened indirectly for zinc finger-nucleotide binding protein or for the zinc finger derived polypeptide having at least one epitope, using antibodies specific for the zinc finger-nucleotide binding protein. Such antibodies can be either polyclonally or monoclonally derived and used to detect expression product indicative of the presence of zinc finger-nucleotide binding protein cDNA. Alternatively, binding of the derived polypeptides to DNA targets can be assayed by incorporated radiolabeled DNA into the target site and testing for retardation of electrophoretic mobility as compared with unbound target site.

A preferred vector used for identification of truncated and/or mutagenized zinc finger-nucleotide binding polypeptides is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface.

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei, et al. (*Nature,* 331:543–546, 1988).

The leader sequence of the pelB protein has previously been used as a secretion signal for fusion proteins (Better, et al., *Science,* 240:1041–1043, 1988; Sastry, et al., *Proc. Natl. Acad. Sci. USA,* 86:5728–5732, 1989; and Mullinax, et al., *Proc. Natl. Acad. Sci. USA,* 87:8095–8099, 1990). Amino acid residue sequences for other secretion signal polypeptide domains from *E. coli* useful in this invention can be found in Oliver, In Neidhard, F. C. (ed.), *Escherichia coli* and *Salmonella Typhimurium,* American Society for Microbiology, Washington, D.C., 1:56–69 (1987).

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane. In the phage f1, gene VIII coat protein's membrane spanning region comprises residue Trp-26 through Lys-40, and the cytoplasmic region comprises the carboxyterminal 11 residues from 41 to 52 (Ohkawa, et al., *J. Biol. Chem.*, 256:9951–9958, 1981). Thus, the amino acid residue sequence of a preferred membrane anchor domain is derived from the M13 filamentous phage gene VIII coat protein (also designated cp VIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein. For detailed descriptions of the structure of filamentous phage particles, their coat proteins and particle assembly, see the reviews by Rached, et al. (*Microbiol. Rev.*, 50:401–427 1986; and Model, et al., in "The Bacteriophages: Vol. 2", R. Calendar, ed. Plenum Publishing Co., pp. 375–456, 1988).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon (Shine, et al., Nature, 254:34, 1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors:

(i) The degree of complementarity between the SD sequence and 3' end of the 16S rRNA.

(ii) The spacing and possibly the RNA sequence lying between the SD sequence and the AUG (Roberts, et al., *Proc. Natl. Acad. Sci. USA*, 76:760, 1979a; Roberts, et al., *Proc. Natl. Acad. Sci. USA*, 76:5596, 1979b; Guarente, et al., Science, 209:1428, 1980; and Guarente, et al., *Cell*, 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.*, 35:365, 1981).

Leader sequences have been shown to influence translation dramatically (Roberts, et al., 1979 a, b supra).

(iii) The nucleotide sequence following the AUG, which affects ribosome binding (Taniguchi, et al., *J. Mol. Biol.*, 118:533, 1978).

The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook, et al., *Molecular Cloning: a Laboratory Manual*, 2nd edition, Cold Spring Harbor Laboratory Press, 1989).

The ColE1 and p15A replicons are particularly preferred for use in the present invention because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook, et al., supra, at pages 1.3–1.4).

In addition, those embodiments that include a prokaryotic replicon also include a gene whose expression confers a selective advantage, such as drug resistance, to a bacterial host transformed therewith. Typical bacterial drug resistance genes are those that confer resistance to ampicillin, tetracycline, neomycin/kanamycin or cholamphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.) and pBS (Stratagene, La Jolla, Calif.).

The vector comprises a first cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the zinc finger-derived polypeptide that is produced when an insert translatable DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

The zinc finger derived polypeptide expression vector also contains a second cassette for expressing a second receptor polypeptide. The second cassette includes a second translatable DNA sequence that encodes a secretion signal, as defined herein, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements. The second cassette is capable, upon insertion of a translatable DNA sequence (insert DNA), of expressing the second fusion polypeptide comprising a receptor of the secretion signal with a polypeptide coded by the insert DNA. For purposes of this invention, the second cassette sequences have been deleted.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

A sequence of nucleotides adapted for directional ligation. i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

In a preferred embodiment, a DNA expression vector is designed for convenient manipulation in the form of a filamentous phage particle encapsulating DNA encoding the zinc finger-nucleotide binding polypeptides of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles using screening technique well known in the art.

A filamentous phage origin of replication is a region of the phage genome, as is well known, that defines sites for initiation of replication, termination of replication and packaging of the replicative form produced by replication (see, for example, Rasched, et al., *Microbiol. Rev.*, 50:401–427, 1986; and Horiuchi, *J. Mol. Biol.*, 188:215–223, 1986).

A preferred filamentous phage origin of replication for use in the present invention is an M13, f1 or fd phage origin of replication (Short, et al. (*Nucl. Acids Res.*, 16:7583–7600, 1988). Preferred DNA expression vectors are the expression vectors modified pCOMB3 and specifically pCOMB3.5.

The production of a DNA sequence encoding a zinc finger-nucleotide binding polypeptide can be accomplished by oligonucleotide(s) which are primers for amplification of the genomic polynucleotide encoding an zinc finger-nucleotide binding polypeptide. These unique oligonucleotide primers can be produced based upon identification of the flanking regions contiguous with the polynucleotide encoding the zinc finger-nucleotide binding polypeptide. These oligonucleotide primers comprise sequences which are capable of hybridizing with the flanking nucleotide sequence encoding a zinc finger-nucleotide binding polypeptide and sequences complementary thereto and can be used to introduce point mutations into the amplification products.

The primers of the invention include oligonucleotides of sufficient length and appropriate sequence so as to provide specific initiation of polymerization on a significant number of nucleic acids in the polynucleotide encoding the zinc finger-nucleotide binding polypeptide. Specifically, the term "primer" as used herein refers to a sequence comprising two or more deoxyribonucleotides or ribonucleotides, preferably more than three, which sequence is capable of initiating synthesis of a primer extension product, which is substantially complementary to a zinc finger-nucleotide binding protein strand, but can also introduce mutations into the amplification products at selected residue sites. Experimental conditions conducive to synthesis include the presence of nucleoside triphosphates and an agent for polymerization and extension, such as DNA polymerase, and a suitable buffer, temperature and pH. The primer is preferably single stranded for maximum efficiency in amplification, but may be double stranded. If double stranded, the primer is first treated to separate the two strands before being used to prepare extension products. Preferably, the primer is an oligodeoxyribonucleotide. The primer must be sufficiently long to prime the synthesis of extension products in the presence of the inducing agent for polymerization and extension of the nucleotides. The exact length of primer will depend on many factors, including temperature, buffer, and nucleotide composition. The oligonucleotide primer typically contains 15–22 or more nucleotides, although it may contain fewer nucleotides. Alternatively, as is well known in the art, the mixture of nucleoside triphosphates can be biased to influence the formation of mutations to obtain a library of cDNAs encoding putative zinc finger-nucleotide binding polypeptides that can be screened in a functional assay for binding to a zinc finger-nucleotide binding motif, such as one in a promoter in which the binding inhibits transcriptional activation.

Primers of the invention are designed to be "substantially" complementary to a segment of each strand of polynucleotide encoding the zinc finger-nucleotide binding protein to be amplified. This means that the primers must be sufficiently complementary to hybridize with their respective strands under conditions which allow the agent for polymerization and nucleotide extension to act. In other words, the primers should have sufficient complementarity with the flanking sequences to hybridize therewith and permit amplification of the polynucleotide encoding the zinc finger-nucleotide binding protein. Preferably, the primers have exact complementarity with the flanking sequence strand.

Oligonucleotide primers of the invention are employed in the amplification process which is an enzymatic chain reaction that produces exponential quantities of polynucleotide encoding the zinc finger-nucleotide binding polypeptide relative to the number of reaction steps involved. Typically, one primer is complementary to the negative (−) strand of the polynucleotide encoding the zinc finger-nucleotide binding protein and the other is complementary to the positive (+) strand. Annealing the primers to denatured nucleic acid followed by extension with an enzyme, such as the large fragment of DNA Polymerase I (Klenow) and nucleotides, results in newly synthesized (+) and (−) strands containing the zinc finger-nucleotide binding protein sequence. Because these newly synthesized sequences are also templates, repeated cycles of denaturing, primer annealing, and extension results in exponential production of the sequence (i.e., the zinc finger-nucleotide binding protein polynucleotide sequence) defined by the primer. The product of the chain reaction is a discrete nucleic acid duplex with termini corresponding to the ends of the specific primers employed. Those of skill in the art will know of other amplification methodologies which can also be utilized to increase the copy number of target nucleic acid. These may include for example, ligation activated transcription (LAT), ligase chain reaction (LCR), and strand displacement activation (SDA), although PCR is the preferred method.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Methods for utilizing filamentous phage libraries to obtain mutations of peptide sequences are disclosed in U.S. Pat. No. 5,223,409 to Ladner et al., which is incorporated by reference herein in its entirety.

In one embodiment of the invention, randomized nucleotide substitutions can be performed on the DNA encoding one or more fingers of a known zinc finger protein to obtain a derived polypeptide that modifies gene expression upon binding to a site on the DNA containing the gene, such as a transcriptional control element. In addition to modifications in the amino acids making up the zinc finger, the zinc finger derived polypeptide can contain more or less than the full amount of fingers contained in the wild type protein from which it is derived.

While any method of site directed mutagenesis can be used to perform the mutagenesis, preferably the method used to randomize the segment of the zinc finger protein to be modified utilizes a pool of degenerate oligonucleotide primers containing a plurality of triplet codons having the formula NNS or NNK (and its complement NNM), wherein S is either G or C, K is either G or T, M is either C or A (the complement of NNK) and N can be A, C, G or T. In addition to the degenerate triplet codons, the degenerate oligonucleotide primers also contain at least one segment designed to hybridize to the DNA encoding the wild type zinc finger protein on at least one end, and are utilized in successive rounds of PCR amplification known in the art as overlap extension PCR so as to create a specified region of degeneracy bracketed by the non-degenerate regions of the primers in the primer pool.

The methods of overlap PCR as used to randomize specific regions of a cDNA are well known in the art and are further illustrated in Example 3 below. The degenerate products of the overlap PCR reactions are pooled and gel purified, preferably by size exclusion chromatography or gel electrophoresis, prior to ligation into a surface display phage expression vector to form a library for subsequent screening against a known or putative zinc finger-nucleotide binding motif.

The degenerate primers are utilized in successive rounds of PCR amplification known in the art as overlap extension PCR so as to create a library of cDNA sequences encoding putative zinc finger-derived DNA binding polypeptides. Usually the derived polypeptides contain a region of degeneracy corresponding to the region of the finger that binds to DNA (usually in the tip of the finger and in the α-helix region) bracketed by non-degenerate regions corresponding to the conserved regions of the finger necessary to maintain the three dimensional structure of the finger.

Any nucleic acid specimen, in purified or nonpurified form, can be utilized as the starting nucleic acid for the above procedures, provided it contains, or is suspected of containing, the specific nucleic acid sequence of an zinc finger-nucleotide binding protein of the invention. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., zinc finger-nucleotide binding protein sequence, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA or the DNA of any organism. For example, the source of DNA includes prokaryotes, eukaryotes, viruses and plants.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405–437, 1982).

If the nucleic acid containing the sequence to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be partially complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to a temperature that is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each zinc finger-nucleotide binding protein nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized zinc finger-nucleotide binding polypeptide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the zinc finger-nucleotide binding protein nucleic acid sequence to the extent necessary for detection. The amount of the specific nucleic acid sequence produced will accumulate in an exponential fashion.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988). Preferably, novel zinc finger derived-DNA binding polypeptides of the invention can be isolated utilizing the above techniques wherein the primers allow modification, such as substitution, of nucleotides such that unique zinc fingers are produced (See Examples for further detail).

In the present invention, the zinc finger-nucleotide binding polypeptide encoding nucleotide sequences may be inserted into a recombinant expression vector. The term "recombinant expression vector" refers to a plasmid, virus or other vehicle known in the art that has been manipulated by insertion or incorporation of zinc finger derived-nucleotide binding protein genetic sequences. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

DNA sequences encoding novel zinc finger-nucleotide binding polypeptides of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used.

A variety of host-expression vector systems may be utilized to express the zinc finger derived-nucleotide binding coding sequence. These include but are not limited to microorganisms such as bacteria transformed with recombinant bacteriophage DNA, plasmid DNA or cosmid DNA expression vectors containing a zinc finger derived-nucleotide binding polypeptide coding sequence; yeast transformed with recombinant yeast expression vectors containing the zinc finger-nucleotide binding coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a zinc finger derived-DNA binding coding sequence; insect cell systems infected with recombinant virus expression vectors (e.g., baculovirus) containing a zinc finger-nucleotide binding coding sequence; or animal cell systems infected with recombinant virus expression vectors (e.g., retroviruses, adenovirus, vaccinia virus) containing a zinc finger derived-nucleotide binding coding sequence, or transformed animal cell systems engineered for stable expression. In such cases where glycosylation may be important, expression systems that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter, et al., *Methods in Enzymology*, 153:516–544, 1987). For example, when cloning in bacterial systems, inducible promoters such as pL of bacteriophage λ, plac. ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted zinc finger-nucleotide binding polypeptide coding sequence.

In bacterial systems a number of expression vectors may be advantageously selected depending upon the use intended for the zinc finger derived nucleotide-binding polypeptide expressed. For example, when large quantities are to be produced, vectors which direct the expression of high levels of fusion protein products that are readily purified may be desirable. Those which are engineered to contain a cleavage site to aid in recovering the protein are preferred. Such vectors include but are not limited to the *E. coli* expression vector pUR278 (Ruther, et al., *EMBO J.*, 2:1791, 1983), in which the zinc finger-nucleotide binding protein coding sequence may be ligated into the vector in frame with the lac Z coding region so that a hybrid zinc finger-lac Z protein is produced; pIN vectors (Inouye & Inouye, *Nucleic Acids Res.* 13:3101–3109, 1985; Van Heeke & Schuster, *J. Biol. Chem.* 264:5503–5509, 1989); and the like.

In yeast, a number of vectors containing constitutive or inducible promoters may be used. For a review see, *Current Protocols in Molecular Biology*, Vol. 2, 1988, Ed. Ausubel, et al., Greene Publish. Assoc. & Wiley Interscience, Ch. 13; Grant, et al., 1987, *Expression and Secretion Vectors for Yeast*, in Methods in Enzymology, Eds. Wu & Grossman, 31987, Acad. Press, New York, Vol. 153, pp.516–544; Glover, 1986, DNA Cloning, Vol. II, IRL Press, Washington, D.C., Ch. 3; and Bitter, 1987, *Heterologous Gene Expression in Yeast*, Methods in Enzymology, Eds. Berger & Kimmel, Acad. Press, New York, Vol. 152, pp. 673–684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol.11, A Practical Approach, Ed. DM Glover, 1986, IRL Press, Washington, D.C.). Alternatively, vectors may be used which promote integration of foreign DNA sequences into the yeast chromosome.

In cases where plant expression vectors are used, the expression of a zinc finger-nucleotide binding polypeptide coding sequence may be driven by any of a number of promoters. For example, viral promoters such as the 35S RNA and 19S RNA promoters of CaMV (Brisson, et al., *Nature*, 310:511–514, 1984), or the coat protein promoter to TMV (Takamatsu, et al., *EMBO J.*, 6:307–311, 1987) may be used; alternatively, plant promoters such as the small subunit of RUBISCO (Coruzzi, et al., *EMBO J.* 3:1671–1680, 1984; Broglie, et al., *Science* 224:838–843, 1984); or heat shock promoters, e.g., soybean hsp17.5-E or hsp17.3-B (Gurley, et al., *Mol. Cell. Biol.*, 6:559–565, 1986) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, *Methods for Plant Molecular Biology*, Academic Press, New York, Section VIII, pp. 421–463, 1988; and Grierson & Corey, *Plant Molecular Biology*, 2d Ed., Blackie, London, Ch. 7–9, 1988.

An alternative expression system that can be used to express a protein of the invention is an insect system. In one such system, *Autographa californica* nuclear polyhedrosis virus (AcNPV) is used as a vector to express foreign genes. The virus grows in *Spodoptera frugiperda* cells. The zinc finger-nucleotide binding polypeptide coding sequence may be cloned into non-essential regions (*Spodoptera frugiperda* for example the polyhedrin gene) of the virus and placed under control of an AcNPV promoter (for example the polyhedrin promoter). Successful insertion of the zinc finger-nucleotide binding polypeptide coding sequence will result in inactivation of the polyhedrin gene and production of non-occluded recombinant virus (i.e., virus lacking the proteinaceous coat coded for by the polyhedrin gene). These recombinant viruses are then used to infect cells in which the inserted gene is expressed. (E.g., see Smith, et al., *J. Biol.* 46:584, 1983; Smith, U.S. Pat. No. 4,215,051).

Eukaryotic systems, and preferably mammalian expression systems, allow for proper post-translational modifications of expressed mammalian proteins to occur. Therefore, eukaryotic cells, such as mammalian cells that possess the cellular machinery for proper processing of the primary transcript, glycosylation, phosphorylation, and, advantageously secretion of the gene product, are the preferred host cells for the expression of a zinc finger derived-nucleotide binding polypeptide. Such host cell lines may include but are not limited to CHO, VERO, BHK, HeLa, COS, MDCK, −293, and W138.

Mammalian cell systems that utilize recombinant viruses or viral elements to direct expression may be engineered. For example, when using adenovirus expression vectors, the coding sequence of a zinc finger derived polypeptide may be ligated to an adenovirus transcription/translation control complex, e.g., the late promoter and tripartite leader sequence. This chimeric gene may then be inserted into the adenovirus genome by in vitro or in vivo recombination. Insertion in a non-essential region of the viral genome (e.g., region E1 or E3) will result in a recombinant virus that is viable and capable of expressing the zinc finger polypeptide in infected hosts (e.g., see Logan & Shenk, *Proc. Natl. Acad. Sci. USA* 81:3655–3659, 1984). Alternatively, the vaccinia virus 7.5K promoter may be used. (e.g., see, Mackett, et al., *Proc. Natl. Acad. Sci. USA*, 79:74 15–7419, 1982; Mackett, et al., *J. Virol.* 49:857–864, 1984; Panicali, et al., *Proc. Natl. Acad. Sci. USA*, 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the zinc finger-nucleotide binding protein gene in host cells (Cone & Mulligan, *Proc. Natl. Acad. Sci. USA* 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the a cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler, et al., *Cell* 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes, which can be employed in tk$^-$, hgprt$^-$ or aprt$^-$ cells respectively. Also, antimetabolite resistance-conferring genes can be used as the basis of selection; for example, the genes for dhfr, which confers resistance to methotrexate (Wigler, et al., *Natl. Acad. Sci. USA* 77:3567, 1980; O'Hare, et al., *Proc. Natl. Acad Sci. USA*, 78:1527, 1981); gpt, which confers resistance to mycophenolic acid (Mulligan & Berg, *Proc. Natl. Acad Sci. USA*, 78:2072, 1981; neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30:147, 1984). Recently, additional selectable genes have been described, namely trpB, which allows cells to utilize indole in place of tryptophan; hisD, which allows cells to utilize histinol in place of histidine (Hartman & Mulligan, *Proc. Natl. Acad Sci. USA*, 85:804, 1988); and ODC (ornithine decarboxylase) which confers resistance to the ornithine decarboxylase inhibitor. 2-(difluoromethyl)-DL-ornithine, DFMO (McConlogue L., In: *Current Communications in Molecular Biology*, Cold Spring Harbor Laboratory ed., 1987).

Isolation and purification of microbially expressed protein, or fragments thereof provided by the invention, may be carried out by conventional means including preparative chromatography and immunological separations involving monoclonal or polyclonal antibodies. Antibodies provided in the present invention are immunoreactive with the zinc finger-nucleotide binding protein of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The present invention also provides gene therapy for the treatment of cell proliferative disorders which are associated with a cellular nucleotide sequence containing a zinc finger-nucleotide binding motif. Such therapy would achieve its therapeutic effect by introduction of the zinc finger-nucleotide binding polypeptide polynucleotide, into cells of animals having the proliferative disorder. Delivery of a polynucleotide encoding a zinc finger-nucleotide binding protein can be achieved using a recombinant expression vector such as a chimeric virus or a colloidal dispersion system, for example.

The term "cell-proliferative disorder" denotes malignant as well as non-malignant cell populations which morphologically often appear to differ from the surrounding tissue. The cell-proliferative disorder may be a transcriptional disorder which results in an increase or a decrease in gene expression level. The cause of the disorder may be of cellular origin or viral origin. Gene therapy using a zinc finger-nucleotide binding polypeptide can be used to treat a virus-induced cell proliferative disorder in a human, for example, as well as in a plant. Treatment can be prophylactic in order to make a plant cell, for example, resistant to a virus, or therapeutic, in order to ameliorate an established infection in a cell, by preventing production of viral products.

A polynucleotide encoding the zinc finger-nucleotide binding polypeptide is useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine, and cancer of the esophagus. A polynucleotide encoding the zinc finger-nucleotide binding polypeptide is also useful in treating non-malignant cell-proliferative diseases such as psoriasis, pemphigus vulgaris, Behcet's syndrome, and lipid histiocytosis. Essentially, any disorder which is etiologically linked to the activation of a zinc finger-nucleotide binding motif containing promoter, structural gene, or RNA, would be considered susceptible to treatment with a polynucleotide encoding a derivative or variant zinc finger derived-nucleotide binding polypeptide.

Various viral vectors that can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector is made target specific. Retroviral vectors can be made target specific by inserting, for example, a polynucleotide encoding a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for polynucleotides encoding zinc finger derived-DNA binding polypeptides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting antibody-zinc finger-nucleotide binding protein-containing liposomes directly to the malignant tumor. Since the zinc finger-nucleotide binding protein gene product may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Liposomes may also be targeted to cells expressing receptors for hormones or other serum factors.

In another embodiment, the invention provides a method for obtaining an isolated zinc finger-nucleotide binding polypeptide variant which binds to a cellular nucleotide sequence comprising, first, identifying the amino acids in a zinc finger-nucleotide binding polypeptide that bind to a first cellular nucleotide sequence and modulate the function of the nucleotide sequence. Second, an expression library encoding the polypeptide variant containing randomized substitution of the amino acids identified in the first step is created. Third, the library is expressed in a suitable host cell, which will be apparent to those of skill in the art, and finally, a clone is isolated that produces a polypeptide variant that binds to a second cellular nucleotide sequence and modulates the function of the second nucleotide sequence. The invention also includes a zinc finger-nucleotide binding polypeptide variant produced by the method described above.

Preferably, a phage surface expression system, as described in the Examples of the present disclosure, is utilized as the library. The phage library is treated with a reducing reagent, such as dithiothreitol, which allows proper folding of the expression product on the phage surface. The library is made from polynucleotide sequences which encode a zinc finger-nucleotide binding polypeptide variant and which have been randomized, preferably by PCR using primers containing degenerate triplet codons at sequence locations corresponding to the determined amino acids in the first step of the method. The degenerate triplet codons have the formula NNS or NNK, wherein S is either G or C, K is either G or T, and N is independently selected from the group consisting of A, C, G, or T.

The modulation of the function of the cellular nucleotide sequence includes the enhancement or suppression of transcription of a gene operatively linked to the cellular nucleotide sequence, particularly when the nucleotide sequence is a promoter. The modulation also includes suppression of transcription of a nucleotide sequence which is within a structural gene or a virus DNA or RNA sequence. Modulation also includes inhibition of translation of a messenger RNA.

In addition, the invention discloses a method of treating a cell proliferative disorder, by the ex vivo introduction of a recombinant expression vector comprising the polynucleotide encoding a zinc finger-nucleotide binding polypeptide into a cell to modulate in a cell the function of a nucleotide sequence comprising a zinc finger-nucleotide binding motif. The cell proliferative disorder comprises those disorders as described above which are typically associated with transcription of a gene at reduced or increased levels. The method of the invention offers a technique for modulating such gene expression, whether at the promoter, structural gene, or RNA level. The method includes the removal of a tissue sample from a subject with the disorder, isolating hematopoietic or other cells from the tissue sample, and contacting isolated cells with a recombinant expression vector containing the DNA encoding zinc finger-nucleotide binding protein and, optionally, a target specific gene. Optionally, the cells can be treated with a growth factor, such as interleukin-2 for example, to stimulate cell growth, before reintroducing the cells into the subject. When reintroduced, the cells will specifically target the cell population from which they were originally isolated. In this way, the trans-repressing activity of the zinc finger-nucleotide binding polypeptide may be used to inhibit or suppress undesirable cell proliferation in a subject. In certain cases, modulation of the nucleotide sequence in a cell refers to suppression or enhancement of the transcription of a gene operatively linked to a cellular nucleotide sequence. Preferably, the subject is a human.

An alternative use for recombinant retroviral vectors comprises the introduction of polynucleotide sequences into the host by means of skin transplants of cells containing the virus. Long term expression of foreign genes in implants, using cells of fibroblast origin, may be achieved if a strong housekeeping gene promoter is used to drive transcription. For example, the dihydrofolate reductase (DHFR) gene promoter may be used. Cells such as fibroblasts, can be infected with virions containing a retroviral construct containing the gene of interest, for example a truncated and/or mutagenized zinc finger-nucleotide binding protein, together with a gene which allows for specific targeting, such as tumor-associated antigen (TAA), and a strong promoter. The infected cells can be embedded in a collagen matrix which can be grafted into the connective tissue of the dermis in the recipient subject. As the retrovirus proliferates and escapes the matrix it will specifically infect the target cell population. In this way the transplantation results in increased amounts of trans-repressing zinc finger-nucleotide binding polypeptide being produced in cells manifesting the cell proliferative disorder.

The novel zinc finger-nucleotide binding proteins of the invention, which modulate transcriptional activation or translation either at the promoter, structural gene, or RNA level, could be used in plant species as well. Transgenic plants would be produced such that the plant is resistant to particular bacterial or viral pathogens, for example. Methods for transferring and expressing nucleic acids in plants are well known in the art. (See for example, Hiatt, et al., U.S. Pat. No. 5,202,422, incorporated herein by reference.)

In a further embodiment, the invention provides a method for identifying a modulating polypeptide derived from a zinc finger-nucleotide binding polypeptide that binds to a zinc finger-nucleotide binding motif of interest comprising incubating components, comprising a nucleotide sequence encoding the putative modulating protein operably linked to a first inducible promoter and a reporter gene operably linked to a second inducible promoter and a zinc finger-nucleotide binding motif, wherein the incubating is carried out under conditions sufficient to allow the components to interact, and measuring the effect of the putative modulating protein on the expression of the reporter gene.

The term "modulating" envisions the inhibition or suppression of expression from a promoter containing a zinc finger-nucleotide binding motif when it is over-activated, or augmentation or enhancement of expression from such a promoter when it is under-activated. A first inducible promoter, such as the arabinose promoter, is operably linked to the nucleotide sequence encoding the putative modulating polypeptide. A second inducible promoter, such as the lactose promoter, is operably linked to a zinc finger derived- DNA binding motif followed by a reporter gene, such as β-galactosidase. Incubation of the components may be in vitro or in vivo. In vivo incubation may include prokaryotic or eukaryotic systems, such as *E. coli* or COS cells, respectively. Conditions which allow the assay to proceed include incubation in the presence of a substance, such as arabinose and lactose, which activate the first and second inducible promoters, respectively, thereby allowing expression of the nucleotide sequence encoding the putative trans-modulating protein nucleotide sequence. Whether or not the putative modulating protein binds to the zinc finger-nucleotide binding motif which is operably linked to the second inducible promoter, and affects its activity is measured by the expression of the reporter gene. For example, if the reporter gene was β-galactosidase, the presence of blue or white plaques would indicate whether the putative modulating protein enhances or inhibits, respectively, gene expression from the promoter. Other commonly used assays to assess the function from a promoter, including chloramphenicol acetyl transferase (CAT) assay, will be known to those of skill in the art. Both prokaryote and eukaryote systems can be utilized.

The invention is useful for the identification of a novel zinc finger-nucleotide binding polypeptide derivative or variant and the nucleotide sequence encoding the polypeptide. The method entails modification of the fingers of a wild type zinc finger protein so that they recognize a nucleotide, either DNA or RNA, sequence other than the sequence originally recognized by that protein. For example, it may be desirable to modify a known zinc finger protein to produce a new zinc finger-nucleotide binding polypeptide that recognizes, binds to, and inactivates the promoter region (LTR) of human immunodeficiency virus (HIV). Following identification of the protein, a truncated form of the protein is produced that represses transcription normally activated from that site. In HIV, the target site for a zinc finger-nucleotide binding motif within the promoter is CTG-TTG-TGT. The three fingers of zif268, for example, are mutagenized, as described in the examples. The fingers are mutagenized independently on the same protein (one by one), or independently or "piecewise" on three different zif268 molecules and religated after being mutagenized. Although one of these two methods is preferable, an alternative method would allow the three fingers to be mutagenized simultaneously. After mutagenesis, a phage display library is constructed and screened with the appropriate oligonucleotides which include the binding site of interest. If the fingers were mutagenized independently on the same protein, sequential libraries are constructed and panning performed after each library construction. For example, in zif268, a finger 3 library is constructed and panned with a finger 3 specific oligo; the positive clones from this screen are collected and utilized to make a finger 2 library (using finger 3 library DNA as a template); panning is performed with a finger 32 specific oligo; DNA is collected from positive clones and used as a template for finger 1 library construction; finally selection for a protein with 3 new fingers is performed with a finger 321 specific oligo. The method results in identification of a new zinc finger derived-DNA binding protein that recognizes, binds to, and represses transcription from the HIV promoter. Subsequent truncation, mutation, or expansion of various fingers of the new protein would result in a protein which represses transcription from the HIV promoter.

The invention provides, in EXAMPLES 7–13, an illustration of modification of Zif268 as described above. Therefore, in another embodiment, the invention provides a novel zinc-finger-nucleotide binding polypeptide variant comprising at least two zinc finger modules that bind to an HIV sequence and modulates the function of the HIV sequence. for example, the HIV promoter sequence.

The identification of novel zinc finger-nucleotide binding proteins allows modulation of gene expression from promoters to which these proteins bind. For example, when a cell proliferative disorder is associated with overactivation of a promoter which contains a zinc finger-nucleotide binding motif, such suppressive reagents as antisense polynucleotide sequence or binding antibody can be introduced to a cell, as an alternative to the addition of a zinc finger-nucleotide binding protein derivative. Alternatively, when a cell proliferative disorder is associated with underactivation of the promoter, a sense polynucleotide sequence (the DNA coding strand) or zinc finger-nucleotide binding polypeptide can be introduced into the cell.

Minor modifications of the primary amino acid sequence may result in proteins which have substantially equivalent activity compared to the zinc finger derived-binding protein described herein. Such modifications may be deliberate, as by site-directed mutagenesis, or may be spontaneous. All proteins produced by these modifications are included herein as long as zinc finger-nucleotide binding protein activity exists.

In another embodiment, zinc finger proteins of the invention can be manipulated to recognize and bind to extended target sequences. For example, zinc finger proteins containing from about 2 to 20 zinc fingers Zif(2) to Zif(20), and preferably from about 2 to 12 zinc fingers, may be fused to the leucine zipper domains of the Jun/Fos proteins, prototypical members of the bZIP family of proteins (O'Shea, et al., *Science,* 254:539, 1991). Alternatively, zinc finger proteins can be fused to other proteins which are capable of forming heterodimers and contain dimerization domains. Such proteins will be known to those of skill in the art.

The Jun/Fos leucine zippers are described for illustrative purposes and preferentially form heterodimers and allow for the recognition of 12 to 72 base pairs. Henceforth, Jun/Fos refer to the leucine zipper domains of these proteins. Zinc finger proteins are fused to Jun, and independently to Fos by methods commonly used in the art to link proteins. Following purification, the Zif-Jun and Zif-Fos constructs (SEQ ID NOS: 33, 34 and 35, 36 respectively), the proteins are mixed to spontaneously form a Zif-Jun/Zif-Fos heterodimer. Alternatively, coexpression of the genes encoding these proteins results in the formation of Zif-Jun/Zif-Fos heterodimers in vivo. Fusion of the heterodimer with an N-terminal nuclear localization signal allows for targeting of expression to the nucleus (Calderon, et al, *Cell,* 41:499, 1982). Activation domains may also be incorporated into one or each of the leucine zipper fusion constructs to produce activators of transcription (Sadowski, et al., *Gene,* 118:137, 1992). These dimeric constructs then allow for specific activation or repression of transcription. These heterodimeric Zif constructs are advantageous since they allow for recognition of palindromic sequences (if the fingers on both Jun and Fos recognize the same DNA/RNA sequence) or extended asymmetric sequences (if the fingers on Jun and Fos recognize different DNA/RNA sequences). For example the palindromic sequence

```
5' - GGC CCA CGC (N)  GCG TGG GCG - 3'
3' - GCG GGT GCG (N)x CGC ACC CGC - 5'
(SEQ ID NO: 37)
``` is recognized by the Zif268-Fos/Zif268 Jun dimer (x is any number). The spacing between subsites is determined by the site of fusion of Zif with the Jun or Fos zipper domains and the length of the linker between the Zif and zipper domains. Subsite spacing is determined by a binding site selection method as is common to those skilled in the art (Thiesen, et al., *Nucleic Acids Research,* 18:3203, 1990). Example of the recognition of an extended asymmetric sequence is shown by Zif(C7)$_6$-Jun/Zif-268-Fos dimer. This protein consists of 6 fingers of the C7 type (EXAMPLE 11) linked to Jun and three fingers of Zif268 linked to Fos, and recognizes the extended sequence:

```
5' - CGC CGC CGC CGC CGC CGC (N)  GCG TGG GCG - 3'
3' - GCG GCG GCG GCG GCG GCG (N)x CGC ACC CGC - 5'
(SEQ ID NO: 38)
```

Oxidative or hydrolytic cleavage of DNA or RNA with metal chelate complexes can be performed by methods known to those skilled in the art. In another embodiment, attachment of chelating groups to Zif proteins is preferably facilitated by the incorporation of a Cysteine (Cys) residue between the initial Methionine (Met) and the first Tyrosine (Tyr) of the protein. The Cys is then alkylated with chelators known to those skilled in the art, for example, EDTA derivatives as described (Sigman, *Biochemistry,* 29:9097, 1990). Alternatively the sequence Gly-Gly-His can be made as the most amino terminal residues since an amino terminus composed of the residues has been described to chelate Cu+2 (Mack, et al., *J. Am. Chem. Soc.,* 110:7572, 1988). Preferred metal ions include Cu+2, Ce+3 (Takasaki and Chin, *J. Am. Chem. Soc.* 116:1121, 1994) Zn+2, Cd+2, Pb+2, Fe+2 (Schnaith, et al., *Proc. Natl. Acad. Sci., USA,* 91:569, 1994), Fe+3, Ni+2, Ni+3, La+3, Eu+3 (Hall, et al., *Chemistry and Biology,* 1:185, 1994), Gd+3, Tb+3, Lu+3 Mn+2, Mg+2. Cleavage with chelated metals is generally performed in the presence of oxidizing agents such as $O_2$, hydrogen peroxide $H_2O_2$ and reducing agents such as thiols and ascorbate. The site and strand (+ or − site) of cleavage is determined empirically (Mack, et al., *J. Am. Chem. Soc.,* 110:7572, 1988) and is dependent on the position of the Cys between the Met and the Tyr preceding the first finger. In the protein Met (AA) Tyr-(Zif)$_{1-12}$, the chelate becomes Met-(AA)$_{x1}$ Cys-Chelate-(AA)$_{x2}$-Tyr-(Zif)$_{1-12}$, where AA=any amino acid and x=the number of amino acids. Dimeric zif constructs of the type Zif-Jun/Zif-Fos are preferred for cleavage at two sites within the target oligonucleotide or at a single long target site. In the case where double stranded cleavage is desired, both Jun and Fos containing proteins are labelled with chelators and cleavage is performed by methods known to those skilled in the art. In this case, a staggered double-stranded cut analogous to that produced by restriction enzymes is generated.

Following mutagenesis and selection of variants of the Zif268 protein in which the finger 1 specificity or affinity is modified, proteins carrying multiple copies of the finger may be constructed using the TGEKP linker sequence by methods known in the art. For example, the C7 finger may be constructed according to the scheme:

MKLLEPYACPVESCDRRFSKSADLKRHIRHTGEKP- (YACPVESCDRRFSKSADLKHIRIHTGEKP)$_{1-11}$, (SEQ ID NO: 39) where the sequence of the last linker is subject to change since it is at the terminus and not involved in linking two fingers together. This protein binds the designed target sequence GCG-GCG-GCG (SEQ ID NO: 32) in the oligonucleotide hairpin CCT-CGC-CGC-CGC-GGG-TTT-TCC-CGC-GCC-CCC GAG G (SEQ ID NO: 40) with an affinity of 9 nM, as compared to an affinity of 300 nM for an oligonucleotide encoding the GCG-TGG-GCG sequence (as determined by surface plasmon resonance studies). Fingers utilized need not be identical and may be mixed and matched to produce proteins which recognize a desired target sequence. These may also be utilized with leucine zippers (e.g., Fos/Jun) or other heterodimers to produce proteins with extended sequence recognition.

In addition to producing polymers of finger 1, the entire three finger Zif268 and modified versions therein may be fused using the consensus linker TGEKP to produce proteins with extended recognition sites. For example, the protein Zif268—Zif268 can be produced in which the natural protein has been fused to itself using the TGEKP linker. This protein now binds the sequence GCG-TGG-GCG-GCG-TGG-GCG. Therefore modifications within the three fingers of Zif268 or other zinc finger proteins known in the art may be fused together to form a protein which recognizes extended sequences. These new zinc proteins may also be used in combination with leucine zippers if desired.

The invention now being fully described, it will be apparent to one of ordinary skill in the art that various changes and modifications can be made without departing from the spirit or scope of the invention.

EXAMPLES

A recombinant polypeptide containing three of nine of the TFIIIA zinc fingers (Clemens, et al., *Proc. Nat'l Acad. Sci., USA,* 89:10822, 1992) has been generated by polymerase chain reaction (PCR) amplification from the cDNA for TFIIIA and expression in *E. coli.* The recombinant protein, termed zf1-3, was purified by ion exchange chromatography and its binding site within the 5S gene was determined by a combination of DNase I footprinting and binding to synthetic oligonucleotides (Liao, et al., *J. Mol. Biol.,* 223:857, 1992). The examples provide experiments which show that the binding of this polypeptide to its recognition sequence placed close to an active RNA polymerase promoter could inhibit the activity of that promoter in vitro. To provide such a test .system, a 26 bp oligonucleotide containing the 13 bp recognition sequence for zf1-3 was cloned into the polylinker region of plasmid pUC 19 near the promoter sequence for T7 RNA polymerase. The DNA binding activity of our preparation of recombinant zf1-3 was determined by gel mobility shift analysis with the oligonucleotide containing the binding site. In addition, in vitro transcription was performed with T7 RNA polymerase in the presence or absence of the same amounts of the zf1-3 polypeptide used in the DNA binding titration. For each DNA molecule bound by zf1-3, that DNA molecule is rendered inactive in transcription. In these examples, therefore, a zinc finger polypeptide has been produced which fully blocked the activity of a promoter by binding to a nearby target sequence.

Example 1

Sequence-specific Gene Targeting By Zinc Finger Proteins

A. From the crystal structure of zif268, it is clear that specific histidine (non-zinc coordinating his residues) and arginine residues on the surface of the α-helix, the finger tip, and at helix positions 2, 3, and 6 (immediately preceding the conserved histidine) participate in hydrogen bonding to DNA guanines. As the number of structures of zinc finger complexes continues to increase, it will be likely that different amino acids and different positions may participate in base specific recognition. FIG. 2 (panel A) shows the sequence of the three amino-terminal fingers of TFIIIA with basic amino acids at these positions underlined. Similar to finger 2 of the regulatory protein zif268 (Krox-20) and fingers 1 and 3 of Sp1, finger 2 of TFIIIA contains histidine and arginine residues at these DNA contact positions; further, each of these zinc fingers minimally recognizes the sequence GGG (FIG. 2, panel B) within the 5S gene promoter.

A recombinant polypeptide containing these three TFIIIA zinc fingers has been generated by polymerase chain reaction (PCR) amplification from the cDNA for TFIIIA and expression in *E. coli* (Clemens, et al., supra). An experiment was designed to determine whether the binding of this polypeptide to its recognition sequence, placed close to an active RNA polymerase promoter, would inhibit the activity of that promoter in vitro. The following experiments were done to provide such a test system. A 23 bp oligonucleotide (Liao, et al., 1992, supra) containing the 13 bp recognition sequence for zf1-3 was cloned into the polylinker region of plasmid pBluescript SK+ (Stratagene, La Jolla, Calif.), near the promoter sequence for T7 RNA polymerase. The parent plasmid was digested with the restriction enzyme EcoRV and, after dephosphorylation with calf intestinal alkaline phosphatase, the phosphorylated 23 bp oligonucleotide was inserted by ligation with T4 DNA ligase. The ligation product was used for transformation of DH5α *E. coli* cells. Clones harboring 23 bp inserts were identified by restriction digestion of miniprep DNA. The success of cloning was also verified by DNA sequence analysis.

Figure 3:
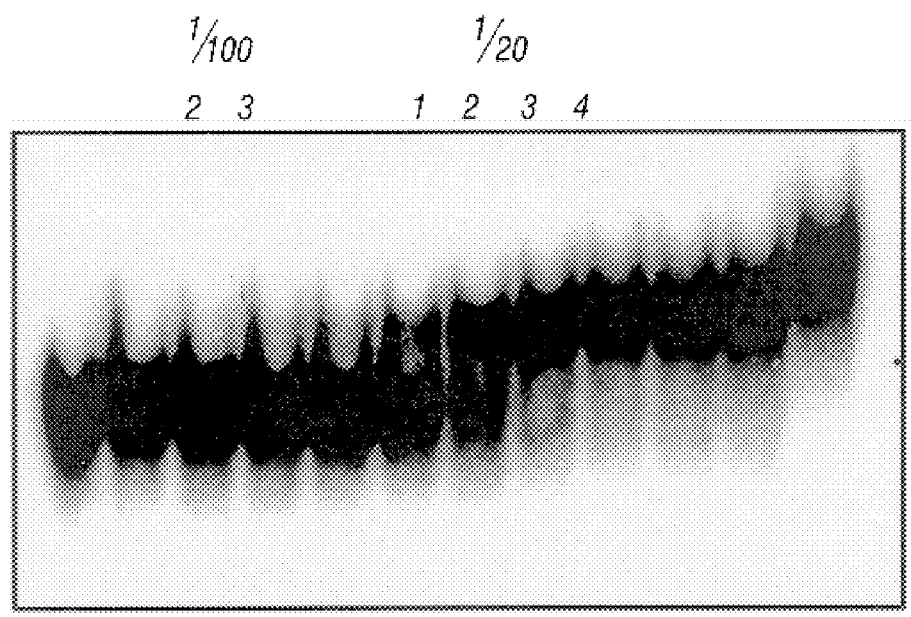
FIG. 3 shows a gel mobility shift assay for the binding of zf1-3 to a 23 bp $^{32}$P-labeled double stranded oligonucleotide.

The DNA binding activity of the preparation of recombinant zf1-3 was also determined by gel mobility shift analysis with a 56 bp radiolabeled EcoRI/XhoI restriction fragment derived from the cone containing the binding site for zf1-3 and with the radiolabeled 23 bp oligonucleotide. Gel shift assays were done as described (Liao, et al, supra, Fried, et al., *Nucl. Acids., Res.,* 9:6505, 1981). The result of the latter analysis is shown in FIG. 3. Binding reactions (20 μl) also contained 1 μg of unlabeled plasmid DNA harboring the same 23 bp sequence. In lanes 2–12, the indicated amounts of zf1-3 were also included in the reactions. After incubation at ambient temperature for 30 min, the samples were subjected to electrophoresis on a 6% nondenaturing polyacrylamide gel in 88 mM Tris-borate, pH 8.3, buffer. In each reaction, a trace amount of the radiolabeled oligonucleotide was used with a constant amount (1 μg) of plasmid DNA harboring the zf1-3 binding site. The reactions of lanes 2–12 contained increasing amounts of the zf1-3 polypeptide. The autoradiogram of the gel is shown. The results indicate that binding of zf1-3 to the radiolabeled DNA caused a retardation of electrophoretic mobility. The percentage of radiolabeled DNA molecules bound by zf1-3 also reflects the percentage of unlabeled plasmid DNA molecules bound.

Figure 4:
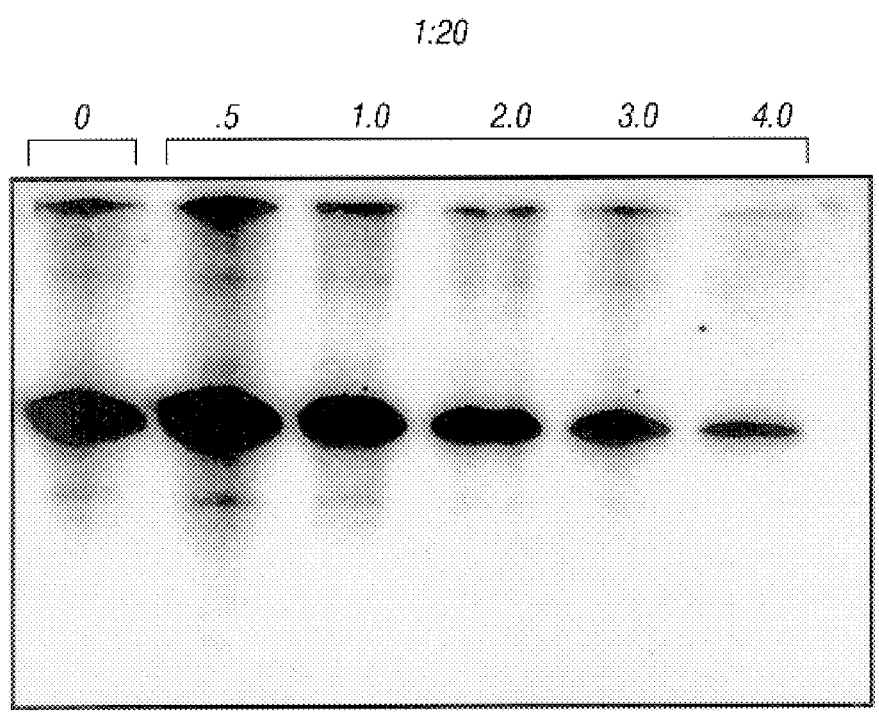
FIG. 4 shows an autoradiogram of in vitro transcription indicating that zf1-3 blocks transcription by T7 RNA polymerase.

In vitro transcription experiments were performed with T7 RNA polymerase in the presence or absence of the same amounts of the zf1-3 polypeptide used in the DNA binding titration with identical amounts of the plasmid DNA harboring the zf1-3 binding site. Each reaction contained, in a volume of 25 μl, 1 μg of PvuII-digested pBluescript SK+DNA containing the 23 bp binding site for zf1-3 inserted in the EcoRV site of the vector, 40 units of RNasin, 0.6 mM ATP+UTP+CTP, 20 μM GTP and 10 μCi of α-$^{32}$P-GTP and 10 units of T7 RNA polymerase (Stratagene). The reaction buffer was provided by Stratagene. After incubation at 37° C. for 1 hour, the products of transcription were purified by phenol extraction, concentrated by ethanol precipitation and analyzed on a denaturing polyacrylamide gel. T7 transcription was monitored by the incorporation of radioactive nucleotides into a run-off transcript. FIG. 4 shows an autoradiogram of a denaturing polyacrylamide gel analysis of the transcription products obtained. In this experiment, the plasmid DNA was cleaved with the restriction enzyme PvuII and the expected length of the run-off transcript was 245 bases. Addition of zf1-3 polypeptide to the reaction repressed transcription by T7 RNA polymerase.

Figure 5:
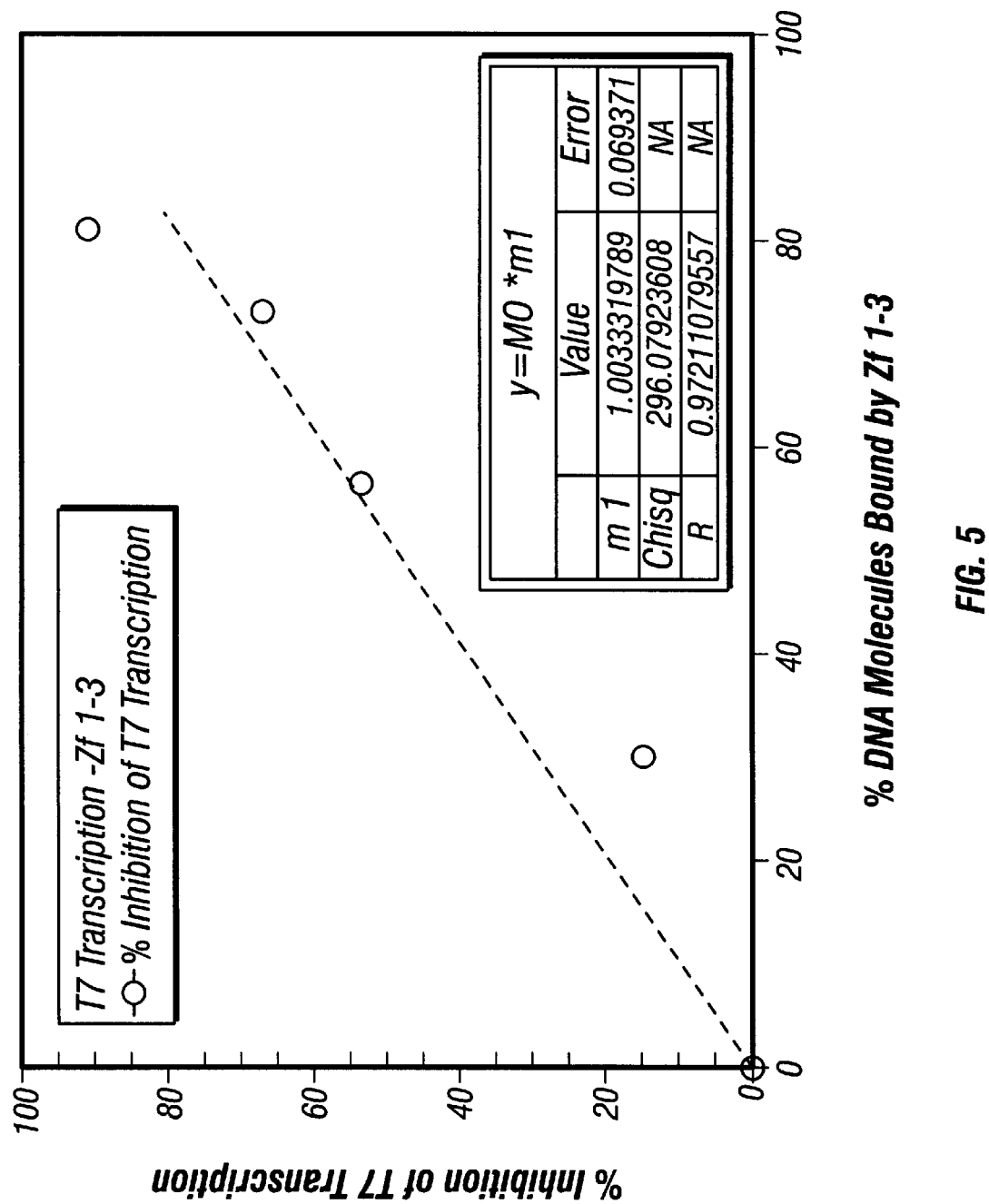
FIG. 5 shows binding of zf1-3 to its recognition sequence blocks transcription from a T7RNA polymerase promoter located nearby. A plot of percent of DNA molecules bound by zf1-3 in a gel mobility shift assay (x-axis) is plotted against percent inhibition of T7RNA polymerase transcription (y-axis).

FIG. 5 shows a graph in which the percentage of DNA molecules bound by zf1-3 in the DNA gel mobility shift assay (x-axis) versus the percentage of inhibition of T7 RNA polymerase transcription by the same amounts of zf1-3 (y-axis) has been plotted. Note that each data point corresponds to identical amounts of zf1-3 used in the two assays. The one-to-one correspondence of the two data sets is unequivocal. T7 transcription was monitored by the incorporation of radioactive nucleotides into a run-off transcript. Transcription was quantitated by gel electrophoresis, autoradiography and densitometry. Gel mobility shift assays were quantitated in a similar fashion. For each DNA molecule bound by zf1-3, that DNA molecule is rendered inactive in transcription. In this experiment, therefore, a zinc finger polypeptide has fully blocked the activity of a promoter by binding to a nearby target sequence.

Figure 6:
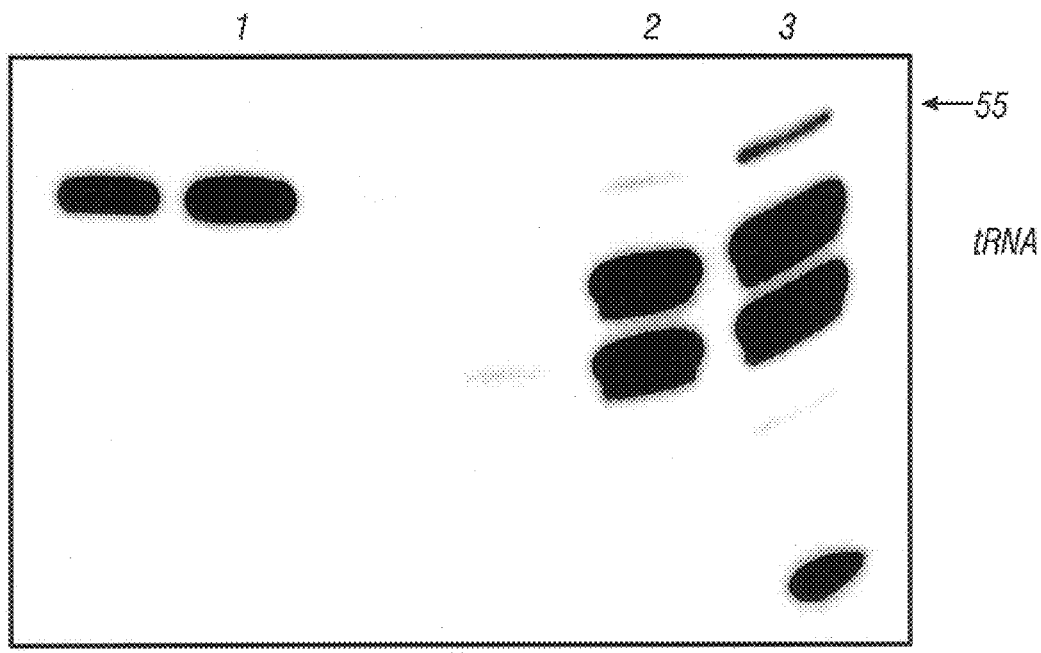
FIG. 6 is an autoradiogram showing zf1-3 blocks eukaryotic RNA polymerase III transcription in an in vitro transcription system derived from unfertilized Xenopus eggs.

B. Since the previous experiment was performed with a prokaryotic RNA polymerase, the following experiment was performed to determine whether the zinc finger polypeptide zf1-3 could also block the activity of a eukaryotic RNA polymerase. To test this, a transcription extract prepared from unfertilized Xenopus eggs (Hartl, et al., *J. Cell Biol.,* 120:613, 1993) and the Xenopus 5S RNA gene template was used. These extracts are highly active in transcription of 5S RNA and tRNAs by RNA polymerase III. As a test template, the 5S RNA gene which naturally contains the binding sites for TFIIIA and zf1-3, was used. Each reaction contained 10 μl of a high speed supernatant of the egg homogenate, 9 ng of TFIIIA, nucleoside triphosphates (ATP, UTP, CTP) at 0.6 mM and 10 μCi of α-$^{32}$P-GTP and GTP at 20 μM in a 25 μl reaction. All reactions contained 180 ng of a plasmid DNA harboring a single copy of the Xenopus somatic-type 5S RNA gene, and the reactions of lanes 2 and 3 also contained 300 ng of a Xenopus tRNAmet gene-containing plasmid. Prior to addition of the Xenopus egg extract and TFIIIA, 0.2 and 0.4 μg of zf1-3 were added to the reactions of lanes 2 and 3, respectively. The amount of zf1-3 used in the experiment of lane 2 was sufficient to bind all of the 5S gene-containing DNA in a separate binding reaction. After a 15 min. incubation to allow binding of zf1-3 to its recognition sequence, the other reaction components were added. After a 2 hour incubation, the products of transcription were purified by phenol extraction, concentrated by ethanol precipitation and analyzed on a denaturing polyacrylamide gel. The autoradiogram is shown in FIG. 6. FIG. 6 also shows the result of a controlled reaction in which no zinc finger protein was added (lane 1). As a control, lanes 2 and 3 also contained a tRNA gene template, which lacks the binding site for TFIIIA and zf1-3. 5S RNA transcription was repressed by zf1-3 while tRNA transcription was unaffected. These results demonstrate that zf1-3 blocks the assembly of a eukaryotic RNA polymerase III transcription complex and shows that this effect is specific for DNA molecules that harbor the binding site for the recombinant zinc finger protein derived from TFIIIA.

Three-dimensional solution structures have been determined for a protein containing the first three zinc fingers of TFIIIA using 2D, 3D, and 4D NMR methods. For this purpose, the protein was expressed and purified from *E. coli* and uniformly labeled with $^{13}$C and $^{15}$N. The NMR structure shows that the individual zinc fingers fold into the canonical finger structure with a small β-sheet packed against an α-helix. The fingers are not entirely independent in solution but there is evidence of subtle interactions between them. Using similar techniques the 3D structure of complex between zf 1–3 and a 13 bp oligonucleotide corresponding to its specific binding site on the 5S RNA gene is determined and used to provide essential information on the molecular basis for sequence-specific nucleotide recognition by the TFIIIA zinc fingers. This information is in turn used in designing new zinc finger derived-nucleotide binding proteins for regulating the preselected target genes. Similar NMR methods can be applied to determine the detailed structures of the complexes formed between designed zinc finger proteins and their target genes as part of a structure-based approach to refine target gene selectivity and enhance binding affinity.

Example 2

Isolation of Novel Zinc Finger-nucleotide Binding Proteins

In order to rapidly sort large libraries of zinc finger variants, a phage surface display system initially developed for antibody libraries (Barbas, et al., *METHODS*, 2:119, 1991) was used. To this end, pComb3 has been modified for zinc finger selection. The antibody light chain promoter and cloning sequences have been removed to produce a new vector, pComb3.5. The zif268 three finger protein has been modified by PCR and inserted into pComb3.5. The zinc fingers are functionally displayed on the phage as determined by solid phase assays which demonstrate that phage bind DNA in a sequence dependent fashion. Site-directed mutagenesis has been performed to insert an NsiI site between fingers 1 and 2 in order to facilitate library construction. Furthermore, zif268 is functional when fused to a decapeptide tag which allows its binding to be conveniently monitored. An initial library has been constructed using overlap PCR (Barbas, et al., *Proc. Natl. Acad. Sci., USA,* 89:4457, 1992) to create finger 3 variants where 6 residues on the amino terminal side of the α helix involved in recognition were varied with an NNK doping strategy to provide degeneracy. This third finger originally bound the GCG 3 bp subsite. Selection for binding to an AAA subsite revealed a consensus pattern appearing in the selected sequences.

The zif268 containing plasmid, pZif89 (Pavietich, et al., *Science* 252:809, 1991), was used as the source of zif268 DNA for modification of the zinc fingers. Briefly, pZif89 was cloned into the plasmid, pComb3.5, after amplification by PCR using the following primers:

ZF: 5'-ATG AAA CTG CTC GAG CCC TAT GCT TGC CCT
    GTC GAG-3'                    (SEQUENCE ID NO. 2)

ZR: 5'-GAG GAG GAG GAG ACT AGT GTC CTT CTG TCT
    TAA ATG GAT TTT GGT-3'(SEQUENCE ID NO. 3).

The PCR reaction was performed in a 100 μl reaction containing 1 μg of each of oligonucleotide primers ZF and ZR, dNTPs (dATP, dCTP, dGTP, dTTP), 1.5 mM MgCla Taq polymerase (5 units) 10 ng template pZif89, and 10 μl 10×PCR buffer (Perkin-Elmer Corp.). Thirty rounds of PCR amplification in a Perkin-Elmer Cetus 9600 Gene Amp PCR system thermocycler were performed. The amplification cycle consisted of denaturing at 94° C. for one minute, annealing at 54° C. for one minute, followed by extension at 72° C. for two minutes. The resultant PCR amplification products were gel purified as described below and digested with XhoI/SpeI and ligated into pComb3.5. pComb3.5 is a variant of pComb3 (Barbas, et al., *Proc. Natl. Acad. Sci., USA,* 88:7978, 1991) which has the light chain region, including its lacZ promoter, removed. Briefly, pComb3 was digested with NheI, klenow treated, digested with XbaI, and religated to form pComb3.5. Other similar vectors which could be used in place of pComb3.5, such as Surf Zap™ (Stratagene, La Jolla, Calif.), will be known to those of skill in the art.

The phagemid pComb3.5 containing zif268 was then used in PCR amplifications as described herein to introduce nucleotide substitutions into the zinc fingers of zif268, to produce novel zinc fingers which bind to specific recognition sequences and which enhance or repress transcription after binding to a given promoter sequence.

The methods of producing novel zinc fingers with particular sequence recognition specificity and regulation of gene expression capabilities involved the following steps:

1. A first zinc finger (e.g., Zinc finger 3 of zif268) was first randomized through the use of overlap PCR;
2. Amplification products from the overlap PCR containing randomized zinc fingers were ligated back into pComb3.5 to form a randomized library;
3. Following expression of bacteriophage coat protein III-anchored zinc finger from the library, the surface protein expressing phage were panned against specific zinc finger recognition sequences, resulting in the selection of several specific randomized zinc fingers; and
4. Following selection of sequence-specific zinc fingers, the corresponding phagemids were sequenced and the amino acid residue sequence was derived therefrom.

Example 3

Preparation of Randomized Zinc Fingers

To randomize the zinc fingers of zif268 in pComb3.5, described above, two separate PCR amplifications were performed for each finger as described herein, followed by a third overlap PCR amplification that resulted in the annealing of the two previous amplification products, followed by a third amplification. The nucleotide sequence of zinc finger of zif268 of template pComb3.5 is shown in FIG. 7 and is listed in SEQUENCE ID NO. 4. The nucleotide positions that were randomized in zinc finger 3 began at nucleotide position 217 and ended at position 237, excluding serine. The template zif268 sequence at that specified site encoded eight total amino acid residues in finger 3. This amino acid residue sequence of finger 3 in pComb3.5 which was to be modified is Arg-Ser-Asp-Glu-Arg-Lys-Arg-His (SEQUENCE ID NO. 5). The underlined amino acids represents those residues which were randomized.

A pool of oligonucleotides which included degenerate oligonucleotide primers, designated BZF3 and ZF36K and non-degenerate primers R3B and FTX3 having the nucleotide formula described below, (synthesized by Operon Technologies, Alameda, Calif.), were used for randomizing the zinc finger 3 of zif268 in pComb3.5. The six triplet codons for introducing randomized nucleotides included the repeating sequence NNM (complement of NNK), where M can be either G or C and N can be A, C, G or T.

The first PCR amplification resulted in the amplification of the 5' region of the zinc finger 3 fragment in the pComb3.5 phagemid vector clone. To amplify this region, the following primer pairs were used. The 5' oligonucleotide primer, FTX3, having the nucleotide sequence 5'-GCA ATT AAC CCT CAC TAA AGG G-3' (SEQUENCE ID NO. 6), hybridized to the noncoding strand of finger 3 corresponding to the region 5' (including the vector sequence) of and including the first two nucleotides of zif268. The 3' oligonucleotide primer, BZF3, having the nucleotide sequence 5'-GGC AAA CTT CCT CCC ACA AAT-3' (SEQUENCE ID NO. 7) hybridized to the coding strand of the finger 3 beginning at nucleotide 216 and ending at nucleotide 196.

The PCR reaction was performed in a 100 microliter (ul) reaction containing one microgram (ug) of each of oligonucleotide primers FTX3 and BZF3, 200 millimolar (mM) dNTP's (dATP, dCTP, dGTP, dTTP), 1.5 mM $MgCl_2$ Taq polymerase (5 units) (Perkin-Elmer Corp., Norwalk, Conn.), 10 nanograms (ng) of template pComb3.5 zif268, and 10 ul of 10× PCR buffer purchased commercially (Perkin-Elmer Corp.). Thirty rounds of PCR amplification in a Perkin-Elmer Cetus 9600 GeneAmp PCR System thermocycler were then performed. The amplification cycle consisted of denaturing at 94° C. for 30 seconds, annealing at 50° C. for 30 seconds, followed by extension at 72° C. for one minute. To obtain sufficient quantities of amplification product, 30 identical PCR reactions were performed.

The resultant PCR amplification products were then gel purified on a 1.5% agarose gel using standard electroelution techniques as described in "Molecular Cloning: A Laboratory Manual", Sambrook, et al., eds., Cold Spring Harbor, N.Y. (1989). Briefly, after gel electrophoresis of the digested PCR amplified zinc finger domain, the region of the gel containing the DNA fragments of predetermined size was excised, electroeluted into a dialysis membrane, ethanol precipitated and resuspended in buffer containing 10 mM Tris-HCl, pH 7.5 and 1 mM EDTA to a final concentration of 50 ng/ml.

The purified resultant PCR amplification products from the first reaction were then used in an overlap extension PCR reaction with the products of the second PCR reaction, both as described below, to recombine the two products into reconstructed zif268 containing randomized zinc fingers.

The second PCR reaction resulted in the amplification of the 3' end of zif268 finger 3 overlapping with the above products and extending 3' of finger 3. To amplify this region for randomizing the encoded eight amino acid residue sequence of finger 3, the following primer pairs were used. The 5' coding oligonucleotide primer pool was designated ZF36K and had the nucleotide sequence represented by the formula, 5'-ATT TGT GGG AGG AAG TTT GCC NNK AGT NNK NNK NNK NNK NNK CAT ACC AAA ATC CAT TTA-3' (SEQUENCE ID NO. 8) (nucleotides 196–255). The 3' noncoding primer, R3B, hybridized to the coding strand at the 3' end of gene III (gIII) having the sequence 5'-TTG ATA TTC ACA AAC GAA TGG-3' (SEQUENCE ID NO. 9). The region between the two specified ends of the primer pool is represented by a 15-mer NNK degeneracy. The second PCR reaction was performed on a second aliquot of pComb3.5 template in a 100 ul reaction as described above containing 1 ug of each of oligonucleotide primers as described. The resultant PCR products encoded a diverse population of randomized zif268 finger 3 regions of 8 amino acid residues in length. The products were then gel purified as described above. For the annealing reaction of the two PCR amplifications, 1 μg each of gel purified products from the first and second PCR reactions were then admixed and fused in the absence of primers for 35 cycles of PCR as described above. The resultant fusion product was then amplified with 1 ug each of FTX3 and R3B oligonucleotide primers as a primer pair in a final PCR reaction to form a complete zif268 fragment by overlap extension. The overlap PCR amplification was performed as described for other PCR amplifications above.

To obtain sufficient quantities of amplification product, 30 identical overlap PCR reactions were performed. The resulting fragments extended from 5' to 3' and had randomized finger 3 encoding 6 amino acid residues. The randomized zif268 amplification products of approximately 450 base pairs (bp) in length in each of the 30 reactions were first pooled and then gel purified as described above and cut with XhoI and SpeI, prior to their relegation into the pComb3.5 surface display phagemid expression vector to form a library for subsequent screening against zinc finger recognition sequence oligos for selection of a specific zinc finger. The ligation procedure in creating expression vector libraries and the subsequent expression of the zif268 randomized pComb3.5 clones was performed as described below in Example 4.

Nucleotide substitutions may be performed on additional zinc fingers as well. For example, in zif268, fingers 1 and 2 may also be modified so that additional binding sites may be identified. For modification of zinc finger 2, primers FTX3 (as described above) and ZFNsi-B, 5'-CAT GCA TAT TCG ACA CTG GAA-3' (SEQUENCE ID NO. 10) (nucleotides 100–120) are used for the first PCR reaction, and R3B (described above) and ZF2r6F (5'-CAG TGT CGA ATA TGC ATG CGT AAC TTC $(NNK)_6$ ACC ACC CAC ATC CGC ACC CAC-3') (SEQUENCE ID NO. 11) (nucleotides 103 to 168) are used for the second reaction. For modification of finger 1, RTX3 (above) and ZFI6rb (5'-CTG GCC TGT GTG GAT GCG GAT ATG $(MNN)_5$ CGA MNN AGA AAA GCG GCG ATC GCA GGA-3') (SEQUENCE ID NO. 12) (nucleotides 28 to 93) are used for the first reaction and ZFIF (5'-CAT ATC CGC ATC CAC ACA GGC CAG-3') (SEQUENCE ID NO. 13) (nucleotide 70 to 93) and R3B (above) are used in the second reaction. The overlap reaction utilizes FTX3 and R3B as described above for finger 3. Preferably, each finger is modified individually and sequentially on one protein molecule, as opposed to all three in one reaction. The nucleotide modifications of finger 1 of zif268 would include the underlined amino acids R S D E L T R H, (SEQUENCE ID NO. 14) which is encoded by nucleotides 49 to 72. The nucleotide modifications of finger 2 of zif268 would include S R S D H L (SEQUENCE ID NO. 15), which is encoded by nucleotides 130 to 147. (See FIG. 7).

Example 4

Preparation of Phagemid-displayed Sequences Having Randomized Zinc Fingers

The phagemid pComb3.5 containing zif268 sequences is a phagemid expression vector that provides for the expression of phage-displayed anchored proteins, as described above. The original pComb 3 expression vector was designed to allow for anchoring of expressed antibody proteins on the bacteriophage coat protein 3 for the cloning of combinatorial Fab libraries. XhoI and SpeI sites were provided for cloning complete PCR-amplified heavy chain (Fd) sequences consisting of the region beginning with framework 1 and extending through framework 4. Gene III of filamentous phage encodes this 406-residue minor phage coat protein, cpIII (cp3), which is expressed prior to extrusion in the phage assembly process on a bacterial membrane and accumulates on the inner membrane facing into the periplasm of E. coli.

In this system, the first cistron encodes a periplasmic secretion signal (pelB leader) operatively linked to the fusion protein, zif268-cpIII. The presence of the pelB leader facilitates the secretion of both the fusion protein containing randomized zinc finger from the bacterial cytoplasm into the periplasmic space.

By this process, the zif268-cpIII was delivered to the periplasmic space by the pelB leader sequence, which was subsequently cleaved. The randomized zinc finger was anchored in the membrane by the cpIII membrane anchor domain. The phagemid vector, designated pComb3.5, allowed for surface display of the zinc finger protein. The presence of the XhoI/SpeI sites allowed for the insertion of XhoI/SpeI digests of the randomized zif268 PCR products in the pComb3.5 vector. Thus, the ligation of the zif268 mutagenized nucleotide sequence prepared in Example 3 resulted in the in-frame ligation of a complete zif268 fragment consisting of PCR amplified finger 3. The cloning sites in the pComb3.5 expression vector were compatible with previously reported mouse and human PCR primers as described by Huse, et al., Science, 246:1275–1281 (1989) and Persson, et al., Proc. Natl. Acad. Sci., USA, 88:2432–2436 (1991). The nucleotide sequence of the pelB, a leader sequence for directing the expressed protein to the periplasmic space, was as reported by Huse, et al., supra.

The vector also contained a ribosome binding site as described by Shine, et al., Nature, 254:34, 1975). The sequence of the phagemid vector, pBluescript, which includes ColE1 and F1 origins and a beta-lactamase gene, has been previously described by Short, et al., Nuc. Acids Res., 16:7583–7600, (1988) and has the GenBank Accession Number 52330 for the complete sequence. Additional restriction sites, SalI, AccI, HincII, ClaI, HindIII, EcoRV, PstI and SmaI, located between the XhoI and SpeI sites of the empty vector were derived from a 51 base pair stuffer fragment of pBluescript as described by Short, et al., supra. A nucleotide sequence that encodes a flexible 5 amino acid residue tether sequence which lacks an ordered secondary structure was juxtaposed between the Fab and cp3 nucleotide domains so that interaction in the expressed fusion protein was minimized.

Thus, the resultant combinatorial vector, pComb3.5, consisted of a DNA molecule having a cassette to express a fusion protein, zif268/cp3. The vector also contained nucleotide residue sequences for the following operatively linked elements listed in a 5' to 3' direction: the cassette consisting of LacZ promoter/operator sequences; a NotI restriction site; a ribosome binding site; a pelB leader; a spacer region; a cloning region bordered by 5' XhoI and 3' SpeI restriction sites; the tether sequence; and the sequences encoding bacteriophage cp3 followed by a stop codon. A NheI restriction site located between the original two cassettes (for heavy and light chains); a second lacZ promoter/operator sequence followed by an expression control ribosome binding site; a pelB leader; a spacer region; a cloning region bordered by 5' SacI and a 3' XbaI restriction sites followed by expression control stop sequences and a second NotI restriction site were deleted from pComb3 to form pComb 3.5. Those of skill in the art will know of similar vectors that could be utilize in the method of the invention, such as the Surf Zap™ vector (Stratagene, La Jolla, Calif.).

In the above expression vector, the zif268/cp3 fusion protein is placed under the control of a lac promoter/operator sequence and directed to the periplasmic space by pelB leader sequences for functional assembly on the membrane. Inclusion of the phage F1 intergenic region in the vector allowed for the packaging of single-stranded phagemid with the aid of helper phage. The use of helper phage superinfection allowed for the expression of two forms of cp3. Consequently, normal phage morphogenesis was perturbed by competition between the Fd/cp3 fusion and the native cp3 of the helper phage for incorporation into the virion. The resulting packaged phagemid carried native cp3, which is necessary for infection, and the encoded fusion protein, which is displayed for selection. Fusion with the C-terminal domain was necessitated by the phagemid approach because fusion with the infective N-terminal domain would render the host cell resistant to infection.

The pComb3 and 3.5 expression vector described above forms the basic construct of the display phagemid expression vector used in this invention for the production of randomized zinc finger proteins.

Example 5

Phagemid Library Construction

In order to obtain expressed protein representing randomized zinc fingers, phagemid libraries were constructed. The libraries provided for surface expression of recombinant molecules where zinc fingers were randomized as described in Example 3.

For preparation of phagemid libraries for expressing the PCR products prepared in Example 3, the PCR products were first digested with XhoI and SpeI and separately ligated with a similarly digested original (i.e., not randomized) pComb3.5 phagemid expression vector. The XhoI and SpeI sites were present in the pComb3.5 vector as described above. The ligation resulted in operatively linking the zif268 to the vector, located 5' to the cp3 gene. Since the amplification products were inserted into the template pComb3.5 expression vector that originally had the heavy chain variable domain sequences, only the heavy chain domain cloning site was replaced leaving the rest of the pComb3.5 expression vector unchanged. Upon expression from the recombinant clones, the expressed proteins contained a randomized zinc finger.

Phagemid libraries for expressing each of the randomized zinc fingers of this invention were prepared in the following procedure. To form circularized vectors containing the PCR product insert, 640 ng of the digested PCR products were admixed with 2 ug of the linearized pComb3.5 phagemid vector and ligation was allowed to proceed overnight at room temperature using 10 units of BRL ligase (Gaithersburg, Md.) in BRL ligase buffer in a reaction volume of 150 ul. Five separate ligation reactions were performed to increase the size of the phage library having randomized zinc fingers. Following the ligation reactions, the circularized DNA was precipitated at −20° C. for 2 hours by the admixture of 2 ul of 20 mg/ml glycogen, 15 ul of 3 M sodium acetate at pH 5.2 and 300 ul of ethanol. DNA was then pelleted by microcentrifugation at 4° C. for 15 minutes. The DNA pellet was washed with cold 70% ethanol and dried under vacuum. The pellet was resuspended in 10 ul of water and transformed by electroporation into 300 ul of E. coli XL1-Blue cells to form a phage library.

After transformation, to isolate phage expressing mutagenized finger 3, phage were induced as described below for subsequent panning on a hairpin oligo having the following sequence (SEQUENCE ID NO. 16):

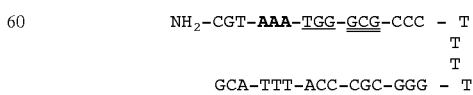

The bold sequence indicates the new zinc finger 3 binding site (formerly GCG), the underlined sequence represents the finger 2 site and the double underlining represents the finger 1 binding site.

Transformed *E. coli* were grown in 3 ml of SOC medium (SOC was prepared by admixture of 20 grams (g) bactotryptone, 5 g yeast extract and 0.5 g NaCl in 1 liter of water, adjusting the pH to 7.5 and admixing 20 ml of glucose just before use to induce the expression of the zif268-cpIII), were admixed and the culture was shaken at 220 rpm for 1 hour at 37° C. Following this incubation, 10 ml of SB (SB was prepared by admixing 30 g tryptone, 20 g yeast extract, and 10 g Mops buffer per liter with pH adjusted to 7) containing 20 ug/ml carbenicillin and 10 ug/ml tetracycline were admixed and the admixture was shaken at 300 rpm for an additional hour. This resultant admixture was admixed to 100 ml SB containing 50 ug/ml carbenicillin and 10 ug/ml tetracycline and shaken for 1 hour, after which helper phage VCSM13 ($10^{12}$ pfu) were admixed and the admixture was shaken for an additional 2 hours at 37° C. After this time, 70 ug/ml kanamycin was admixed and maintained at 30° C. overnight. The lower temperature resulted in better expression of zif268 on the surface of the phage. The supernatant was cleared by centrifugation (4000 rpm for 15 minutes in a JA10 rotor at 4° C.). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4° C.). Phage pellets were resuspended in 2 ml of buffer (5 mM DTT. 10 mM Tris-HCl, pH 7.56, 90 mM KCl, 90 mM $ZnCl_2$, 1 mM $MgCl_2$ and microcentrifuged for three minutes to pellet debris, transferred to fresh tubes and stored at –20° C. for subsequent screening as described below. DTT was added for refolding of the polypeptide on the phage surface.

For determining the titering colony forming units (cfu), phage (packaged phagemid) were diluted in SB and 1 ul was used to infect 50 ul of fresh ($A_{OD600}$=1) *E. coli* XL 1-Blue cells grown in SB containing 10 ug/ml tetracycline. Phage and cells were maintained at room temperature for 15 minutes and then directly plated on LB/carbenicillin plates. The randomized zinc finger 3 library consisted of $5 \times 10^7$ PFU total.

Multiple Pannings of the Phage Library

The phage library was panned against the hairpin oligo containing an altered binding site, as described above, on coated microtiter plates to select for novel zinc fingers.

The panning procedure used, comprised of several rounds of recognition and replication, was a modification of that originally described by Parmley and Smith (Parmley, et al., *Gene,* 73:305–318, 1988; Barbas, et al., 1991, supra.). Five rounds of panning were performed to enrich for sequence-specific binding clones. For this procedure, four wells of a microtiter plate (Costar 3690) were coated by drying overnight at 37° C. with 1 µg the oligo or the oligo was covalently attached to BSA with EDC/NHS activation to coat the plate (360 µg acetylated BSA (Boehringer Manheim), 577 µg oligo, 40 mM NHS, and 100 mM EDC were combined in 1.8 ml total volume and incubated overnight at room temperature. The plates were coated using 50 µl per plate and incubated at 4° C. overnight. The wells were washed twice with water and blocked by completely filling the well with 3% (w/v) BSA in PBS and maintaining the plate at 37° C. for one hour. After the blocking solution was shaken out, 50 ul of the phage suspension prepared above (typically $10^{12}$ pfu) were admixed to each well, and the plate was maintained for 2 hours at 37° C.

Phage were removed and the plate was washed once with water. Each well was then washed 10 times with TBS/Tween (50 mM Tris-HCl at pH 7.5, 150 mM NaCl, 0.5% Tween 20) over a period of 1 hour at room temperature where the washing consisted of pipetting up and down to wash the well, each time allowing the well to remain completely filled with TBS/Tween between washings. The plate was washed once more with distilled water and adherent phage were eluted by the addition of 50 ul of elution buffer (0.1 M HCl, adjusted to pH 2.2 with solid glycine, containing 1 mg/ml BSA) to each well followed by maintenance at room temperature for 10 minutes. The elution buffer was pipetted up and down several times, removed, and neutralized with 3 ul of 2 M Tris base per 50 ul of elution buffer used.

Eluted phage were used to infect 2 ml of fresh ($OD_{600}$=1) *E. coli* XL1-Blue cells for 15 minutes at room temperature, after which time 10 ml of SB containing 20 ug/ml carbenicillin and 10 ug/ml tetracycline was admixed. Aliquots of 20, 10, and 1/10 ul were removed from the culture for plating to determine the number of phage (packaged phagemids) that were eluted from the plate. The culture was shaken for 1 hour at 37° C., after which it was added to 100 ml of SB containing 50 ug/ml carbenicillin and 10 ug/ml tetracycline and shaken for 1 hour. Helper phage VCSM 13 ($10^{12}$ pfu) were then added and the culture was shaken for an additional 2 hours. After this time, 70 ug/ml kanamycin was added and the culture was incubated at 37° C. overnight. Phage preparation and further panning were repeated as described above.

Following each round of panning, the percentage yield of phage were determined, where % yield=(number of phage eluted/number of phage applied)×100. The initial phage input ratio was determined by titering on selective plates to be approximately $10^{11}$ cfu for each round of panning. The fmal phage output ratio was determined by infecting two ml of logarithmic phase XL1-Blue cells as described above and plating aliquots on selective plates. From this procedure, clones were selected from the Fab library for their ability to bind to the new binding sequence oligo. The selected clones had randomized zinc finger 3 domains.

The results from sequential panning of the randomized zinc finger 3 library revealed five binding sequences which recognized the new finger 3 site. The native site, GCG, was altered to AAA and the following sequences shown in Table 1 were identified to bind AAA.

TABLE 1

| BINDING SEQUENCE | |
|---|---|
| SEQUENCE ID NO. 17 | RSD ERK RH[1] |
| SEQUENCE ID NO. 18 | WSI PVL LH |
| SEQUENCE ID NO. 19 | WSL LPV LH |
| SEQUENCE ID NO. 20 | FSF LLP LH |
| SEQUENCE ID NO. 21 | LST WRG WH |
| SEQUENCE ID NO. 22 | TSI QLP YH |

[1]RSD ERK RH is the native Finger 3 binding sequence.

Example 6

Cotransformation Assay for Identification of Zinc Finger Activation of Promoter

In order to assess the functional properties of the new zinc fingers generated, an *E. coli* based in vivo system has been devised. This system utilizes two plasmids with the compatible replicons colE1 and p15. Cytosplamic expression of the zinc finger is provided by the arabinase promoter in the colE1 plasmid. The p15 replica containing plasmid contains a zinc finger binding site in place of the repressor binding site in a plasmid which expresses the a fragment of β galactosidase. The binding of the zinc finger to this site on the second plasmid shuts-off the production of β galactosidase and thus novel zinc fingers can be assessed in this in vivo assay for function using a convenient blue/white selection. For example, in the presence of arabinose and lactose, the zinc finger gene is expressed, the protein product binds to the zinc finger binding site and represses the lactose promoter. Therefore, no β-galactosidase is produced and white plaques would be present. This system which is compatible with respect to restriction sites with pComb3.5, will facilitate the rapid characterization of novel fingers. Furthermore, this approach could be extended to allow for the genetic selection of novel transcriptional regulators.

Another method of mutagenizing a wild type zinc finger-nucleotide binding protein includes segmental shuffling using a PCR technique which allows for the shuffling of gene segments between collections of genes. Preferably, the genes contain limited regions of homology, and at least 15 base pairs of contiguous sequence identity. Collections of zinc finger genes in the vector pComb3.5 are used as templates for the PCR technique. Four cycles of PCR are performed by denaturation, for example, for 1 min at 94° C. and annealling of 50° C. for 15 seconds. In separate experiments PCR is performed at 94° C., 1 min, 50° C., 30 sec; 94°, 1 min, 50°, 1 min; 94°, 1 min, 50°, 15 sec, 72°, 1 sec. All experiments use the same template (a 10 ng mixture). The experiment is performed such that under each condition two sets of reactions are performed. Each set has only a top or a bottom strand primer, which leads to the generation of single-stranded DNA's of different lengths. For example, FTX3, ZFIF and FZF3 primers may be used in a separate set to give single stranded products. The products from these reactions are then pooled and additional 5' and 3' terminal primers (e.g., FTX3 and R3B) are added and the mix is subjected to 35 additional rounds of PCR at 94° C., 1 min. 50°, 15 sec, 72°, 1 min 30 sec. The resultant mixture may then be cloned by Xho I/Spe I digestion. The new shuffled zinc fingers can be selected as described above, by panning a display of zinc fingers on any genetic package for selection of the optimal zinc-finger collections. This technique may be applied to any collection of genes which contain at least 15 bp of contiguous sequence identity. Primers may also be doped to a defined extent as described above using the NNK example, to introduce mutations in primer binding regions. Reaction times may be varied depending on length of template and number of primers used.

Example 7

Modification of Specificity of Zif268
Reagents, Strains, and Vectors

Restriction endonucleases were obtained from New England Biolabs or Boehringer Mannheim. T4 DNA ligase was the product of GIBCO BRL. Taq polymerase and Vent polymerase was purchased from Promega. Heparin-Sepharose CL-6B medium was from Pharmacia. Oligonucleotides were from Operon Technologies (Alameda, Calif.), or prepared on a Gene Assembler Plus (Pharmacia LKB) in the laboratory. pZif89 was a gift from Drs. Pavletich and Pabo (Pavietich, *Science,* 252:809–817, 1991). *Escherichia coli* BL21 (DE3) pLysS and plasmid pET3a was from Novagen, *Escherichia coli* XL1-Blue, phage VCSM13, the phagemid vector pComb3, and pAraHA are as described (Barbas III, et al., *Proc. Natl. Acad Sci. USA,* 88:7978–7982, 1991; Barbas III, et al., *Methods: A Companion to Methods in Enzymology,* 2:119–124, 1991).
Plasmid Construction Genes encoding wild-type zinc-finger proteins were placed under the control of the *Salmonella typhimurium* araB promoter by insertion of a DNA fragment amplified by the polymerase chain reaction (PCR) and containing the wild-type Zif268 gene of pzif89 (Pavletich, supra) with the addition of multiple restriction sites (XhoI/SacI and XbaI/SpeI). The resulting plasmid vector was subsequently used for subcloning the selected zinc-finger genes for immunoscreening. In this vector the zinc finger protein is expressed as a fusion with a hemagglutinin decapeptide tag at its C-terminus which may be detected with an anti-decapeptide monoclonal antibody (FIG. 8A) (Field, et al., *Mol. & Cell. Biol.* 8:2159–2165, 1988). The Zif268 protein is aligned to show the conserved features of each zinc finger. The α-helices and antiparallel β-sheets are indicated. Six amino-acid residues underlined in each finger sequence were randomized in library constructions. The C-terminal end of Zif268 protein was fused with a fragment containing a decapeptide tag. The position of fusion is indicated by an arrow.

The phagemid pComb3 was modified by digestion with NheI and XbaI to remove the antibody light chain fragment, filled with Klenow fragment, and the backbone was self-litigated, yielding plasmid pComb3.5. The Zif268 PCR fragment was inserted into pComb3.5 as above. To eliminate background problems in library construction a 1.1-kb non-functional stuffer was substituted for the wild-type Zif268 gene using SacI and XbaI. The resulting plasmid was digested by SacI and XbaI to excise the stuffer and the pComb3.5 backbone was gel-purified and served as the vector for library construction.
Zinc Finger Libraries Three zinc-finger libraries were constructed by PCR overlap extension using conditions previously described in Example 3. Briefly, for finger 1 library primer pairs A (5'-GTC CAT AAG ATT AGC GGA TCC-3') (SEQ. ID NO:29) and Zf16rb (SEQ. ID NO:12); (where N is A, T, G, or C, and M is A or C), and B (5'-GTG AGC GAG GAA GCG GAA GAG-3') (SEQ. ID NO:30) and Zf1f (SEQ. ID NO:13) were used to amplify fragments of Zif268 gene using plasmid pAra-Zif268 as a template. Two PCR fragments were mixed at equal molar ratio and the mixture was used as templates for overlap extension. The recombinant fragments were then PCR-amplified using primers A and B, and the resulting product was digested with SacI and XbaI and gel purified. For each ligation reaction, 280 ng of digested fragment was ligated with 1.8 μg of pComb3.5 vector at room temperature overnight. Twelve reactions were performed, and the DNA was ethanol-precipitated and electroporated into *E. coli* XL1-Blue. The libraries of finger 2 and 3 were constructed in a similar manner except that the PCR primers Zf16rb and ZF1F used in finger 1 library construction were replaced by Zfnsi-B (SEQ. ID NO:10) and ZF2r6F (SEQ. ID NO:11) (where K is G or T) for finger 2 library, and by BZF3 (SEQ. ID NO:7) and ZF36K (SEQ. ID NO:8) for finger 3 library. In the libraries, six amino-acid residues corresponding to the α-helix positions −1, 2, 3, 4, 5, 6 of finger 1 and 3, positions −2, −1, 1, 2, 3, 4 of finger 2 were randomized (FIG. 8A).
In Vitro Selection of Zinc Fingers A 34-nucleotide hairpin DNA containing either consensus or altered Zif268 binding site was used for zinc-finger selection (FIG. 8). The consensus binding site is denoted as Z268N (5'-CCT GCG TGG GCG CCC TTTT GGG CGC CCA CGC AGG-3') (SEQ. ID NO:31). The altered site for finger 1 is TGT (5'-CCT GCG TGG TGT CCC TTTT GGG ACA CAA CGC AGG-3') for finger 2 is TTG (5'-CCT GCG TTG GCG CCC TTTT GGG CGC CAA CGC AGG-3') and for finger 3 is CTG (5'-CCT CTG TGG GCG CCC TTTT GGG CGC CCA CAG AGG-3'). The oligonucleotide was synthesized with a primary n-hexyl amino group at its 5' end. A DNA-BSA conjugate was prepared by mixing 30 μM DNA with 3 μM acetylated BSA in a solution containing 100 mM 1-(3-dimethylaminopropyl)-3-ethylcarbodiimide hydrochloride (EDCI) and 40 mM N-hydroxysuccinimide (NHS) as room temperature for 5hours or overnight. Zif268 phage, $10^{12}$ colony forming units, in 50 μl zinc buffer (10 mM Tris-Cl, pH 7.5, 90 mM KCl, 1 mM $MgCl_2$, 90 μM $ZnCl_2$, 1 mM $MgCl_2$ and 5 mM DTT) containing 1% BSA was applied to a microtiter well precoated with 4.9 μg of DNA-BSA conjugate in 25 μl PBS buffer (10 mM potassium phosphate, 160 mM NaCl, pH 7.4) per well. After 2 hours of incubation at 37° C., the phage was removed and the plate washed once by TBS buffer (50 mM Tris-Cl and 150 mM NaCl, pH 7.5) containing 0.5% Tween for the first round of selection. The plate was washed 5 times for round 2, and 10 times for further rounds. Bound phage was extracted with elution buffer (0.1 M HCl, pH 2.2 (adjusted with glycine), and 1% BSA), and used in infect *E. coli* XL 1-Blue cells to produce phage for the subsequent selection.

Immunoscreening

Mutant zinc finger genes selected after five or six rounds of panning were subcloned into the pAraHA vector using XhoI and SpeI restriction sites. Typically, 20 clones were screened at a time. Cells were grown at 37° C. to late-log phase ($OD_{600}$ 0.8–1) in the 6 ml SB media (Barbas III, et al., supra) containing 30 μg/ml chloramphenicol. Expression of zinc-finger proteins was induced with addition of 1% of arabinose. Cells were harvested 3 to 12 hours following induction. Cell pellets were resuspended in 600 μl zinc buffer containing 0.5 mM phenylmethylsulfonyl fluoride (PMSF). Cells were lysed with 6-freeze-thaw cycles and the supernatant was clarified by centrifugation at 12,000 g for 5 minutes. A 50 μl-aliquot of cell supernatant was applied to a microtiter well precoated with 1.1 μg of DNA-BSA conjugate. After 1 hour at 37° C., the plate was washed 10 times with distilled water, and an alkaline phosphatase conjugated anti-decapeptide antibody was added to the plate. After 30 minutes at 37° C., the plate was washed 10 times and p-nitrophenylphosphate was added. The plate was then monitored with a microplate autoreader at 405 nm.

Overexpression and Purification of Zinc-finger Proteins

Zinc finger proteins were overproduced by using the pET expression system (Studier, et al., *Methods Enzymol.*, 185:60–89, 1990). The Zif268 gene was introduced following PCR into NdeI and BamHI digested vector pET3a. Subsequently, the Zif268 gene was replaced with a 680-bp nonfunctional stuffer fragment. The resulting pET plasmid containing the stuffer fragment was used for cloning other zinc-finger genes by replacing the stuffer with zinc-finger genes using SpeI and XhoI sites. The pET plasmids encoding zinc-finger genes were introduced into BL21(DE3) pLysS by chemical transformation. Cells were grown to mid-log phase ($OD_{600}$ 0.4–0.6) in SB medium containing 50 μg/ml carbenicillin and 30 μg/ml chloramphenicol. Protein expression was induced by addition of 0.7 mM IPTG to the medium. Typically, 500-ml cultures were harvested three hours after induction. Cell pellets were resuspended in the zinc buffer containing 1 mM PMSF and cell were lysed by sonication for 5 minutes at 0° C. Following addition of 6 mM $MgCl_2$, cell lysate were incubated with 10 μg/ml DNase I for 20 minutes on ice. Inclusion bodies containing zinc finger protein were collected by centrifugation at 25,000 g for 30 minutes and were resuspended and solubilized in 10 ml Zinc buffer containing 6M urea and 0.5 mM PMSF with gentle mixing for 3 to 12 hours at 4° C. The extract was clarified by centrifugation at 30,000 g for 30 minutes and filtered through a 0.2-μm low protein binding filter. Total protein extract was applied to a Heparin-Sepharose FPLC column (1.6×4.5 cm) equilibrated with zinc buffer. Proteins were eluted with a 0–0.7 M NaCl gradient. Fractions containing zinc-finger protein were identified by SDS-PAGE and pooled. Protein concentration was determined by the Bradford method using BSA (fraction V) as a standard (Bradford, *Anal. Biochem.*, 72:248–254, 1976). The yield of purified protein was from 7 to 19 mg/liter of cell culture. Protein was over 90% homogeneous as judged by SDS-PAGE.

Kinetic Analysis

The kinetic constants for the interactions between Zif268 peptides and their DNA targets were determined by surface plasmon resonance based analysis using the BIAcore instrument (Pharmacia) (Malmqvist, *Curr. Opinion in Immuno.*, 5:282–286, 1993). The surface of a sensor chip was activated with a mixture of EDCI and NHS for 15 minutes. Then 40 μl of affinity purified streptavidin (Pierce), 200 μg/ml in 10 mM sodium acetate (pH4.5), was injected at a rate of 5 μl/min. Typically, 5000–6000 resonance units of streptavidin were immobilized on the chip. Excess ester groups were quenched with 30 μl of 1M ethanolamine. Oligonucleotides were immobilized onto the chip by injection of 40 μl of biotinylated oligonucleotides (50 μg/ml) in 0.3 M of sodium chloride. Usually 1500–3000 resonance units of oligomers were immobilized. The association rate ($k_{on}$) was determined by studying the rate of binding of the protein to the surface at 5 different protein concentrations ranging from 10 to 200 μg/ml in the zinc buffer. The dissociation rate ($k_{off}$) was determined by increasing flow rate to 20 μl/min after association phase. The $k_{off}$ value is the average of three measurements. The $k_{on}$ and $k_{off}$ value were calculated using Biacore® kinetics evaluation software. The equilibrium dissociation constants were deduced from the rate constants.

Example 9

Phagemid Display of Modified Zinc Fingers

Library Design and Selection

Phage display of the Zif268 protein was achieved by modification of the phagemid display system pComb3 as described in Examples 2–6. The Zif268 sequence from pzif89 was tailored by PCR for insertion between the XhoI and SpeI sites of pComb3.5. As described above in Example 4, insertion at these sites results in the fusion of Zif268 with the carboxyl terminal segment of the filamentous phage coat protein III, pIII, gene. A single panning experiment which consists of incubating the phage displaying the zinc finger protein with the target DNA sequence immobilized on a microtiter well followed by washing, elution, and titering of eluted phage was utilized to examine the functional properties of the protein displayed on the phage surface.

In control experiments, phage displaying Zif268 were examined in a panning experiment to bind a target sequence bearing its consensus binding site or the binding site of the first three fingers of TFIIIA. These experiments showed that Zif268 displaying phage bound the appropriate target DNA sequence 9-fold over the TFIIIA sequence or BSA and demonstrated that sequence specific binding of the finger complex is maintained during phage display. A 4-fold reduction in phage binding was noted when $Zn^{+2}$ and DTT were not included in the binding buffer. Two reports verify that Zif268 can be displayed on the phage surface (Rebar, et al., *Science*, 263:671–673, 1994; Jamieson, et al., *Biochem.*, 33:5689–5695, 1994).

In a similar experiment, the first three fingers of TFIIIA were displayed on the surface of phage and also shown to retain specific binding activity. Immobilization of DNA was facilitated by the design of stable hairpin sequence which present the duplex DNA target of the fingers within a single oligonucleotide which was amino labeled (FIG. 8B) (Antao, et al., *Nucleic Acids Research,* 19:5901–5905, 1991). The hairpin DNA containing the 9-bp consensus binding site (5'-GCGTGGGCG-3', as enclosed) of wild-type Zif268 was used for affinity selection of phage-displayed zinc finger proteins. In addition, the 3-bp subsites (boxed) of consensus HIV-1 DNA sequence were substituted for wild-type Zif268 3-bp subsites for affinity selection.

The amino linker allowed for covalent coupling of the hairpin sequence to acetylated BSA which was then immobilized for selection experiments by adsorption to polystyrene microtiter wells. Biotinylated hairpin sequences worked equally well for selection following immobilization to streptavidin coated plate.

Libraries of each of the three fingers of Zif268 were independently constructed using the previously described overlap PCR mutagenesis strategy (Barbas III, et al. *Proc. Natl. Acad. Sci. USA,* 89:4457–4461, 1992 and EXAMPLES 2–6). Randomization was limited to six positions due to constraints in the size of libraries which can be routinely constructed (Barbas III, *Curr. Opinion in Biotech,* 4:526–530, 1993). Zinc finger protein recognition of DNA involves an antiparallel arrangement of protein in the major groove of DNA, i.e., the amino terminal region in involved in 3' contacts with the target sequence whereas the carboxyl terminal region is involved in 5' contacts (FIG. 8B). Within a given finger/DNA subsite complex, contacts remain antiparallel where in finger 1 of Zif268, guanidinium groups of Arg at helix positions –1 and 6 hydrogen bond with the 3' and 5' guanines, respectively of the GCG target sequence. Contact with the central base in a triplet subsite sequence by the side chain of the helix position 3 residue is observed in finger 2 of Zif268, fingers 4 and 5 of GLI, and fingers 1 and 2 of TTK. Within the three reported crystal structures of zinc-finger/DNA complexes direct base contact has been observed between the side-chains of residues –1 to 6 with the exception of 4 (Pavletich, supra; Pavletich, *Science,* 261:1701–1707, 1993; Fairall, et al., *Nature* 366:483–487, 1993).

Based on these observations, residues corresponding to the helix positions –1, 2, 3, 4, 5, and 6 were randomized in the finger 1 and 3 libraries. The Ser of position 1 was conserved in these experiments since it is well conserved at this position in zinc finger sequences in general and completely conserved in Zif268 (Jacobs, *EMBO J.,* 11:4507–4517, 1992). In the finger 2 library, helix positions –2, –1, 1, 2 3, and 4 were randomized to explore a different mutagenesis strategy where the –2 position is examined since both Zif268 and GLI structures reveal this position to be involved in phosphate contacts and since it will have a context effect on the rest of the domain. Residues 5 and 6 were fixed since the target sequence TTG retained the 5' thymidine of the wild type TGG site. Introduction of ligated DNA by electroporation resulted in the construction of libraries consisting of $2\times10^9$, $6\times10^8$, and $7\times10^8$ independent transforrnants for finger libraries 1, 2, and 3, respectively. Each library results in the display of the mutagenized finger in the context of the two remaining fingers of wild-type sequences.

Example 10

Sequence Analysis of Selected Fingers

In order to examine the potential of modifying zinc-fingers to bind defined targets and to examine their potential in gene therapy, a conserved sequence within the HIV-1 genome was chosen as a target sequence. The 5' leader sequence of HIV-1 HXB2 clone at positions 106 to 121 relative to the transcriptional initiation start site represents one of several conserved regions within HIV-1 genomes (Yu, et al., *Proc. Natl. Acad Sci. USA,* 90:6340–6344, 1993); Myers, et al., 1992). For these experiments, the 9 base pair region, 113 to 121, shown in FIG. 8B, was targeted.

Following selection for binding the native consensus or HIV-1 target sequences, functional zinc fingers were rapidly identified with an immunoscreening assay. Expression of the selected proteins in a pAraHA derivative resulted in the fusion of the mutant Zif268 proteins with a peptide tag sequence recognized by a monoclonal antibody (FIG. 8A). Binding was determined in an ELISA format using crude cell lysates. A qualitative assessment of specificity can also be achieved with this methodology which is sensitive to at least 4-fold differences in affinity. Several positive clones from each selection were sequenced and are shown in FIG. 9. The six randomized residues of finger 1 and 3 are at positions –1, 2, 3, 4, 5, and 6 in the α-helical region, and at –2, –1, 1, 2, 3, and 4 in finger 2 (FIG. 9). The three nucleotides denote the binding site used for affinity selection of each finger. Proteins studied in detail are indicated with a clone designation.

Finger 1 selection with the consensus binding site GCG revealed a strong selection for Lys at position –1 and Arg at position 6. Covariation between positions –1 and 2 is observed in three clones which contain Lys and Cys at these positions respectively. Clone C7 was preferentially enriched in the selection based on its occurrence in 3 of the 12 clones sequenced. Selection against the HIV-1 target sequence in this region, TGT, revealed a diversity of sequences with a selection for residues with hydrogen-bonding side chains in position –1 and a modest selection for Gln at position 3. Finger 2 selection against the consensus TGG subsite showed a selection for an aromatic residue at –1 whereas selection against the HIV-1 target TTG demonstrated a selection for a basic residue at this position. The preference for Ser at position 3 may be relevant in the recognition of thymidine. Contact of thymine with Ser has been observed in the GLI and TTK structures (Pavletich, supra, Fairall, et al., supra). Other modest selections towards consensus residues can be observed within the table. Selections were performed utilizing a supE strain of *E. coli* which resulted in the reading of the amber codon TAG as a Gln during translation. Of the 51 sequences presented in FIG. 9, 14 clones possessed a single amber codon. No clones possessed more than one amber codon. Selection for suppression of the amber stop codon in supE stains has been noted in other DNA binding protein libraries and likely improves the quality of the library since this residue is frequently used as a contact residue in DNA binding proteins (Huang, et al., *Proc. Natl. Acad. Sci. USA,* 91:3969–3973, 1994). Selection for fingers containing free cysteines is also noted and likely reflects the experimental protocol. Phage were incubated in a buffer containing $Zn^{+2}$ and DTT to maximize the number of phage bearing properly folded fingers. Selection against free cysteines, presumably due to aggregation or improper folding, has been noted previously in phage display libraries of other proteins (Lowman, et al., *J. Mol. Biol.,* 234:564–578, 1993).

Figure 10:
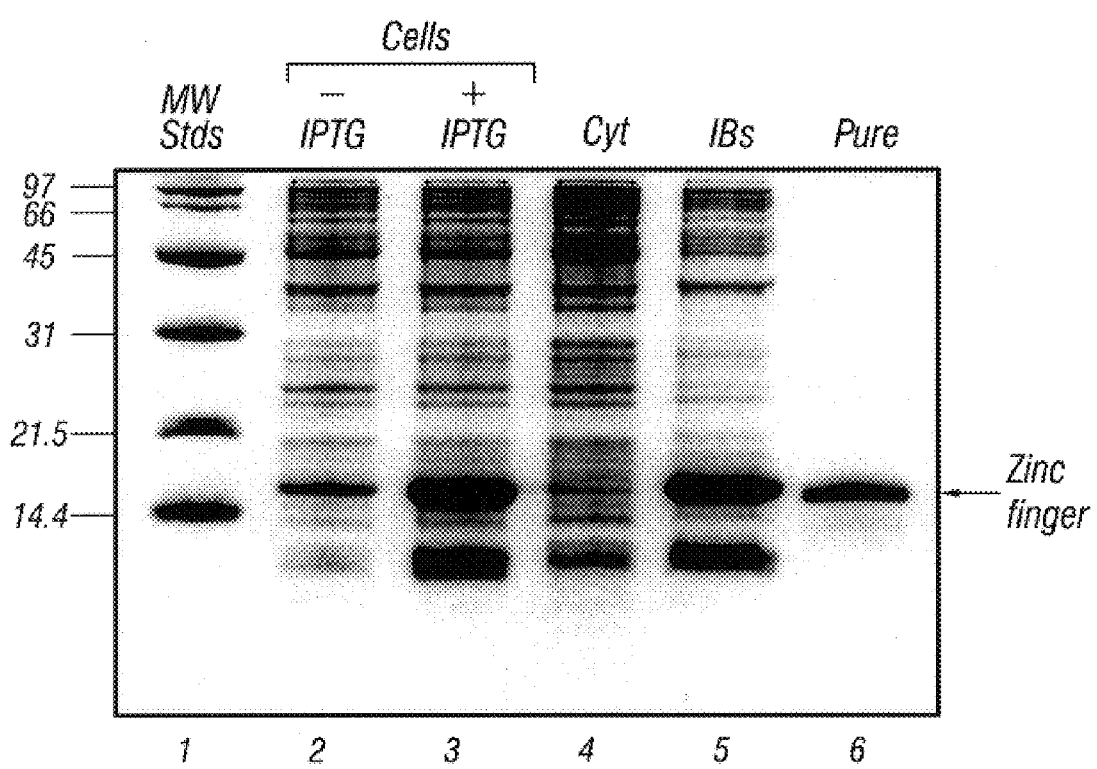
FIG. 10 shows an SDS-PAGE of Zif268 variant A14 before IPTG induction (lane 2); after IPTG induction (lane 3); cytoplasmic fraction after removal of inclusion bodies (lane 4); inclusion bodies containing zinc finger peptide (lane 5); and mutant Zif268 (lane 6). Lane 1 is MW Standards (kD).

For further characterization, high level expression of zinc finger proteins was achieved using the T7 promoter (FIG. 10) (Studier, et al., supra). In FIG. 10, proteins were separated by 15% SDS-PAGE and stained with Coomassie brilliant blue. Lane 1: molecular weight standards (kDa).

Lane 2: cell extract before IPTG induction. Lane 3: cell extract after IPTG induction. Lane 4: cytoplasmic fraction after removal of inclusion bodies by centrifugation. Lane 5: inclusion bodies containing zinc finger peptide. Lane 6: mutant Zif268 peptide purified by Heparin-Sepharose FPLC. Clones C10, F8, and G3 each possessed an amber codon which was converted to CAG to encode for Gln prior to expression in this system.

Example 11

Characterization of Affinity and Specificity

In order to gain insight into the mechanism of altered specificity or affinity, the kinetics of binding was determined using real-time changes in surface plasmon resonance (SPR) (Malmqvist, supra). The kinetic constants and calculated equilibrium dissociation constants of 11 proteins are shown in FIG. 11. Each zinc finger protein studied is indicated by a clone designation (for its sequence, see FIG. 9). The target DNA site used for selection of each finger is indicated in bold face. The consensus binding site for the wild type protein is also shown in bold. The non-hairpin duplex DNA (underlined) was prepared by annealing two single-stranded DNAs. The $k_{on}$, association rate; $k_{off}$, dissociation rate; $K_d$, equilibrium dissociation constant for each protein is given.

The calculated equilibrium dissociation constants for Zif268 binding to its consensus sequence in the form of the designed hairpin or a linear duplex lacking the tetrathymidine loop are virtually identical suggesting that the conformation of the duplex sequence recognized by the protein is not perturbed in conformation within the hairpin. The value of 6.5 nM for Zif268 binding to its consensus is in the range of 0.5 to 6 nM reported using electrophoretic mobility shift assays for this protein binding to its consensus sequence within oligonucleotides of different length and sequence (Pavletich, supra; Rebar, supra; Jamieson, et al, supra).

Figure 12:
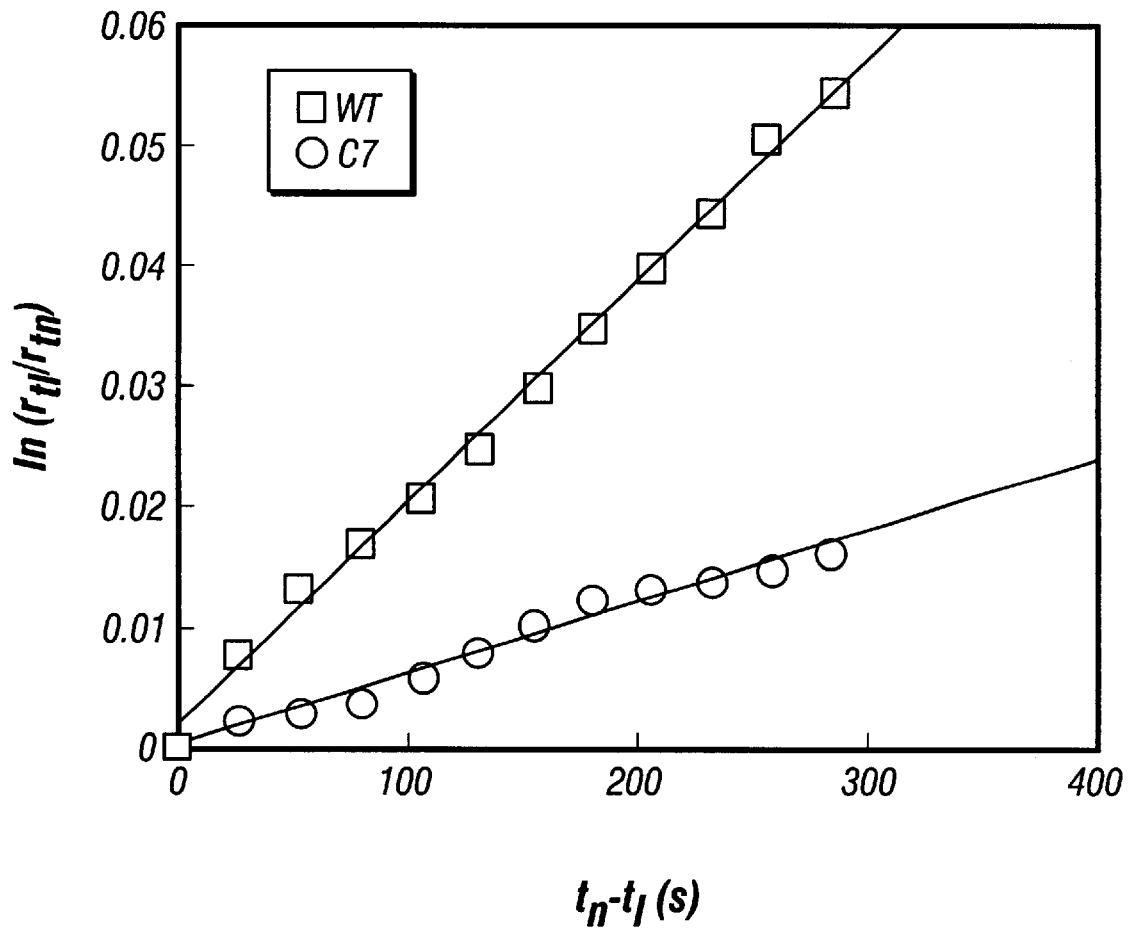
FIG. 12 shows dissociation rate ($k_{off}$) of wild-type Zif268 protein (WT) (□) and its variant C7 (○), by real-time changes in surface plasmon resonance.

As a measure of specificity, the affinity of each protein was determined for binding to the native consensus sequence and a mutant sequence in which one finger subsite had been changed. FIG. 11 shows the determination of dissociation rate ($k_{off}$) of wild-type Zif268 protein (WT) and its variant C7 by real-time changes in surface plasmon resonance. The response of the instrument, r, is proportional to [protein-DNA] complex. Since $dr/dt=k_{off}r$ when [protein]=0, then $k_{off}=\ln(r_{t1}/r_{tn})/(t_n-t_1)$, where $r_{tn}$ is the response at time $t_n$. The results of a single experiment for each protein are shown. Three experiments were performed to produce the values shown in FIG. 11. Clone C7 is improved 13-fold in affinity for binding the wild-type sequence GCG. The major contribution to this improvement in affinity is a 5-fold slowing of the dissociation rate of the complex (FIG. 12). Specificity of the C7 protein is also improved 9-fold with respect to the HIV-1 target sequence. This result suggest that additional or improved contacts are made in the complex. Studies of protein C9 demonstrate a different mechanism of improved specificity. In this case the overall affinity of C9 for the GCG site is equivalent to Zif268 but the specificity is improved 3-fold over Zif268 for binding to the TGT target site by an increase in the off-rate of this complex. Characterization of proteins F8 and F15 demonstrate that the 3 base pair recognition subsite of finger 1 can be completely changed to TGT and that new fingers can be selected to bind this site.

Characterization of proteins modified in the finger 2 domain and selected to bind the TTG subsite reveal the specificity of this finger is amenable to modification. Proteins G4 and G6 bind an oligonucleotide bearing the new subsite with affinities equivalent to Zif268 binding its consensus target. Specificity of these proteins for the target on which they were selected to bind is demonstrated by an approximately 4-fold better affinity for this oligonucleotide as compared to the native binding site which differs by a single base pair. This level of discrimination is similar to that reported for a finger 1 mutant (Jamieson, et al., supra). The finger 3 modified protein A14 was selected to bind the native finger 3 subsite and binds this site with an affinity which is only 2-fold lower than Zif268. Note that protein A14 differs radically in sequence from the native protein in the recognition subsite. Sequence specificity in 10 of the 11 proteins characterized was provided by differences in the stability of the complex. Only a single protein, G6, achieved specificity by a dramatic change in on-rate. Examination of on-rate variation with charge variation of the protein did not reveal a correlation.

Example 12

Dimeric Zinc Finger Construction

Zinc finger proteins of the invention can be manipulated to recognize and bind to extended target sequences. For example, zinc finger proteins containing from about 2 to 12 zinc fingers Zif(2) to Zif(12) may be fused to the leucine zipper domains of the Jun/Fos proteins, prototypical members of the bZIP family of proteins (O'Shea, et al., Science, 254:539, 1991). Alternatively, zinc finger proteins can be fused to other proteins which are capable of forming heterodimers and contain dimerization domains. Such proteins will be known to those of skill in the art.

The Jun/Fos leucine zippers preferentially form heterodimers and allow for the recognition of 12 to 72 base pairs. Henceforth, Jun/Fos refer to the leucine zipper domains of these proteins. Zinc finger proteins are fused to Jun, and independently to Fos by methods commonly used in the art to link proteins. Following purification, the Zif-Jun and Zif-Fos constructs (FIG. 13 and 14, respectively), the proteins are mixed to spontaneously form a Zif-Jun/Zif-Fos heterodimer. Alternatively, coexpression of the genes encoding these proteins results in the formation of Zif-Jun/Zif-Fos heterodimers in vivo. Fusion with an N-terminal nuclear localization signal allows for targeting of expression to the nucleus (Calderon, et al, Cell, 41:499, 1982). Activation domains may also be incorporated into one or each of the leucine zipper fusion constructs to produce activators of transcription (Sadowski, et al., Gene, 118:137, 1992). These dimeric constructs then allow for specific activation or repression of transcription. These heterodimeric Zif constructs are advantageous since they allow for recognition of palindromic sequences (if the fingers on both Jun and Fos recognize the same DNA/RNA sequence) or extended asymmetric sequences (if the fingers on Jun and Fos recognize different DNA/RNA sequences). For example the palindromic sequence

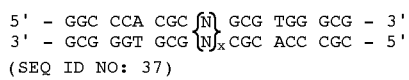

(SEQ ID NO: 37)

is recognized by the Zif268-Fos/Zif268 Jun dimer (x is any number). The spacing between subsites is determined by the site of fusion of Zif with the Jun or Fos zipper domains and the length of the linker between the Zif and zipper domains. Subsite spacing is determined by a binding site selection method as is common to those skilled in the art (Thiesen, et al., *Nucleic Acids Research,* 18:3203, 1990). Example of the recognition of an extended asymmetric sequence is shown by Zif(C7)$_6$-Jun/Zif-268-Fos dimer. This protein consists of 6 fingers of the C7 type (EXAMPLE 11) linked to Jun and three fingers of Zif268 linked to Fos, and recognizes the extended sequence:

```
5' - CGC CGC CGC CGC CGC CGC (N) GCG TGG GCG - 3'
3' - GCG GCG GCG GCG GCG GCG (N)x CGC ACC CGC - 5'
(SEQ ID NO: 38)
```

Example 13

Construction of Multifinger Proteins Utilizing Repeats of the First Finger of Zif268

Following mutagenesis and selection of variants of the Zif268 protein in which the finger 1 specificity or affinity was modified (See EXAMPLE 7), proteins carrying multiple copies of the finger may be constructed using the TGEKP linker sequence by methods known in the art. For example, the C7 finger may be constructed according to the scheme:

MKLLEPYACPVESCDRRFSKSADLKRHIRH<u>TGEKP</u>-

(YACPVESCDRRFSKSADLKHIRIH<u>TGEKP</u>)$_{1-11}$, where the sequence of the last linker is subject to change since it is at the terminus and not involved in linking two fingers together. An example of a three finger C7 construction is shown in FIG. 15. This protein binds the designed target sequence GCG-GCG-GCG (SEQ ID NO: 32) in the oligo-nucleotide hairpin CCT-CGC-CGC-CGC-GGG-TTT-TCC-CGC-GCC-CCC GAG G with an affinity of 9 nM, as compared to an affinity of 300 nM for an oligonucleotide encoding the GCG-TGG-GCG sequence (as determined by surface plasmon resonance studies). Proteins containing 2 to 12 copies of the C7 finger have been constructed and shown to have specificity for their predicted targets as determined by ELISA (see for example, Example 7). Fingers utilized need not be identical and may be mixed and matched to produce proteins which recognize a desired target sequence. These may also be utilized with leucine zippers (e.g., Fos/Jun) to produce proteins with extended sequence recognition.

In addition to producing polymers of finger 1, the entire three finger Zif268 and modified versions therein may be fused using the consensus linker TGEKP to produce proteins with extended recognition sites. For example, FIG. 16 shows the sequence of the protein Zif268—Zif268 in which the natural protein has been fused to itself using the TGEKP linker. This protein now binds the sequence GCG-TGG-GCG-GCG-TGG-GCG as demonstrated by ELISA. Therefore modifications within the three fingers of Zif268 may be fused together to form a protein which recognizes extended sequences. These new zinc proteins may also be used in combination with leucine zippers if desired, as described in Example 12.

Although the invention has been described with reference to the presently preferred embodiment, it should be understood that various modifications can be made without departing from the spirit of the invention. Accordingly, the invention is limited only by the following claims.

What is claimed is:

1. A method for isolating a zinc finger-nucleotide binding polypeptide variant which binds to a cellular nucleotide sequence comprising:
    a) identifying the amino acids in a zinc finger-nucleotide binding polypeptide that bind to a first cellular nucleotide sequence and modulate the function of a nucleotide sequence;
    b) creating an expression library encoding the polypeptide variant containing randomized substitution of the amino acids identified in step a) above;
    c) expressing the library in a suitable host cell; and
    d) isolating a clone that produces a polypeptide variant that binds to a second cellular nucleotide sequence and modulates the function of the second nucleotide sequence;
    wherein the variant is comprised of at least two zinc finger modules and wherein the amino acid sequence of each module that binds the second nucleotide sequence comprises two cysteines and two histidines whereby both cysteines are amino proximal to both histidines and wherein each of two modules of said variant has at least one amino acid sequence modification.

2. The method of claim 1, wherein the library is expressed in a phage surface expression system.

3. The method of claim 1, wherein the phage expression system includes a reducing reagent which allows folding of expression products on the phage surface.

4. The method of claim 3, wherein the reducing reagent is dithiothreitol.

5. The method of claim 1, wherein the library is randomized by PCR using primers containing degenerate triplet codons at sequence locations corresponding to the determined amino acids.

6. The method of claim 1, wherein the modulation of function is enhancement of transcription of a gene operatively linked to the cellular nucleotide sequence.

7. The method of claim 1, wherein the modulation of function is suppression of transcription of a gene operatively linked to the cellular nucleotide sequence.

8. The method of claim 1, wherein the cellular nucleotide sequence is DNA.

9. The method of claim 1, wherein the cellular nucleotide sequence is RNA.

10. The method of claim 1, wherein the variant is derived from a zinc finger-nucleotide binding polypeptide selected from the group consisting of zif 268 and TFIIIA.

11. The method of claim 1, wherein the variant derived from the zinc finger-nucleotide binding polypeptide zif268 is modified at any of residues 1, 3, 4, 5, 6 or 7 as set forth in SEQ ID NO:14.

12. The method of claim 1, wherein the variant derived from the zinc finger-nucleotide binding polypeptide zif268 is modified at any of residues 1, 2, 3, 4, 5 or 6 as set forth in SEQ ID NO:15.

13. The method of claim 1, wherein the variant derived from the zinc finger-nucleotide binding polypeptide zif268 is modified at any of residues 1, 3, 4, 5, 6 or 7 as set forth in SEQ ID NO:5.

14. A method for identifying a zinc finger-nucleotide binding polypeptide variant comprised of at least two zinc finger modules, which modulates the transcriptional function of cellular nucleotide sequence and binds to a zinc finger-nucleotide binding motif, wherein the amino acid sequence of each module that binds to a zinc finger nucleotide binding motif comprises two cysteines and two histidines whereby both cysteines are amino proximal to both histidines and wherein each of two modules of said variant has at least one amino acid sequence modification, said method comprising:
  a) incubating the components comprising a nucleotide sequence encoding the putative modulating variant operably linked to a first inducible promoter, and a reporter gene operably linked to a second inducible promoter and a zinc finger-nucleotide binding motif, wherein the incubating is carried out under conditions sufficient to allow the components to interact; and
  b) measuring the effect of the putative modulating variant on the expression of the reporter gene.

15. The method of claim 14, wherein the modulation is inhibition of gene expression.

16. The method of claim 14, wherein the modulation is enhancement of gene expression.

17. The method of claim 14, wherein the first inducible promoter is the arabinase promoter.

18. The method of claim 14, wherein the second inducible promoter is the lactose promoter.

19. The method of claim 14, wherein the incubating is performed in vitro.

20. The method of claim 14, wherein the incubating is performed in vivo.

21. The method of claim 14, wherein the reporter gene is β-galactosidase.

22. A method of modulating transcription of a cellular nucleotide sequence associated with a zinc finger-nucleotide binding motif, comprising contacting the zinc finger-nucleotide in cells in vitro with an effective amount of a zinc finger-nucleotide binding polypeptide variant comprised of at least two zinc finger modules that binds to the zinc finger-nucleotide binding motif, wherein the amino acid sequence of each module that binds the motif comprises two cysteines and two histidines whereby both cysteines are amino proximal to both histidines and wherein each of two modules of said variant has at least one amino acid sequence modification, thereby modulating transcriptional activity of the cellular nucleotide sequence.

23. The method of claim 22, wherein an expression vector comprising a polynucleotide sequence encoding a zinc finger-nucleotide binding polypeptide variant is introduced into the cells.

24. The method of claim 23, wherein the expression vector is a virus.

25. The method of claim 22, wherein the modulation is enhancement of transcription of a gene operatively linked to the cellular nucleotide sequence.

26. The method of claim 22, wherein the modulation is suppression of transcription of a gene operatively linked to the cellular nucleotide sequence.

27. The method of claims 1, 14, or 22 wherein the variant is derived from a zinc finger-nucleotide binding polypeptide selected from the group consisting of zif268 and TFIIIA.

28. An isolated zinc finger-nucleotide binding polypeptide variant comprising at least two zinc finger modules that bind to a target cellular nucleotide sequence and modulate the transcriptional function of the cellular nucleotide sequence, wherein the amino acid sequence of each zinc finger module that binds a target cellular nucleotide comprises two cysteines and two histidines whereby both cysteines are amino proximal to both histidines and wherein each of two modules of said variant has at least one amino acid sequence modification.

29. The variant of claim 28, wherein the modulation is enhancement of transcription of a gene operatively linked to the cellular nucleotide sequence.

30. The variant of claim 28, wherein the modulation is suppression of transcription of a gene operatively linked to the cellular nucleotide sequence.

31. The variant of claim 28, which is derived from a zinc finger-nucleotide binding polypeptide selected from the group consisting of zif 268 and TFIIIA.

32. The variant of claim 28, wherein the cellular nucleotide sequence is DNA.

33. The variant of claim 28, wherein the cellular nucleotide sequence is RNA.

34. The variant of claim 1, wherein the polypeptide contains a linker region between zinc fingers comprising the amino acid sequence TGEKP.

35. The variant of claim 28, wherein the cellular nucleotide sequence is a structural gene nucleotide sequence.

36. The variant of claim 28, wherein the cellular nucleotide sequence is a promoter nucleotide sequence.

37. The variant of claim 36, wherein the promoter is an onco-promoter.

38. The variant of claim 37, wherein the promoter is a viral promoter.

39. The variant of claim 28, wherein the cellular nucleotide sequence is a retroviral nucleotide sequence.

40. The variant of claim 39, wherein the retrovirus is a human T-cell lymphotrophic virus (HTLV).

41. The variant of claim 40, wherein the retrovirus is HTLV-1 or HTLV-2.

42. The variant of claim 39, wherein the retrovirus is a human immunodeficiency virus (HIV).

43. The variant of claim 42, wherein the retrovirus is HIV-1 or HIV-2.

44. The variant of claim 28, wherein the cellular nucleotide sequence is an oncogene nucleotide sequence.

45. The variant of claim 28, wherein the cellular nucleotide sequence is a plant cellular nucleotide sequence.

46. A zinc finger-nucleotide binding polypeptide variant produced by the method of claim 36.

47. An isolated nucleotide sequence encoding a zinc finger-nucleotide binding polypeptide variant of claim 28.

48. A recombinant expression vector containing a nucleotide sequence of claim 47.

49. A method for inhibiting a transcriptional function of a target cellular nucleotide sequence comprising a zinc finger-nucleotide binding motif, the method comprising contacting the motif with an effective amount of a zinc finger-nucleotide binding polypeptide variant comprised of at least two zinc finger molecules, wherein the amino acid sequence of each zinc finger module that binds the motif comprises two cysteines and two histidines whereby both cysteines are amino proximal to both histidines and wherein each of two modules has at least one amino acid sequence modification.

50. The method of claim 26, wherein the zinc finger binding polypeptide variant is a truncated zinc finger protein.

51. The method of claim 49, wherein the cellular nucleotide sequence is DNA.

52. The method of claim 49, wherein the cellular nucleotide sequence is RNA.

53. The method of claim 49, wherein the cellular nucleotide sequence is a structural gene nucleotide sequence.

54. The method of claim 49, wherein the cellular nucleotide sequence is a promoter nucleotide sequence.

55. The method of claim 49, wherein the cellular nucleotide sequence is an oncogene nucleotide sequence.

56. The method of claim 49, wherein the cellular nucleotide sequence is a plant cellular nucleotide sequence.

* * * * *

UNITED STATES PATENT AND TRADEMARK OFFICE
CERTIFICATE OF CORRECTION

PATENT NO. : 6,242,568 B1  
DATED : June 5, 2001  
INVENTOR(S) : Barbas III et al.

Page 1 of 1

It is certified that error appears in the above-identified patent and that said Letters Patent is hereby corrected as shown below:

Column 1,  
Line 9, after the PARENT CASE TEXT section, but prior to the DESCRIPTION section, please insert the following:
-- GOVERNMENTAL SUPPORT  
This invention was made with government support under Contract No. GM 47530 by the National Institutes of Health. The government has certain rights in this invention. --

Signed and Sealed this

Twenty-first Day of May, 2002

Attest:

Attesting Officer

JAMES E. ROGAN  
*Director of the United States Patent and Trademark Office*

UNITED STATES PATENT AND TRADEMARK OFFICE
CERTIFICATE OF CORRECTION

PATENT NO.    : 6,242,568 B1
DATED         : June 5, 2001
INVENTOR(S)   : Barbas III et al.

It is certified that error appears in the above-identified patent and that said Letters Patent is hereby corrected as shown below:

Column 1,
Line 11, please insert the following:
-- GOVERNMENTAL SUPPORT
This invention was made with government support under Contract No. GM 36643, GM 47530 and GM 53910 by the National Institutes of Health. The government has certain rights in this invention. --

Signed and Sealed this

Seventeenth Day of June, 2003

JAMES E. ROGAN
*Director of the United States Patent and Trademark Office*

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: peptide (ix) FEATURE:
      (B) LOCATION: 1
      (D) OTHER INFORMATION: where Xaa at position 1 can be Tyr or
         Phe.
      (B) LOCATION: 2, 4, 5, 7-9, 11-15, 17, 18, 20-22, 24 and 25
      (D) OTHER INFORMATION: where Xaa at positions 2, 4, 5, 7-9,
         11-15, 17, 18, 20-22, 24 and 25 are selected from
         arginine, lysine, glutamic acid, aspartic acid,
         glutamine, asparagine, serine, histidine, threonine,
         isoleucine, valine, leucine, alanine, cysteine, glycine,
         phenylalanine, proline, tryptophan, tyrosine, norleucine
         and methionine (xi) SEQUENCE DESCRIPTION: SEQ ID NO:1:

Xaa Xaa Cys Xaa Xaa Cys Xaa Xaa Xaa Phe Xaa Xaa Xaa Xaa Xaa Leu
1               5                   10                  15

Xaa Xaa His Xaa Xaa Xaa His Xaa Xaa
            20                  25

(2) INFORMATION FOR SEQ ID NO:2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ZF (ix) FEATURE:
        (A) NAME/KEY: CDS
        (B) LOCATION: 1..36

(xi) SEQUENCE DESCRIPTION: SEQ ID NO:2:

```
ATGAAACTGC TCGAGCCCTA TGCTTGCCCT GTCGAG                                36
```

(2) INFORMATION FOR SEQ ID NO:3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ZR (ix) FEATURE:
        (A) NAME/KEY: CDS
        (B) LOCATION: 1..45

(xi) SEQUENCE DESCRIPTION: SEQ ID NO:3:

```
GAGGAGGAGG AGACTAGTGT CCTTCTGTCT TAAATGGATT TTGGT                      45
```

(2) INFORMATION FOR SEQ ID NO:4:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: zif268Xho-Spe (ix) FEATURE:
        (A) NAME/KEY: CDS
        (B) LOCATION: 1..273

(xi) SEQUENCE DESCRIPTION: SEQ ID NO:4:

```
CTC GAG CCC TAT GCT TGC CCT GTC GAG TCC TGC GAT CGC CGC TTT TCT        48
Leu Glu Pro Tyr Ala Cys Pro Val Glu Ser Cys Asp Arg Arg Phe Ser
 1               5                  10                  15

CGC TCG GAT GAG CTT ACC CGC CAT ATC CGC ATC CAC ACA GGC CAG AAG        96
Arg Ser Asp Glu Leu Thr Arg His Ile Arg Ile His Thr Gly Gln Lys
             20                  25                  30

CCC TTC CAG TGT CGA ATA TGC ATG CGT AAC TTC AGT CGT AGT GAC CAC       144
Pro Phe Gln Cys Arg Ile Cys Met Arg Asn Phe Ser Arg Ser Asp His
         35                  40                  45

CTT ACC ACC CAC ATC CGC ACC CAC ACA GGC GAG AAG CCT TTT GCC TGT       192
Leu Thr Thr His Ile Arg Thr His Thr Gly Glu Lys Pro Phe Ala Cys
```

```
               50                  55                  60
GAC ATT TGT GGG AGG AAG TTT GCC AGG AGT GAT GAA CGC AAG AGG CAT        240
Asp Ile Cys Gly Arg Lys Phe Ala Arg Ser Asp Glu Arg Lys Arg His
 65                  70                  75                  80

ACC AAA ATC CAT TTA AGA CAG AAG GAC ACT AGT                            273
Thr Lys Ile His Leu Arg Gln Lys Asp Thr Ser
                 85                  90
```

(2) INFORMATION FOR SEQ ID NO:5:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:5:

```
Leu Glu Pro Tyr Ala Cys Pro Val Glu Ser Cys Asp Arg Arg Phe Ser
 1                   5                  10                  15

Arg Ser Asp Glu Leu Thr Arg His Ile Arg Ile His Thr Gly Gln Lys
                 20                  25                  30

Pro Phe Gln Cys Arg Ile Cys Met Arg Asn Phe Ser Arg Ser Asp His
             35                  40                  45

Leu Thr Thr His Ile Arg Thr His Thr Gly Glu Lys Pro Phe Ala Cys
         50                  55                  60

Asp Ile Cys Gly Arg Lys Phe Ala Arg Ser Asp Glu Arg Lys Arg His
 65                  70                  75                  80

Thr Lys Ile His Leu Arg Gln Lys Asp Thr Ser
                 85                  90
```

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: FTX3

(ix) FEATURE:
        (A) NAME/KEY: CDS
        (B) LOCATION: 1..22

(xi) SEQUENCE DESCRIPTION: SEQ ID NO:6:

```
GCAATTAACC CTCACTAAAG GG                                                22
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: BZF3

(ix) FEATURE:
        (A) NAME/KEY: CDS
        (B) LOCATION: 1..21

(xi) SEQUENCE DESCRIPTION: SEQ ID NO:7:

GGCAAACTTC CTCCCACAAA T                                              21

(2) INFORMATION FOR SEQ ID NO:8:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ZF36K (ix) FEATURE:
        (A) NAME/KEY: CDS
        (B) LOCATION: 1..60

(xi) SEQUENCE DESCRIPTION: SEQ ID NO:8:

ATTTGTGGGA GGAAGTTTGC CNNKAGTNNK NNKNNKNNKN NKCATACCAA AATCCATTTA     60

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: R3B (ix) FEATURE:
        (A) NAME/KEY: CDS
        (B) LOCATION: 1..21

(xi) SEQUENCE DESCRIPTION: SEQ ID NO:9:

TTGATATTCA CAAACGAATG G                                              21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: ZFNsi-B (ix) FEATURE:
        (A) NAME/KEY: CDS
        (B) LOCATION: 1..21

(xi) SEQUENCE DESCRIPTION: SEQ ID NO:10:

CATGCATATT CGACACTGGA A                                              21

(2) INFORMATION FOR SEQ ID NO:11:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
          (B) CLONE: ZF2r6F (ix) FEATURE:
          (A) NAME/KEY: CDS
          (B) LOCATION: 1..66

(xi) SEQUENCE DESCRIPTION: SEQ ID NO:11:

CAGTGTCGAA TATGCATGCG TAACTTCNNK NNKNNKNNKN NKNNKACCAC CCACATCCGC    60

ACCCAC    66

(2) INFORMATION FOR SEQ ID NO:12:

(i) SEQUENCE CHARACTERISTICS:
          (A) LENGTH: 66 base pairs
          (B) TYPE: nucleic acid
          (C) STRANDEDNESS: single
          (D) TOPOLOGY: linear (ii) MOLECULE TYPE: DNA (genomic)

(vii) IMMEDIATE SOURCE:
          (B) CLONE: AFI6rb (ix) FEATURE:
          (A) NAME/KEY: CDS
          (B) LOCATION: 1..66

(xi) SEQUENCE DESCRIPTION: SEQ ID NO:12:

CTGGCCTGTG TGGATGCGGA TATGMNNMNN MNNMNNMNNC GAMNNAGAAA AGCGGCGATC    60

GCAGGA    66

(2) INFORMATION FOR SEQ ID NO:13:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(vii) IMMEDIATE SOURCE:
          (B) CLONE: ZFIF (ix) FEATURE:
          (A) NAME/KEY: CDS
          (B) LOCATION: 1..24

(xi) SEQUENCE DESCRIPTION: SEQ ID NO:13:

CATATCCGCA TCCACACAGG CCAG    24

(2) INFORMATION FOR SEQ ID NO:14:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION: 1..8

(xi) SEQUENCE DESCRIPTION: SEQ ID NO:14:

```
Arg Ser Asp Glu Leu Thr Arg His
1               5
```

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6

(xi) SEQUENCE DESCRIPTION: SEQ ID NO:15:

```
Ser Arg Ser Asp His Leu
1               5
```

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..34

(xi) SEQUENCE DESCRIPTION: SEQ ID NO:16:

```
CGTAAATGGG CGCCCTTTTG GGCGCCCATT TACG                              34
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO:17:

```
Arg Ser Asp Glu Arg Lys Arg His
1               5
```

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO:18:

```
Trp Ser Ile Pro Val Leu Leu His
1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO:19:

```
Trp Ser Leu Leu Pro Val Leu His
1               5
```

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO:20:

```
Phe Ser Phe Leu Leu Pro Leu His
1               5
```

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO:21:

```
Leu Ser Thr Trp Arg Gly Trp His
1               5
```

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8

(xi) SEQUENCE DESCRIPTION: SEQ ID NO:22:

Thr Ser Ile Gln Leu Pro Tyr His
1               5

(2) INFORMATION FOR SEQ ID NO:23:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 1..61

(xi) SEQUENCE DESCRIPTION: SEQ ID NO:23:

TGATCTCAGA AGCCAAGCAG GGTCGGGCCT GGTTAGTACT TGGATGGGAG ACCGCCTGGG      60

A                                                                     61

(2) INFORMATION FOR SEQ ID NO:24:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION: 1..26

(xi) SEQUENCE DESCRIPTION: SEQ ID NO:24:

Tyr Ile Cys Ser Phe Ala Asp Cys Gly Ala Ala Tyr Asn Lys Asn Trp
1               5                   10                  15

Lys Leu Gln Ala His Leu Cys Lys His Thr
            20                  25

(2) INFORMATION FOR SEQ ID NO:25:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Peptide
         (B) LOCATION: 1..26

(xi) SEQUENCE DESCRIPTION: SEQ ID NO:25:

Phe Pro Cys Lys Glu Glu Gly Cys Glu Lys Gly Phe Thr Ser Leu His
1               5                   10                  15

His Leu Thr Arg His Ser Leu Thr His Thr
            20                  25

(2) INFORMATION FOR SEQ ID NO:26:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
            (A) NAME/KEY: Peptide
            (B) LOCATION: 1..26

(xi) SEQUENCE DESCRIPTION: SEQ ID NO:26:

Phe Thr Cys Asp Ser Asp Gly Cys Asp Leu Arg Phe Thr Thr Lys Ala
1               5                  10                  15

Asn Met Lys Lys His Phe Asn Arg Phe His
            20                  25

(2) INFORMATION FOR SEQ ID NO:27:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..13

(xi) SEQUENCE DESCRIPTION: SEQ ID NO:27:

TGGATGGGAG ACC                                                               13

(2) INFORMATION FOR SEQ ID NO:28:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..8

(xi) SEQUENCE DESCRIPTION: SEQ ID NO:28:

Arg Ser Asp Glu Arg Lys Arg His
1               5

(2) INFORMATION FOR SEQ ID NO:29:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..21

(xi) SEQUENCE DESCRIPTION: SEQ ID NO:29:

GTCCATAAGA TTAGCGGATC C                                                      21

(2) INFORMATION FOR SEQ ID NO:30:

(i) SEQUENCE CHARACTERISTICS:
            (A) LENGTH: 21 base pairs
            (B) TYPE: nucleic acid (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..21

(xi) SEQUENCE DESCRIPTION: SEQ ID NO:30:

GTGAGCGAGG AAGCGGAAGA G                                                  21

(2) INFORMATION FOR SEQ ID NO:31:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..34

(xi) SEQUENCE DESCRIPTION: SEQ ID NO:31:

CCTGCGTGGG CGCCCTTTTG GGCGCCCACG CAGG                                    34

(2) INFORMATION FOR SEQ ID NO:32:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..5

(xi) SEQUENCE DESCRIPTION: SEQ ID NO:32:

Thr Gly Glu Lys Pro
1               5

(2) INFORMATION FOR SEQ ID NO:33:

(i) SEQUENCE CHARACTERISTICS:
            (A) LENGTH: 462 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: zif268-jun (ix) FEATURE:
            (A) NAME/KEY: CDS
            (B) LOCATION: 1..459

(xi) SEQUENCE DESCRIPTION: SEQ ID NO:33:

ATG CTC GAG CTC CCC TAT GCT TGC CCT GTC GAG TCC TGC GAT CGC CGC          48
Met Leu Glu Leu Pro Tyr Ala Cys Pro Val Glu Ser Cys Asp Arg Arg
 1               5                  10                  15

TTT TCT CGC TCG GAT GAG CTT ACC CGC CAT ATC CGC ATC CAC ACA GGC          96
Phe Ser Arg Ser Asp Glu Leu Thr Arg His Ile Arg Ile His Thr Gly
             20                  25                  30

```
CAG AAG CCC TTC CAG TGT CGA ATA TGC ATG CGT AAC TTC AGT CGT AGT        144
Gln Lys Pro Phe Gln Cys Arg Ile Cys Met Arg Asn Phe Ser Arg Ser
        35                  40                  45

GAC CAC CTT ACC ACC CAC ATC CGC ACC CAC ACA GGC GAG AAG CCT TTT        192
Asp His Leu Thr Thr His Ile Arg Thr His Thr Gly Glu Lys Pro Phe
    50                  55                  60

GCC TGT GAC ATT TGT GGG AGG AAG TTT GCC AGG AGT GAT GAA CGC AAG        240
Ala Cys Asp Ile Cys Gly Arg Lys Phe Ala Arg Ser Asp Glu Arg Lys
65                  70                  75                  80

AGG CAT ACC AAA ATC CAT ACC GGT CAG AAG CCC ACT AGT GGC GGT GGT        288
Arg His Thr Lys Ile His Thr Gly Gln Lys Pro Thr Ser Gly Gly Gly
                85                  90                  95

CGG ATC GCC CGG CTG GAG GAA AAA GTG AAA ACC TTG AAA GCG CAA AAC        336
Arg Ile Ala Arg Leu Glu Glu Lys Val Lys Thr Leu Lys Ala Gln Asn
            100                 105                 110

TCC GAG CTG GCG TCC ACC GCC AAC ATG CTC AGG GAA CAG GTG GCA CAG        384
Ser Glu Leu Ala Ser Thr Ala Asn Met Leu Arg Glu Gln Val Ala Gln
        115                 120                 125

CTT AAA CAG AAA GTC ATG AAC CAC GCT AGC GGC CAG GCC GGC CAG TAC        432
Leu Lys Gln Lys Val Met Asn His Ala Ser Gly Gln Ala Gly Gln Tyr
    130                 135                 140

CCG TAC GAC GTT CCG GAC TAC GCT TCT TAA                                462
Pro Tyr Asp Val Pro Asp Tyr Ala Ser
145                 150
```

(2) INFORMATION FOR SEQ ID NO:34:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:34:

```
Met Leu Glu Leu Pro Tyr Ala Cys Pro Val Glu Ser Cys Asp Arg Arg
1               5                   10                  15

Phe Ser Arg Ser Asp Glu Leu Thr Arg His Ile Arg Ile His Thr Gly
            20                  25                  30

Gln Lys Pro Phe Gln Cys Arg Ile Cys Met Arg Asn Phe Ser Arg Ser
        35                  40                  45

Asp His Leu Thr Thr His Ile Arg Thr His Thr Gly Glu Lys Pro Phe
    50                  55                  60

Ala Cys Asp Ile Cys Gly Arg Lys Phe Ala Arg Ser Asp Glu Arg Lys
65                  70                  75                  80

Arg His Thr Lys Ile His Thr Gly Gln Lys Pro Thr Ser Gly Gly Gly
                85                  90                  95

Arg Ile Ala Arg Leu Glu Glu Lys Val Lys Thr Leu Lys Ala Gln Asn
            100                 105                 110

Ser Glu Leu Ala Ser Thr Ala Asn Met Leu Arg Glu Gln Val Ala Gln
        115                 120                 125

Leu Lys Gln Lys Val Met Asn His Ala Ser Gly Gln Ala Gly Gln Tyr
    130                 135                 140

Pro Tyr Asp Val Pro Asp Tyr Ala Ser
145                 150
```

(2) INFORMATION FOR SEQ ID NO:35:

(i) SEQUENCE CHARACTERISTICS:

(A) LENGTH: 462 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: zif268-fos (ix) FEATURE:
        (A) NAME/KEY: CDS
        (B) LOCATION: 1..459

(xi) SEQUENCE DESCRIPTION: SEQ ID NO:35:

```
ATG CTC GAG CTC CCC TAT GCT TGC CCT GTC GAG TCC TGC GAT CGC CGC       48
Met Leu Glu Leu Pro Tyr Ala Cys Pro Val Glu Ser Cys Asp Arg Arg
 1               5                  10                  15

TTT TCT CGC TCG GAT GAG CTT ACC CGC CAT ATC CGC ATC CAC ACA GGC       96
Phe Ser Arg Ser Asp Glu Leu Thr Arg His Ile Arg Ile His Thr Gly
             20                  25                  30

CAG AAG CCC TTC CAG TGT CGA ATA TGC ATG CGT AAC TTC AGT CGT AGT      144
Gln Lys Pro Phe Gln Cys Arg Ile Cys Met Arg Asn Phe Ser Arg Ser
         35                  40                  45

GAC CAC CTT ACC ACC CAC ATC CGC ACC CAC ACA GGC GAG AAG CCT TTT      192
Asp His Leu Thr Thr His Ile Arg Thr His Thr Gly Glu Lys Pro Phe
     50                  55                  60

GCC TGT GAC ATT TGT GGG AGG AAG TTT GCC AGG AGT GAT GAA CGC AAG      240
Ala Cys Asp Ile Cys Gly Arg Lys Phe Ala Arg Ser Asp Glu Arg Lys
 65                  70                  75                  80

AGG CAT ACC AAA ATC CAT ACC GGT CAG AAG CCC ACT AGT GGC GGT GGT      288
Arg His Thr Lys Ile His Thr Gly Gln Lys Pro Thr Ser Gly Gly Gly
                 85                  90                  95

CTG ACC GAC ACC CTG CAG GCG GAA ACC GAC CAG CTG GAA GAC GAA AAA      336
Leu Thr Asp Thr Leu Gln Ala Glu Thr Asp Gln Leu Glu Asp Glu Lys
            100                 105                 110

TCC GCG CTG CAA ACC GAA ATC GCG AAC CTG CTG AAA GAA AAA GAA AAG      384
Ser Ala Leu Gln Thr Glu Ile Ala Asn Leu Leu Lys Glu Lys Glu Lys
        115                 120                 125

CTG GAG TTC ATC CTG GCG GCA CAC GCT AGC GGC CAG GCC GGC CAG TAC      432
Leu Glu Phe Ile Leu Ala Ala His Ala Ser Gly Gln Ala Gly Gln Tyr
    130                 135                 140

CCG TAC GAC GTT CCG GAC TAC GCT TCT TAA                              462
Pro Tyr Asp Val Pro Asp Tyr Ala Ser
145                 150
```

(2) INFORMATION FOR SEQ ID NO:36:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:36:

```
Met Leu Glu Leu Pro Tyr Ala Cys Pro Val Glu Ser Cys Asp Arg Arg
 1               5                  10                  15

Phe Ser Arg Ser Asp Glu Leu Thr Arg His Ile Arg Ile His Thr Gly
             20                  25                  30

Gln Lys Pro Phe Gln Cys Arg Ile Cys Met Arg Asn Phe Ser Arg Ser
         35                  40                  45

Asp His Leu Thr Thr His Ile Arg Thr His Thr Gly Glu Lys Pro Phe
     50                  55                  60
```

-continued

```
Ala Cys Asp Ile Cys Gly Arg Lys Phe Ala Arg Ser Asp Glu Arg Lys
 65                  70                  75                  80

Arg His Thr Lys Ile His Thr Gly Gln Lys Pro Thr Ser Gly Gly Gly
                 85                  90                  95

Leu Thr Asp Thr Leu Gln Ala Glu Thr Asp Gln Leu Glu Asp Glu Lys
            100                 105                 110

Ser Ala Leu Gln Thr Glu Ile Ala Asn Leu Leu Lys Glu Lys Glu Lys
        115                 120                 125

Leu Glu Phe Ile Leu Ala Ala His Ala Ser Gly Gln Ala Gly Gln Tyr
    130                 135                 140

Pro Tyr Asp Val Pro Asp Tyr Ala Ser
145                 150
```

(2) INFORMATION FOR SEQ ID NO:37:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..19

(xi) SEQUENCE DESCRIPTION: SEQ ID NO:37:

GGCCCACGCN GCGTGGGCG                                        19

(2) INFORMATION FOR SEQ ID NO:38:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..28

(xi) SEQUENCE DESCRIPTION: SEQ ID NO:38:

CGCCGCCGCC GCCGCCGCNG CGTGGGCG                            28

(2) INFORMATION FOR SEQ ID NO:39:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..64

(xi) SEQUENCE DESCRIPTION: SEQ ID NO:39:

```
Met Lys Leu Leu Glu Pro Tyr Ala Cys Pro Val Glu Ser Cys Asp Arg
 1               5                  10                  15

Arg Phe Ser Lys Ser Ala Asp Leu Lys Arg His Ile Arg His Thr Gly
                20                  25                  30
```

```
        Glu Lys Pro Tyr Ala Cys Pro Val Glu Ser Cys Asp Arg Arg Phe Ser
                 35                  40                  45

Lys Ser Ala Asp Leu Lys His Ile Arg Ile His Thr Gly Glu Lys Pro
         50                  55                  60
```

(2) INFORMATION FOR SEQ ID NO:40:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..34

(xi) SEQUENCE DESCRIPTION: SEQ ID NO:40:

```
CCTCGCCGCC GCGGGTTTTC CCGCGCCCCC GAGG                                34
```

(2) INFORMATION FOR SEQ ID NO:41:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: C7[3 finger]

(ix) FEATURE:
        (A) NAME/KEY: CDS
        (B) LOCATION: 1..294

(xi) SEQUENCE DESCRIPTION: SEQ ID NO:41:

```
ATG AAA CTG CTC GAG CCC TAT GCT TGC CCT GTC GAG TCC TGC GAT CGC      48
Met Lys Leu Leu Glu Pro Tyr Ala Cys Pro Val Glu Ser Cys Asp Arg
 1               5                  10                  15

CGC TTT TCT AAG TCG GCT GAT CTG AAG CGC CAT ATC CGC ATC CAC ACT      96
Arg Phe Ser Lys Ser Ala Asp Leu Lys Arg His Ile Arg Ile His Thr
                 20                  25                  30

GGC GAA AAA CCG TAC GCG TGC CCT GTC GAG TCC TGC GAT CGC CGC TTT     144
Gly Glu Lys Pro Tyr Ala Cys Pro Val Glu Ser Cys Asp Arg Arg Phe
             35                  40                  45

TCT AAG TCG GCT GAT CTG AAG CGC CAT ATC CGC ATC CAC ACC GGG GAG     192
Ser Lys Ser Ala Asp Leu Lys Arg His Ile Arg Ile His Thr Gly Glu
 50                  55                  60

AAG CCC TAT GCT TGC CCT GTC GAG TCC TGC GAT CGC CGC TTT TCT AAG     240
Lys Pro Tyr Ala Cys Pro Val Glu Ser Cys Asp Arg Arg Phe Ser Lys
 65                  70                  75                  80

TCG GCT GAT CTG AAG CGC CAT ATC CGC ATC CAC ACC GGT CAG AAG CCC     288
Ser Ala Asp Leu Lys Arg His Ile Arg Ile His Thr Gly Gln Lys Pro
                 85                  90                  95

ACT AGT                                                              294
Thr Ser
```

(2) INFORMATION FOR SEQ ID NO:42:

(i) SEQUENCE CHARACTERISTICS:
        (A) LENGTH: 98 amino acids
        (B) TYPE: amino acid (D) TOPOLOGY: linear (ii) MOLECULE TYPE: protein (xi) SEQUENCE DESCRIPTION: SEQ ID NO:42:

```
Met Lys Leu Leu Glu Pro Tyr Ala Cys Pro Val Glu Ser Cys Asp Arg
  1               5                  10                  15

Arg Phe Ser Lys Ser Ala Asp Leu Lys Arg His Ile Arg Ile His Thr
                20                  25                  30

Gly Glu Lys Pro Tyr Ala Cys Pro Val Glu Ser Cys Asp Arg Arg Phe
             35                  40                  45

Ser Lys Ser Ala Asp Leu Lys Arg His Ile Arg Ile His Thr Gly Glu
     50                  55                  60

Lys Pro Tyr Ala Cys Pro Val Glu Ser Cys Asp Arg Arg Phe Ser Lys
 65                  70                  75                  80

Ser Ala Asp Leu Lys Arg His Ile Arg Ile His Thr Gly Gln Lys Pro
                 85                  90                  95

Thr Ser
```

(2) INFORMATION FOR SEQ ID NO:43:

(i) SEQUENCE CHARACTERISTICS:
    (A) LENGTH: 543 base pairs
    (B) TYPE: nucleic acid
    (C) STRANDEDNESS: single
    (D) TOPOLOGY: linear (ii) MOLECULE TYPE: DNA (genomic)

(vii) IMMEDIATE SOURCE:
    (B) CLONE: zif268-zif268

(ix) FEATURE:
    (A) NAME/KEY: CDS
    (B) LOCATION: 1..543

(xi) SEQUENCE DESCRIPTION: SEQ ID NO:43:

```
ATG CTC GAG CTC CCC TAT GCT TGC CCT GTC GAG TCC TGC GAT CGC CGC      48
Met Leu Glu Leu Pro Tyr Ala Cys Pro Val Glu Ser Cys Asp Arg Arg
  1               5                  10                  15

TTT TCT CGC TCG GAT GAG CTT ACC CGC CAT ATC CGC ATC CAC ACA GGC      96
Phe Ser Arg Ser Asp Glu Leu Thr Arg His Ile Arg Ile His Thr Gly
                 20                  25                  30

CAG AAG CCC TTC CAG TGT CGA ATA TGC ATG CGT AAC TTC AGT CGT AGT     144
Gln Lys Pro Phe Gln Cys Arg Ile Cys Met Arg Asn Phe Ser Arg Ser
             35                  40                  45

GAC CAC CTT ACC ACC CAC ATC CGC ACC CAC ACA GGC GAG AAG CCT TTT     192
Asp His Leu Thr Thr His Ile Arg Thr His Thr Gly Glu Lys Pro Phe
     50                  55                  60

GCC TGT GAC ATT TGT GGG AGG AAG TTT GCC AGG AGT GAT GAA CGC AAG     240
Ala Cys Asp Ile Cys Gly Arg Lys Phe Ala Arg Ser Asp Glu Arg Lys
 65                  70                  75                  80

AGG CAT ACC AAA ATC CAT ACC GGG GAG AAG CCC TAT GCT TGC CCT GTC     288
Arg His Thr Lys Ile His Thr Gly Glu Lys Pro Tyr Ala Cys Pro Val
                 85                  90                  95

GAG TCC TGC GAT CGC CGC TTT TCT CGC TCG GAT GAG CTT ACC CGC CAT     336
Glu Ser Cys Asp Arg Arg Phe Ser Arg Ser Asp Glu Leu Thr Arg His
                100                 105                 110

ATC CGC ATC CAC ACA GGC CAG AAG CCC TTC CAG TGT CGA ATA TGC ATG     384
Ile Arg Ile His Thr Gly Gln Lys Pro Phe Gln Cys Arg Ile Cys Met
             115                 120                 125

CGT AAC TTC AGT CGT AGT GAC CAC CTT ACC ACC CAC ATC CGC ACC CAC     432
```

-continued

```
Arg Asn Phe Ser Arg Ser Asp His Leu Thr Thr His Ile Arg Thr His
    130                 135                 140

ACA GGC GAG AAG CCT TTT GCC TGT GAC ATT TGT GGG AGG AAG TTT GCC       480
Thr Gly Glu Lys Pro Phe Ala Cys Asp Ile Cys Gly Arg Lys Phe Ala
145                 150                 155                 160

AGG AGT GAT GAA CGC AAG AGG CAT ACC AAA ATC CAT TTA AGA CAG AAG       528
Arg Ser Asp Glu Arg Lys Arg His Thr Lys Ile His Leu Arg Gln Lys
                165                 170                 175

GAC TCT AGA ACT AGT                                                   543
Asp Ser Arg Thr Ser
            180
```

(2) INFORMATION FOR SEQ ID NO:44:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:44:

```
Met Leu Glu Leu Pro Tyr Ala Cys Pro Val Glu Ser Cys Asp Arg Arg
1                   5                   10                  15

Phe Ser Arg Ser Asp Glu Leu Thr Arg His Ile Arg Ile His Thr Gly
                20                  25                  30

Gln Lys Pro Phe Gln Cys Arg Ile Cys Met Arg Asn Phe Ser Arg Ser
            35                  40                  45

Asp His Leu Thr Thr His Ile Arg Thr His Thr Gly Glu Lys Pro Phe
        50                  55                  60

Ala Cys Asp Ile Cys Gly Arg Lys Phe Ala Arg Ser Asp Glu Arg Lys
65                  70                  75                  80

Arg His Thr Lys Ile His Thr Gly Glu Lys Pro Tyr Ala Cys Pro Val
                85                  90                  95

Glu Ser Cys Asp Arg Arg Phe Ser Arg Ser Asp Glu Leu Thr Arg His
                100                 105                 110

Ile Arg Ile His Thr Gly Gln Lys Pro Phe Gln Cys Arg Ile Cys Met
            115                 120                 125

Arg Asn Phe Ser Arg Ser Asp His Leu Thr Thr His Ile Arg Thr His
    130                 135                 140

Thr Gly Glu Lys Pro Phe Ala Cys Asp Ile Cys Gly Arg Lys Phe Ala
145                 150                 155                 160

Arg Ser Asp Glu Arg Lys Arg His Thr Lys Ile His Leu Arg Gln Lys
                165                 170                 175

Asp Ser Arg Thr Ser
            180
```